United States Patent
Onishi et al.

[11] Patent Number: 6,001,275
[45] Date of Patent: Dec. 14, 1999

[54] LIQUID-CRYSTALLINE COMPOUND HAVING DIENYL MOIETY AND LIQUID-CRYSTAL COMPOSITION

[75] Inventors: Noriyuki Onishi, Kumamoto; Koichi Shibata, Chiba; Yasuhiro Haseba, Chiba; Yasuyuki Koizumi, Chiba; Shuichi Matsui, Chiba; Kazutoshi Miyazawa, Chiba; Yasuko Sekiguchi, Chiba; Etsuo Nakagawa, Chiba, all of Japan

[73] Assignee: Chisso Corporation, Osaka, Japan

[21] Appl. No.: 08/890,547

[22] PCT Filed: Jan. 19, 1996

[86] PCT No.: PCT/JP96/00083

§ 371 Date: Jul. 9, 1997

§ 102(e) Date: Jul. 9, 1997

[87] PCT Pub. No.: WO96/22261

PCT Pub. Date: Jul. 25, 1996

[30] Foreign Application Priority Data

Jan. 20, 1995 [JP] Japan .................. 7-026029
Nov. 2, 1995 [JP] Japan .................. 7-310039

[51] Int. Cl.$^6$ .................. C09K 19/52; C07D 239/02; C07D 211/82
[52] U.S. Cl. .................. 252/299.01; 252/299.61; 252/299.62; 252/299.63; 252/299.66; 252/299.67; 544/180; 544/238; 544/242; 544/336; 546/350
[58] Field of Search .................. 252/299.01, 299.61, 252/299.62, 299.63, 299.66, 299.67; 544/180, 238, 242, 336; 546/350; 585/600

[56] References Cited

U.S. PATENT DOCUMENTS 5,328,637  7/1994  Buchecker et al. .................. 252/299.6
5,609,791  3/1997  Fujita et al. .................. 252/299.63
5,744,058  4/1998  Reiffenrath et al. .................. 252/299.66

*Primary Examiner*—Shean C. Wu
*Attorney, Agent, or Firm*—Wenderoth, Lind & Ponack, L.L.P.

[57] ABSTRACT

The present invention is concerned with a liquid crystalline compound expressed by general formula (1)

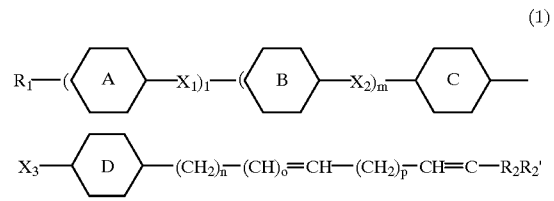

wherein $R_1$ represents cyano group, halogen atom, or a straight or branched alkyl group or halogenated alkyl group having 1 to 20 carbon atoms, one or not-adjacent two $CH_2$ groups in the alkyl group or halogenated alkyl group may be replaced by oxygen atom or —CH=CH— group; $R_2$ and $R_2'$ represent hydrogen atom, halogen atom, or an alkyl group having 1 to 9 carbon atoms; $X_1$, $X_2$, and $X_3$ independently represent —$CH_2CH_2$—, —CO—O—, —O—CO—, —CH=CH—, —C≡C—, —$(CH_2)_4$—, —$CF_2$O—, —$OCF_2$—, —$CH_2$O—, —$OCH_2$—, or a covalent bond; rings A, B, C, and D independently represent 1,4-phenylene ring, trans-1,4-cyclohexylene ring, bicyclo[1,1,0]butane ring, bicyclo[1,1,1]pentane ring, bicyclo[3,2,2]octane ring, cyclobutane ring, or spiro[3,3]heptane ring, respectively, hydrogen atom in these rings may be replaced by halogen atom and carbon atom in these rings may be replaced by nitrogen atom or oxygen atom; l, m, and o are independently 0 or 1, n is an integer of 0 to 3, and p is an integer of 1 to 5.

13 Claims, No Drawings

LIQUID-CRYSTALLINE COMPOUND HAVING DIENYL MOIETY AND LIQUID-CRYSTAL COMPOSITION

This application is a 371 of PCT/JP96/00083 filed Jan. 9, 1996.

TECHNICAL FIELD

The present invention relates to a novel liquid crystalline compound which develops preferable physical properties and to a liquid crystal composition comprising the novel liquid crystalline compound mentioned above and having preferable physical properties.

BACKGROUND ART

Liquid crystal display devices employ the optical anisotropy and dielectric anisotropy of liquid crystal compounds. As their display mode, twisted nematic mode (TN mode), super twisted nematic mode (STN mode), dynamic scattering mode (DS mode), guest-host mode (GH mode), and DAP mode are known. As their driving mode, static driving mode, time sharing addressing mode, active matrix driving mode, and dual frequency driving mode are known.

Whereas the properties of liquid crystalline compounds used for these liquid crystal display devices are different depending on their uses, it is required of any of the liquid crystalline compounds that they are stable against external environmental factors such as moisture, air, heat, and light, and that they exhibit a liquid crystal phase at a range of temperatures as wide as possible with room temperature preferably being at its center.

Liquid crystal compositions are composed of several or twenty-odd liquid crystalline compounds to develop most suitable characteristics required of a particular display device. Therefore, liquid crystalline compounds are required to be excellent in miscibility with other liquid crystalline compounds, even in the miscibility at low temperatures particularly from the latest demand for their use in various environment.

Especially, steep threshold characteristics are required of liquid crystal compositions used in STN driving to actualize high picture quality. The steepness is a function of the ratio of elastic constants $K_{33}/K_{11}$, and it is known that the larger the ratio of the elastic constants of liquid crystalline compounds are used in a liquid crystal composition, the steeper threshold characteristics the composition exhibits (F. Leenhouts et al., Proceedings of the Japan Display, 388 (1986) ).

Also, it is necessary to use a liquid crystal composition having a high response speed for realizing a large screen of display device. It is known that the response speed is a function of viscosity (E. Jakeman et al., Phys. Lett., 39A, 69 (1972) ). That is, it is important to use liquid crystalline compounds having a low viscosity necessary for actualizing a composition having a low viscosity.

As the compound having a large elastic constant ratio $K_{33}/K_{11}$, compounds which have an alkenyl moiety are known. That is, they are the compounds described in M. Schadt et al., Mol. Cryst. Liq. Cryst., 122 (1985) and Laid-open Japanese Patent Publication No. Sho 61-83136; and the compounds having introduced fluorine atom and described in Japanese Patent Application No. Hei 6-92740, each of which are shown below.

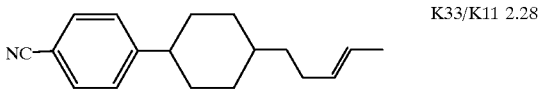

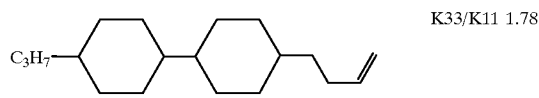

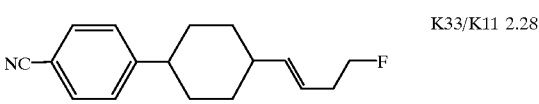

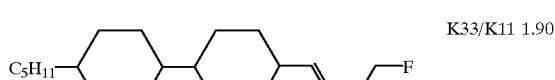

Any of these alkenyl compounds has a large ratio of elastic constants $K_{33}/K_{11}$ (about 1.78 to 2.28) and liquid crystal compositions comprising these compounds exhibit a preferable steepness. (Elastic constant ratio $K_{33}/K_{11}$ of the four compounds mentioned above are the values determined under the same conditions as in Example 7 (Use Example 1) mentioned below.) However, as the demand on the displaying ability of liquid crystal display devices has increased, liquid crystal compositions having a higher response speed, in other words, liquid crystal compositions having a lower viscosity have been demanded.

As the compounds having a large elastic constant ratio $K_{33}/K_{11}$, compounds having 1,3-butadienyl group are described in Laid Open Japanese Patent Publication No. Hei 6-151445.

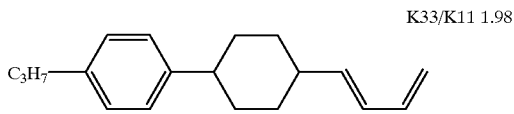

However, since the substituent, 1,3-butadienyl group has a conjugated diene moiety, the compound is chemically very unstable, and thus it was impossible to use the compound in liquid crystal compositions to be practically used.

In short, liquid crystalline compounds are long-awaited which have a large elastic constant ratio $K_{33}/K_{11}$, still lower viscosity compared with that of known liquid crystalline compounds, high chemical stability, and excellent miscibility with other liquid crystalline compounds.

DISCLOSURE OF THE INVENTION

An object of the present invention is to provide a novel liquid crystalline compound which has a large ratio of elastic constants, has a low viscosity compared with that of known liquid crystalline compounds, is excellent in miscibility with other liquid crystalline compounds, particularly in the miscibility at low temperatures, and is chemically stable, and to provide a liquid crystal composition containing the compound. As a result of the diligent investigation by the present inventors to solve the problems mentioned above, compounds have been found which have a novel structure and have improved characteristics compared with those of known liquid crystalline compounds, leading to the achievement of the present invention.

First aspect of the present invention is concerned with a liquid crystalline compound having an unconjugated alkadienyl group at a side chain.

Second aspect of the present invention is concerned with a liquid crystalline compound expressed by general formula (1)

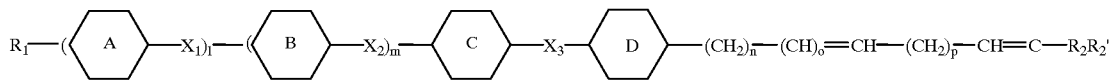

wherein $R_1$ represents cyano group, halogen atom, or a straight or branched alkyl group or halogenated alkyl group having 1 to 20 carbon atoms, one or not-adjacent two $CH_2$ groups in the alkyl group or halogenated alkyl group may be replaced by oxygen atom or —CH═CH— group; $R_2$ and $R_2'$ represent hydrogen atom, halogen atom, or an alkyl group having 1 to 9 carbon atoms; $X_1$, $X_2$, and $X_3$ independently represent —$CH_2CH_2$—, —CO—O—, —O—CO—, —CH═CH—, —C≡C—, —$(CH_2)_4$—, —$CF_2O$—, —$OCF_2$—, —$CH_2O$—, —$OCH_2$—, or a covalent bond; rings A, B, C, and D are independently represent 1,4-phenylene ring, trans-1,4-cyclohexylene ring, bicyclo[1,1,0]butane ring, bicyclo[1,1,1]pentane ring, bicyclo[3,2,2]octane ring, cyclobutane ring, or spiro[3,3]heptane ring, respectively, hydrogen atom in these rings may be replaced by halogen atom, carbon atom in these rings may be replaced by nitrogen atom or oxygen atom; l, m, and o are independently 0 or 1, n is an integer of 0 to 3, p is an integer of 1 to 5.

Third aspect of the present invention is concerned with a second compound of the present invention expressed by general formula (1) wherein n is 0, o is 1, p is 2, and $R_2$ and $R_2'$ are hydrogen atom, respectively.

Fourth aspect of the present invention is concerned with a third compound of the present invention expressed by general formula (1) wherein at least one of $X_1$, $X_2$, and $X_3$ is a covalent bond.

Fifth aspect of the present invention is concerned with a fourth compound of the present invention expressed by general formula (1) wherein $X_1$, $X_2$, and $X_3$ are —$CH_2CH_2$—, —CH═CH—, —$(CH_2)_4$—, or a covalent bond.

Sixth aspect of the present invention is concerned with a liquid crystal composition comprising at least two components and containing a compound recited in any one of the aspects 1 to 5 in at least one of the components.

Seventh aspect of the present invention is concerned with a liquid crystal composition containing, as a first component, at least one compound recited in any one of the aspects 1 to 5, and containing, as a second component, one or more compounds selected from the group consisting of the compounds expressed by general formula (2), (3), or (4)

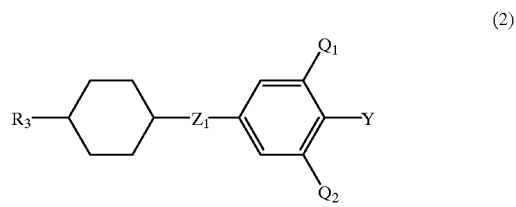

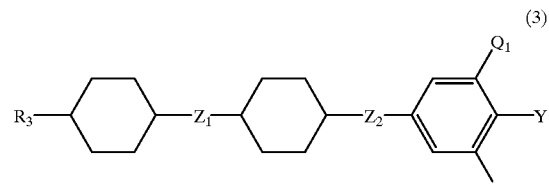

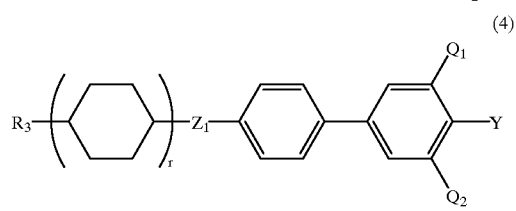

in which $R_3$ represents an alkyl group having 1 to 10 carbon atoms, Y represents F or Cl, $Q_1$ and $Q_2$ independently represent H or F, r is 1 or 2, and $Z_1$ and $Z_2$ independently represent —$CH_2CH_2$— or a covalent bond.

Eighth aspect of the present invention is concerned with a liquid crystal composition containing, as a first component, at least one compound recited in any one of the aspects 1 to 5, and containing, as a second component, one or more compounds selected from the group consisting of the compounds expressed by general formula (5), (6), (7), (8), or (9)

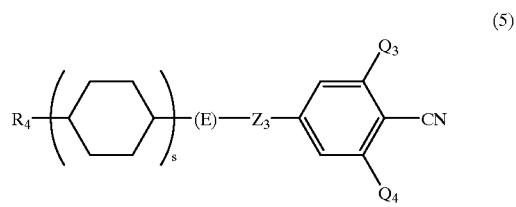

in which $R_4$ represents an alkyl group having 1 to 10 carbon atoms or an alkenyl group having 2 to 10 carbon atoms, in either case any methylene group (—$CH_2$—) in the alkyl or alkenyl group may be replaced by oxygen atom (—O—) provided that in no case two or more methylene groups are continuously replaced by oxygen atom; $Z_3$ represents —$CH_2CH_2$—, —COO—, or a covalent bond, $Q_3$ and $Q_4$ represent H or F, E represents cyclohexane ring, benzene ring, or 1,3-dioxane ring, and s is an integer of 0 or 1,

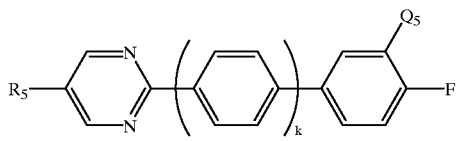
(6)

in which $R_5$ represents an alkyl group having 1 to 10 carbon atoms, $Q_5$ represents H or F, and k is an integer of 0 or 1,

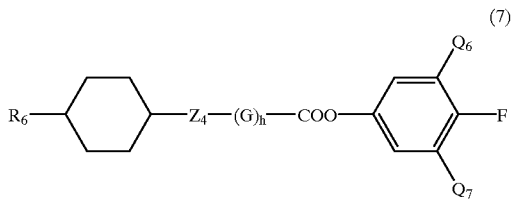
(7)

in which $R_6$ represents an alkyl group having 1 to 10 carbon atoms, G represents cyclohexane ring or benzene ring, $Q_6$ and $Q_7$ independently represent H or F, respectively, $Z_4$ represents —COO— or a covalent bond, and h is an integer of 0 or 1,

(8)

in which $R_7$ and $R_8$ independently represent an alkyl group, alkyloxyl group, or alkyloxymethyl group having 1 to 10 carbon atoms, H represents cyclohexane ring, pyrimidine ring, or benzene ring, J represents cyclohexane ring or benzene ring, $Z_5$ represents —C≡C—, —COO—, —CH$_2$CH$_2$—, or a covalent bond,

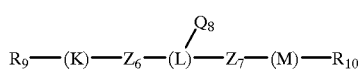
(9)

in which $R_9$ represents an alkyl group or alkoxyl group having 1 to 10 carbon atoms, $R_{10}$ represents an alkyl group, alkyloxyl group, or alkoxymethyl group having 1 to 10 carbon atoms, K represents cyclohexane ring or pyrimidine ring, each of L and M independently represent cyclohexane ring or benzene ring, $Z_6$ represents —COO—, —CH$_2$CH$_2$—, or a covalent bond, $Z_7$ represents —C≡C—, —COO—, or a covalent bond, and $Q_8$ represents H or F. Ninth aspect of the present invention is concerned with a liquid crystal display device comprising a liquid crystal composition recited in any one of the aspects 6 to 8.

Tenth aspect of the present invention is concerned with a liquid crystal display device comprising a liquid crystal composition recited in any one of the aspects 6 to 9.

Preferable compounds of the present invention recited in the aspects 1 to 5 are those expressed by the group of the following general formulas (1-a) to (1-c). However, W in the following formulas represents —(CH$_2$)$_n$—(CH)$_o$=CH—(CH$_2$)p—CH=CH—R$_2$R$_2$' in general formula (1), and R$_1$, R$_2$, R$_2$', X$_1$, X$_2$, X$_3$, rings A, B, C, and D, and l, m, n, o, and p have the same meaning as mentioned above.

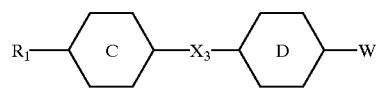
(1-a)

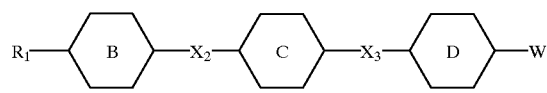
(1-b)

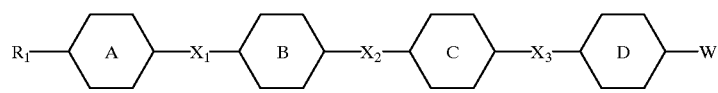
(1-c)

Further, among the compounds expressed by the group of general formulas (1-a) to (1-c), particularly preferable compounds are shown below:

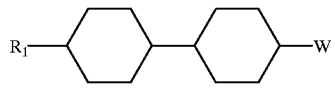

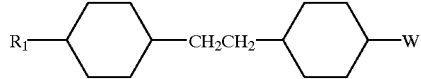

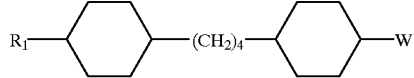

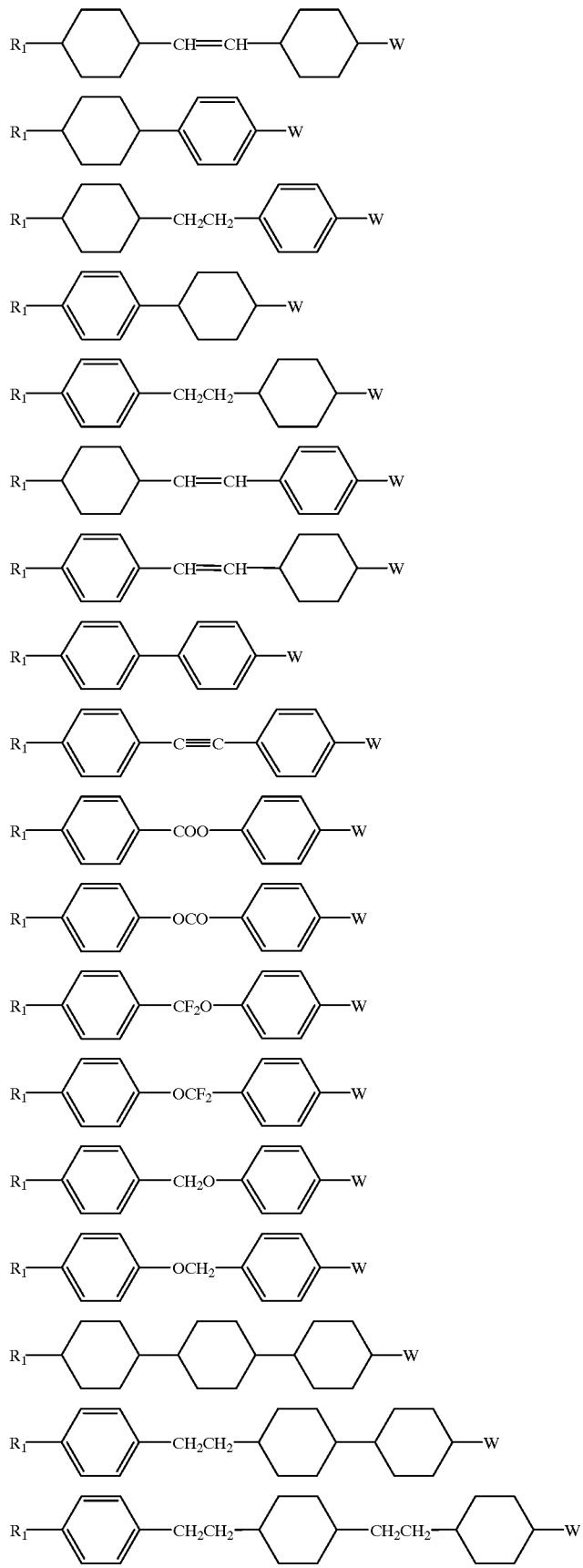

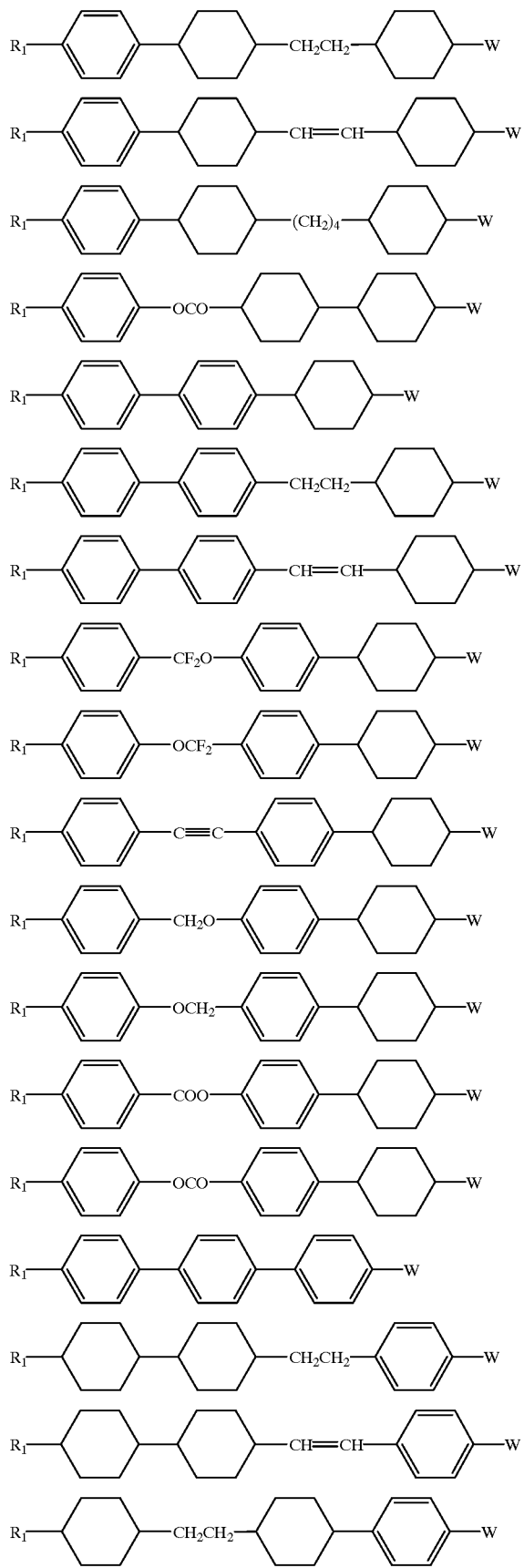

-continued
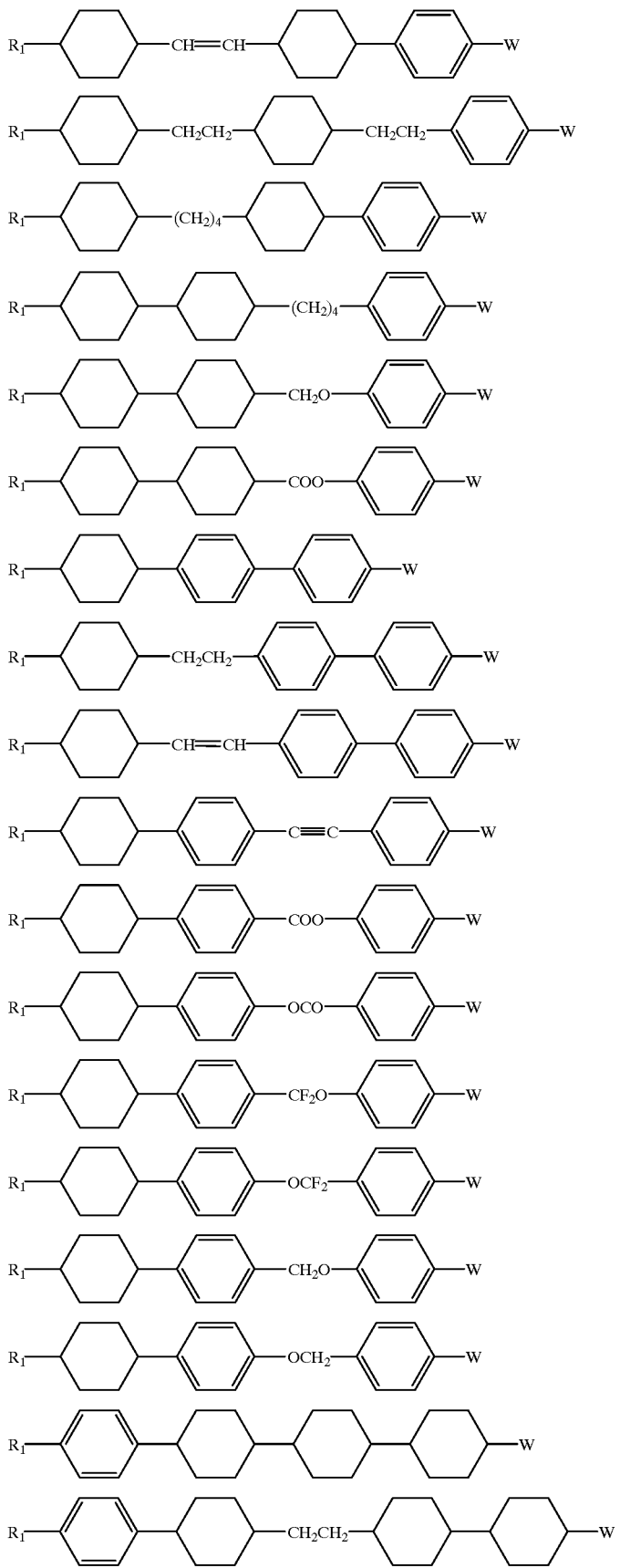

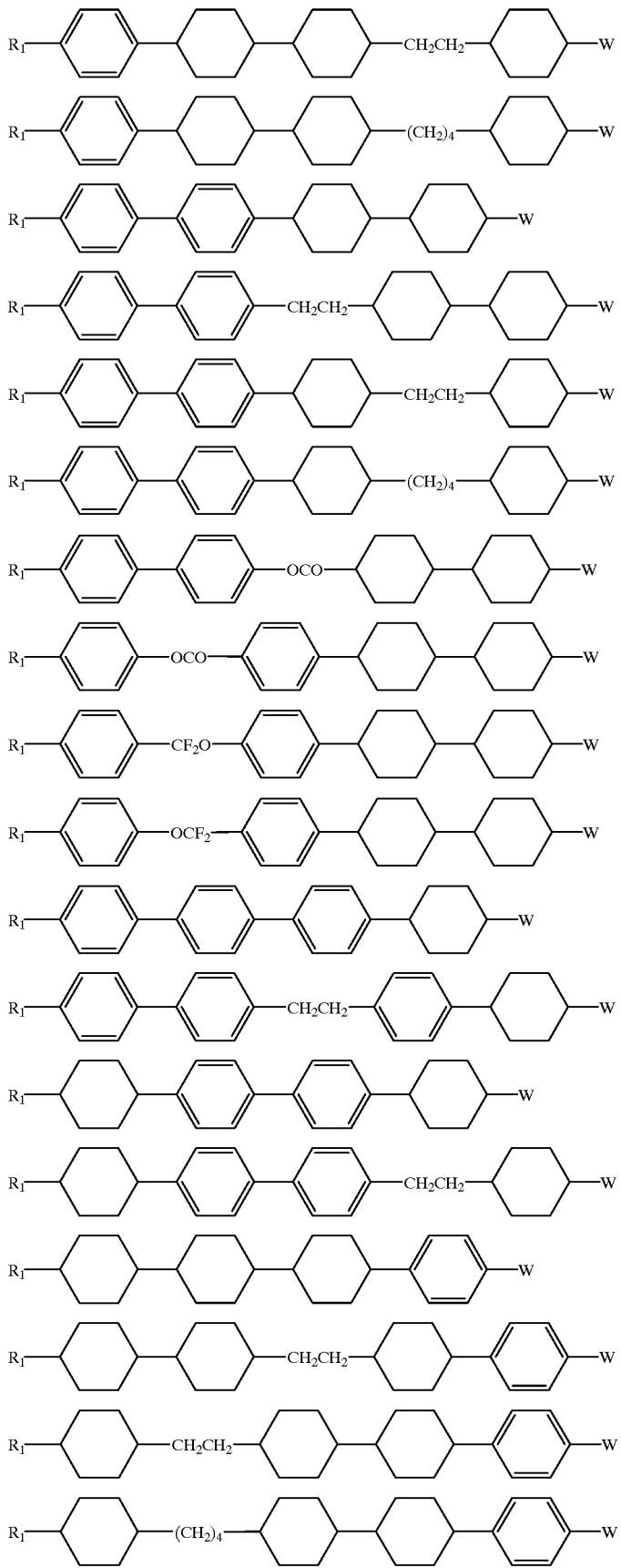

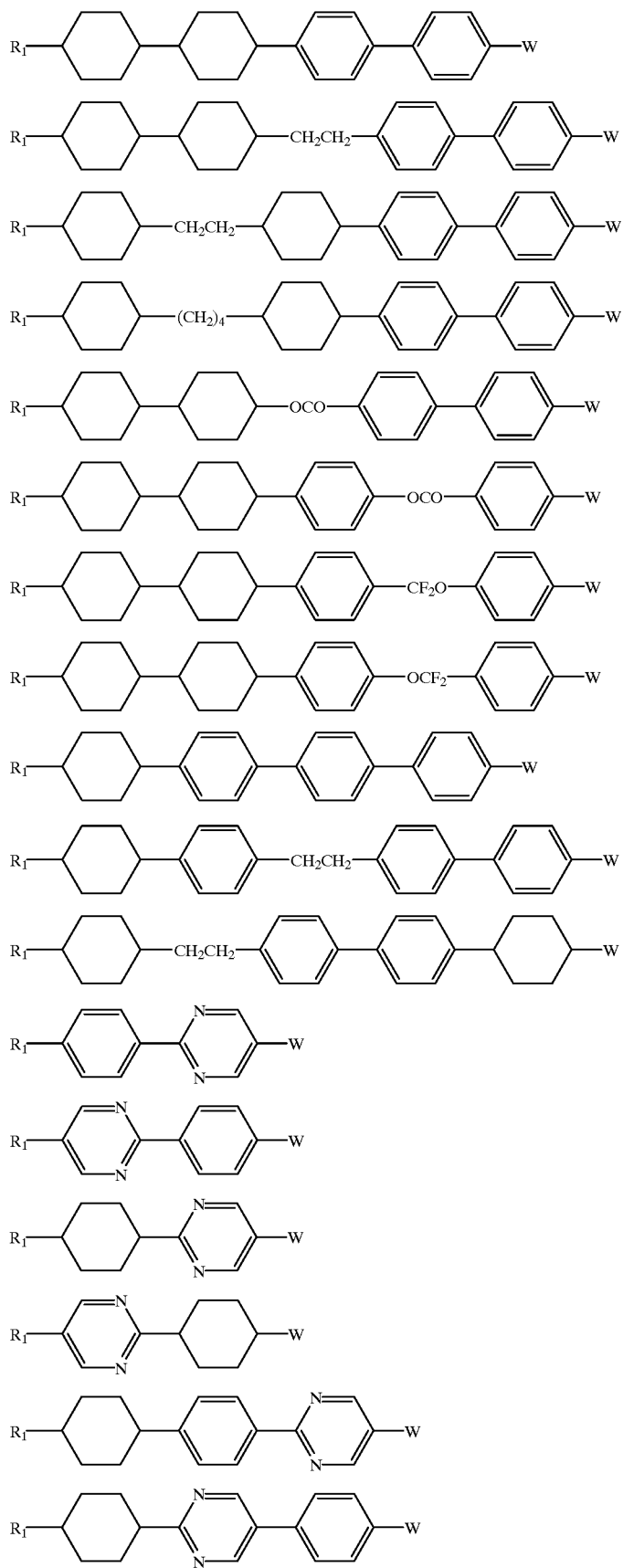

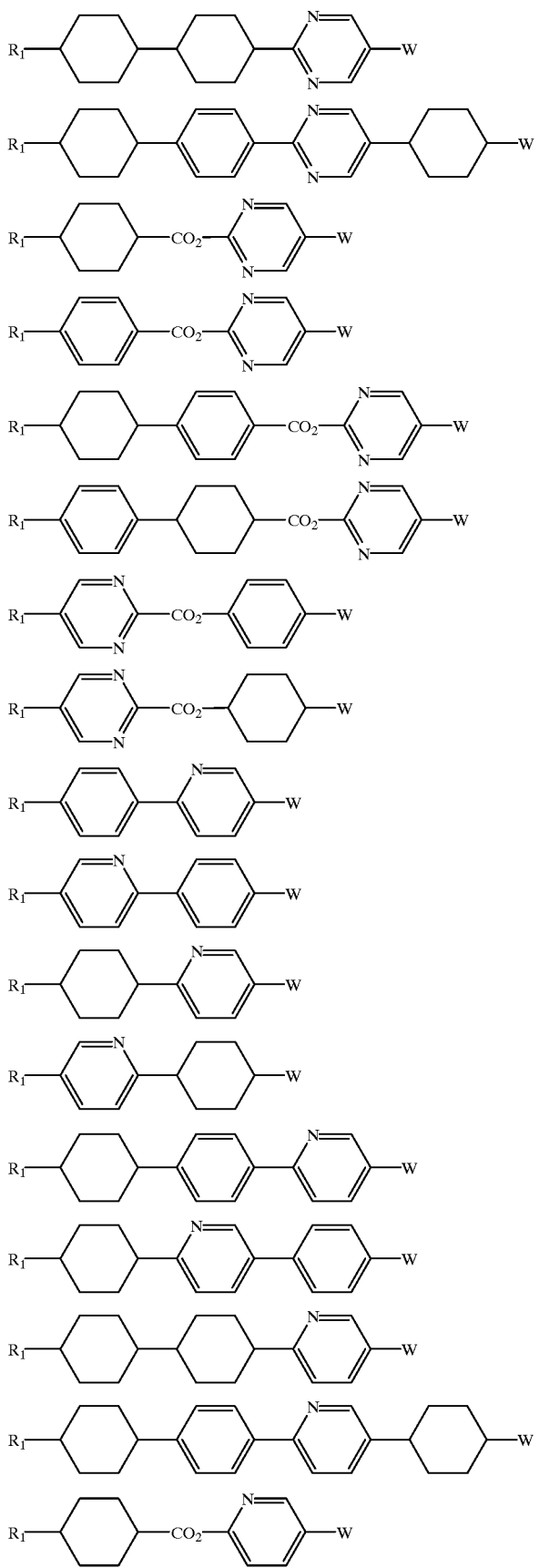

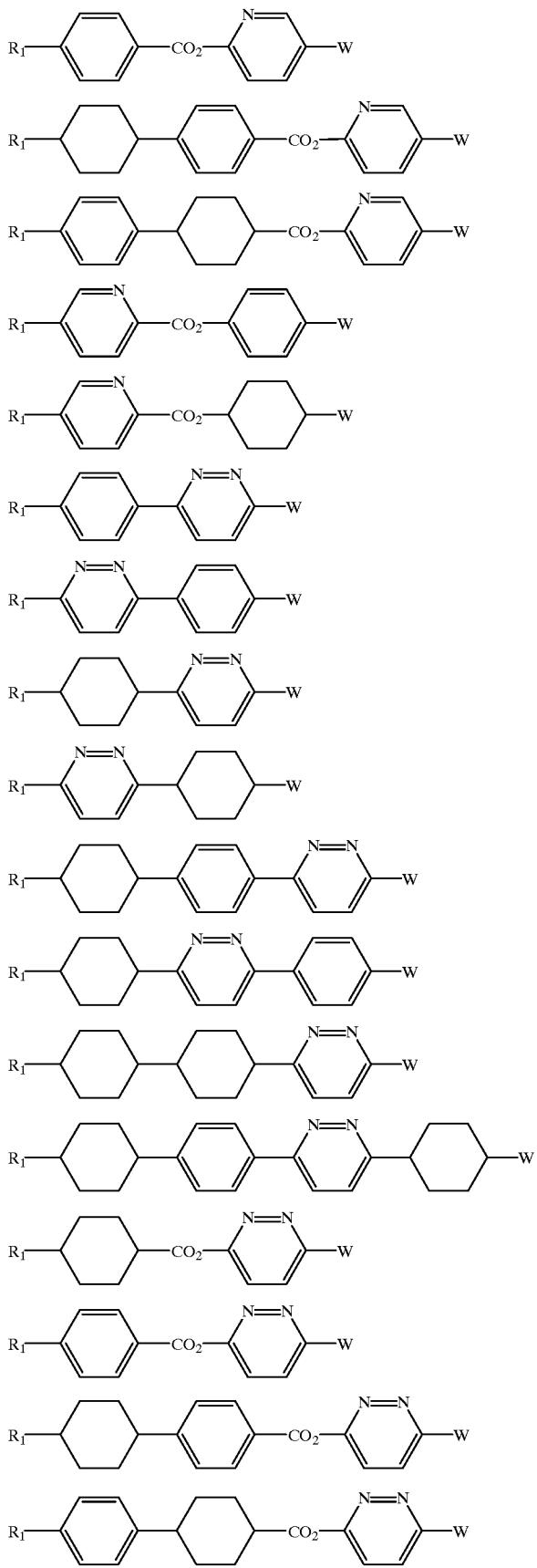

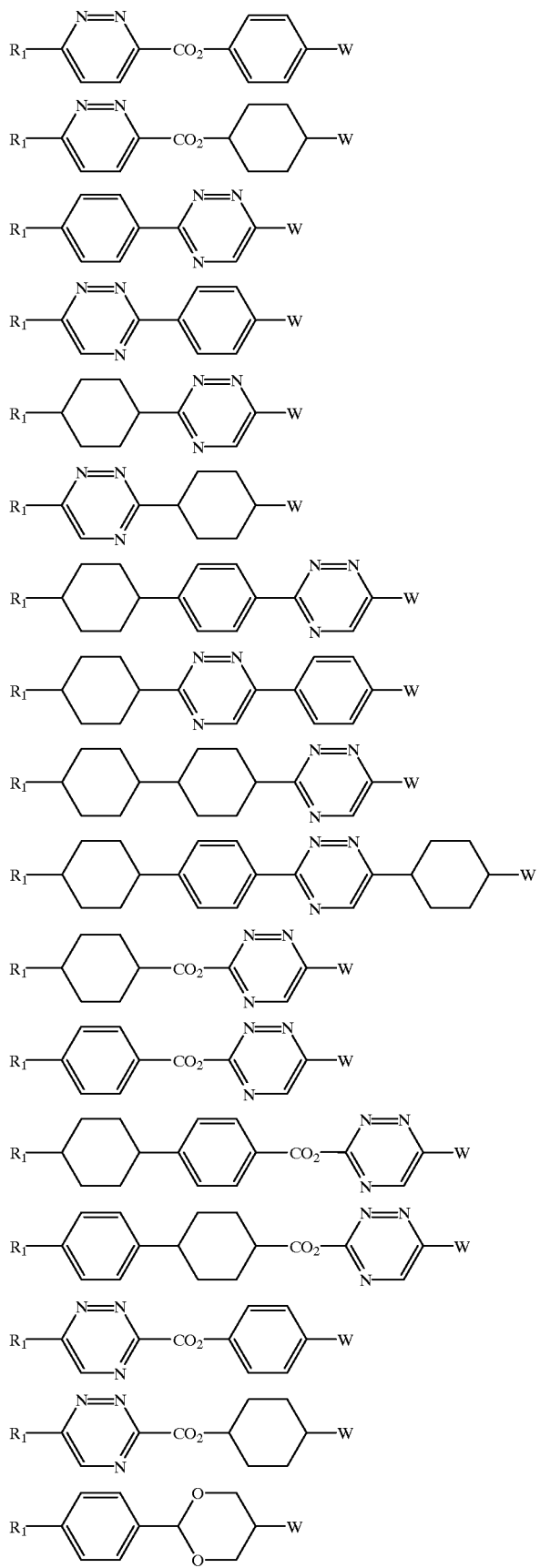

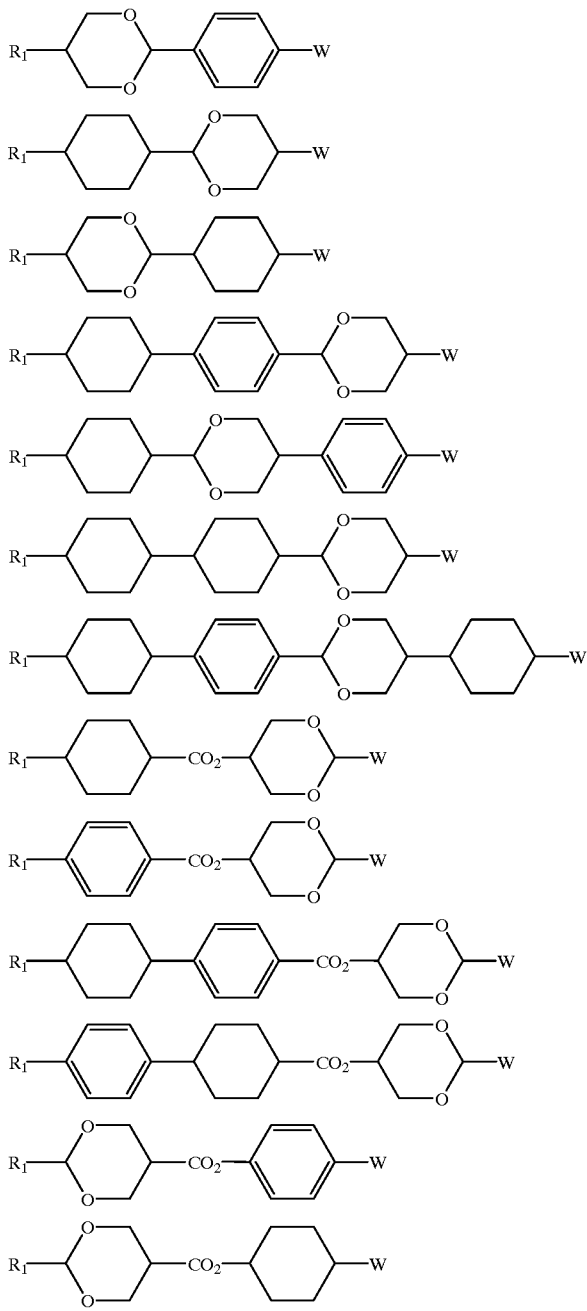

whereas $R_1$ and W in the formulas shown above have the same meaning as that mentioned above, hydrogen atom in 1,4-phenylene ring, trans-1,4-cyclohexylene ring, bicyclo[1,1,0]butane ring, bicyclo[1,1,1] pentane ring, bicyclo[3,2,2] octane ring, cyclobutane ring, and spiro[3,3]heptane ring may be replaced by halogen atom, and the carbon atom in the rings may be replaced by nitrogen atom or oxygen atom.

While any of dienyl group W exhibits preferable characteristics when it satisfies the conditions shown by general formula (1), particularly preferable ones are $W_1$ to $W_{15}$, $W_{17}$, and $W_{19}$, and more desirable ones are $W_1$ to $W_8$, and $W_{17}$ shown below:

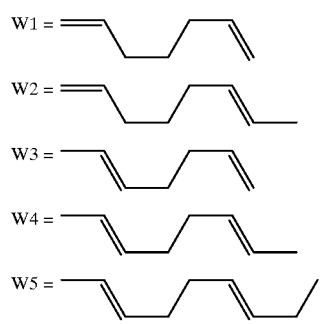

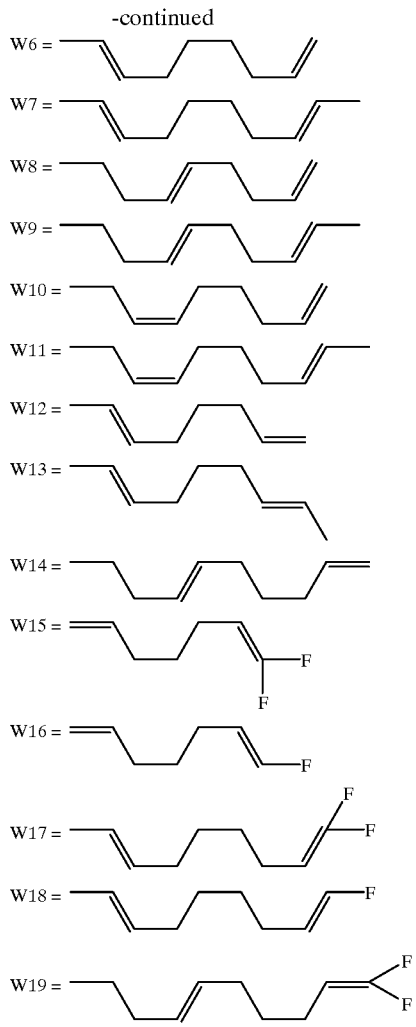

While $R_1$ in the formulas shown above represents cyano group, halogen atom, or a straight or branched alkyl group or halogenated alkyl group having 1 to 20 carbon atoms, methylene group in the alkyl or halogenated alkyl group may be replaced by oxygen atom or —CH=CH—. As the halogen atom, fluorine atom and chlorine atom, and as the alkyl group, one having 1 to 10 carbon atoms, particularly 1 to 6 carbon atoms is preferable. Further, as the halogenated alkyl group, trifluoromethyl, trifluoromethoxy, difluoromethoxy, 2-fluoroethyl, 2,2-difluoroethyl, 2,2,2-trifluoroethyl, 3-fluoropropyl, 2-fluoro-propyl, 2,2-difluoropropyl, 4-fluorobutyl, 3-fluorobutyl, 2-fluorobutyl, 3,3-difluorobutyl, 2,2-difluorobutyl, 5-fluoropentyl, 4-fluoropentyl, 3-fluoropentyl, 3,3-difluoropentyl, and 10-fluorodecyl are preferable. As the one in which methylene group is replaced by oxygen atom, methoxymethyl, ethoxymethyl, propoxymethyl, butoxymethyl, pentoxymethyl, methoxyethoxy, methoxypropyl, ethoxyethoxy, and ethoxypropoxyl group are preferable. As the one in which methylene group is replaced by —CH=CH—, vinyl, 1-propenyl, 2-propenyl, 1-butenyl, 3-butenyl, 1-pentenyl, 2-pentenyl, and 3-pentenyl group are preferable.

Any of the compounds of the present invention expressed by general formula (1) has a large elastic constant ratio $K_{33}/K_{11}$ and a low viscosity. Further, any of them is an unconjugated diene and chemically very stable.

Any of the compounds of the present invention exhibits preferable physical properties, and liquid crystal compositions which have characteristics satisfying the purpose can be produced by using compounds expressed by general formula (1) and in which $R_1$, $R_2$, $R_2'$, $X_1$, $X_2$, $X_3$, A, B, C, D, l, m, n, o, and p are suitably selected. For instance, when a compound is used for a liquid crystal composition mesomorphic range of which must be particularly in a high temperature side, a tricyclic or tetracyclic compound can be used, and in other cases, bicyclic or tricyclic compound can be used.

When especially a large dielectric anisotropy is required, a compound having a positive dielectric anisotropy (P type compound) is used as in the case for compositions commonly used, and a P type compound can be provided by selecting halogen atom or cyano group as $R_1$ in general formula (1). Besides, when a still larger dielectric anisotropy is required, the purpose is achieved by introducing halogen atom on a ring to which $R_1$ is linked. In order to obtain a compound having a negative dielectric anisotropy (N type compound), it will be sufficient to introduce a substituent having a not-large dipole moment, for example, an alkyl group as $R_1$.

Optical anisotropy can also be controlled by optionally selecting $R_1$, $R_2$, $R_2'$, $X_1$, $X_2$, $X_3$, A, B, C, D, l, m, n, o, and p in general formula (1). That is, when a large optical anisotropy is required, it is sufficient to use a compound having more 1,4-phenylene rings; and a compound having a more trans-1,4-cyclohexylene rings when a small optical anisotropy is required.

Compounds of the present invention expressed by general formula (1) can readily be produced by freely using the ordinary technique in organic synthetic chemistry as indicated by the reaction formulas shown below:

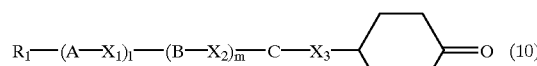

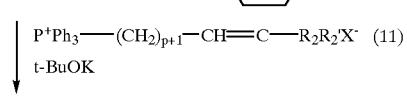

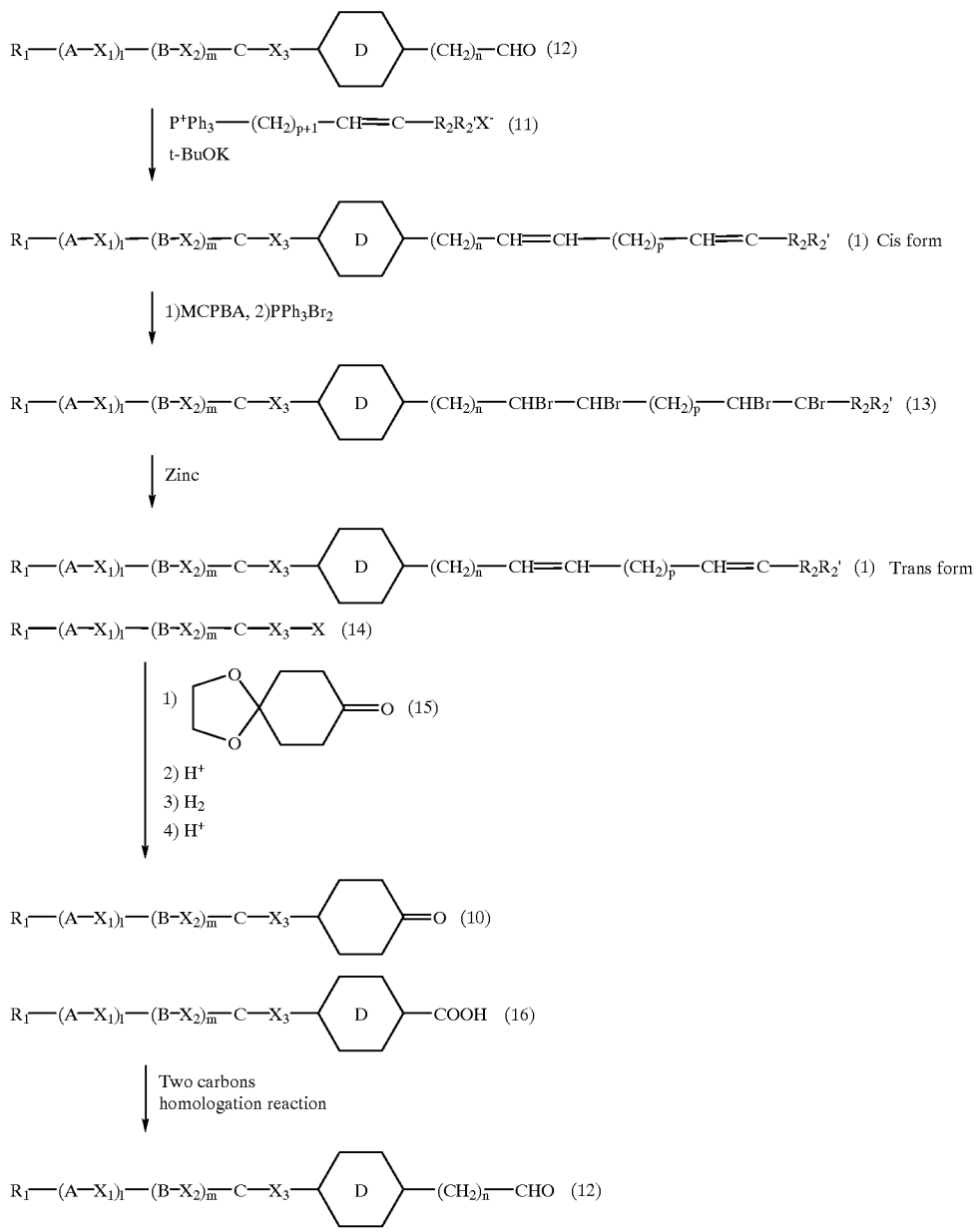

in the formula shown above, ring D represents a substituted or unsubstituted 1,4-phenylene ring or trans-1,4-cyclohexylene ring, hydrogen atom in the ring may be replaced by halogen atom, and the carbon atom in the ring may be replaced by nitrogen atom or oxygen atom, and X represents halogen atom.

That is, when o and n are 0, the compound expressed by general formula (1) can be produced by reacting a phosphonium salt such as (11) with a cyclohexanone (10) in the presence of a base. The phosphonium salt can readily be produced from a corresponding halide and triphenylphosphine according to the method of G. Wittig et al. described in Org. Synth. Col. V. 751 (1973). As the base, for example, alkyl lithium, sodium hydride, and potassium-t-butoxide can preferably be used.

When o is 1, (1) can be obtained by reacting (11) with an aldehyde expressed by (12) according to the method of G. Wittig et al. described in Org. Synth. Col. V. 751 (1973).

Whereas the reaction of (11) with (12) usually gives a cis form olefin as main product, it can be derived to (1) which is in trans form by converting the olefin into a bromide (13), removing unnecessary isomers by recrystallization, and then reducing the bromide according to the method of J. Schaeffer et al. described in Org. Synth. Col. V. 249 (1973). While the method in which the olefin is once oxidized to form an epoxide and then reacted with triphenylphosphine dibromide is preferable for the bromination, there is no problem in directly reacting bromine of simple substance with an olefin. While the reduction of (13) can readily be performed by either method, the use of metal zinc according to the method of S. J. Cristol et al. described in J. Am. Chem. Soc., 89, 401 (1967) is preferable.

Cyclohexanone (10) can readily be produced from, for example, a halide (14). That is, (10) can be preferably produced by converting (14) into Grignard reagent or lithium reagent, reacting it with an available cyclohexanone derivative (15), and then subjecting to a dehydration, reduction, and deprotection.

Also, aldehyde (12) can be produced from a carboxylic acid (16), which can be obtained by a method described in literatures, for example, the method of M. E. Neubert et al. described in Mol. Cryst. Liq. Cryst., 76, 48 (1981), by utilizing a two carbons homologation reaction ordinarily used.

When $X_1$, $X_2$, and $X_3$ in general formula (1) are —$CH_2CH_2$—, main skeleton can be constructed according to the method of Laid-open Japanese Patent Publication No. Hei 5-140015 and when they are —$(CH_2)_4$—, can be constructed according to the method of Laid-open Japanese Patent Publication No. Hei 5-310605. When they are —CH=CH— or —C≡C—, it can be produced by the method of Laid-open Japanese Patent Publication No. Hei 6-92924 and C. E. Castro et al. described in Org. Chem., 28, 2163, 3313 (1963), respectively. When they are —$CF_2O$— or —$OCF_2$—, it can be produced according to the method of Laid-open Japanese Patent Publication No. Hei 5-112778, and when they are —$CH_2O$— or —$OCH_2$—, it can be produced according to the method of Japanese Patent Publication No. Hei 2-6743. Also, when they are —COO— or —OCO—, it can preferably be produced according to the method of B. K. Sadashiva, Mol. Cryst. Liq. Cryst., 55, 135 (1979).

Liquid crystal composition of the present invention preferably contains at least one compound expressed by general formula (1) in a ratio of 0.1 to 99% by weight to develop excellent characteristics.

Specifically, liquid crystal compositions of the present invention can be produced by blending a compound optionally selected, depending on the purpose, from the group of compounds expressed by any one of general formulas (2) to (9) to the first component containing at least one compound expressed by general. formula (1).

As the compounds used in liquid crystal compositions of the present invention and expressed by any one of general formulas (2) to (4), the following compounds can preferably be mentioned: (In the followings, Ra represents an alkyl group or alkoxy group.)

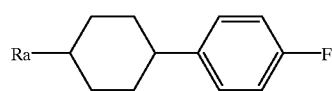
(2-1)

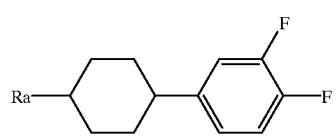
(2-2)

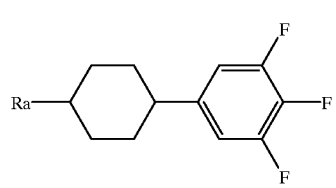
(2-3)

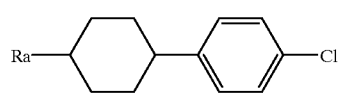
(2-4)

-continued

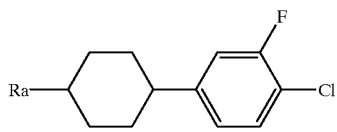
(2-5)

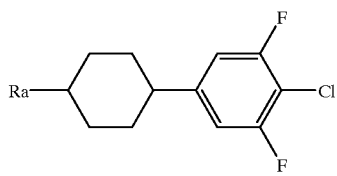
(2-6)

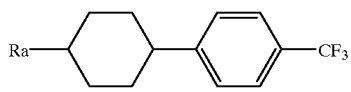
(2-7)

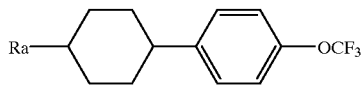
(2-8)

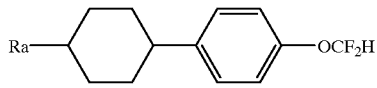
(2-9)

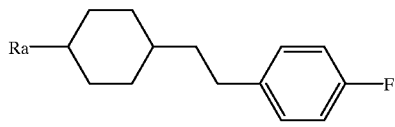
(2-10)

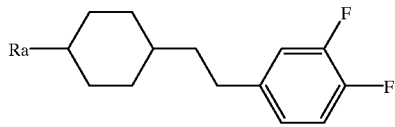
(2-11)

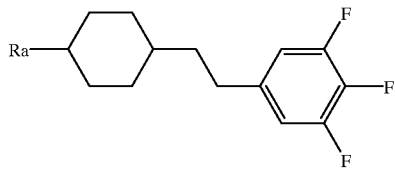
(2-12)

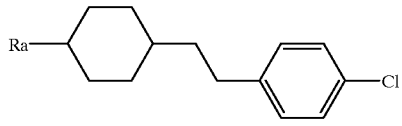
(2-13)

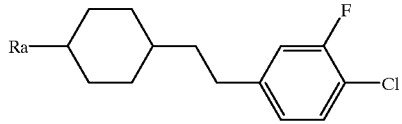
(2-14)

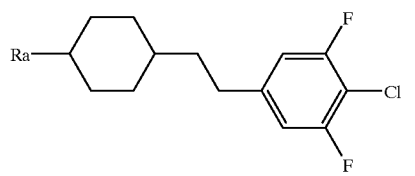 (2-15)
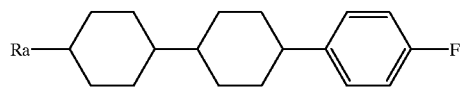 (3-1)
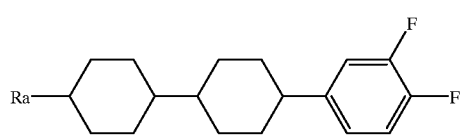 (3-2)
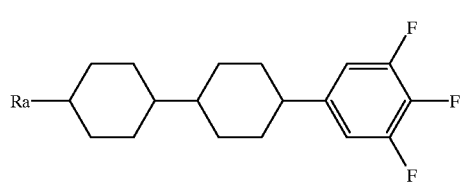 (3-3)
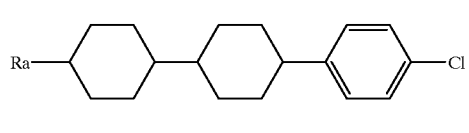 (3-4)
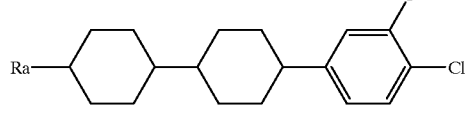 (3-5)
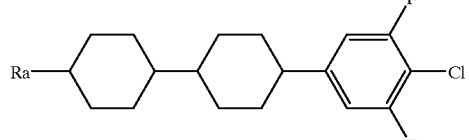 (3-6)
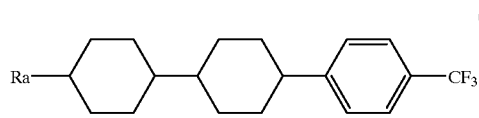 (3-7)
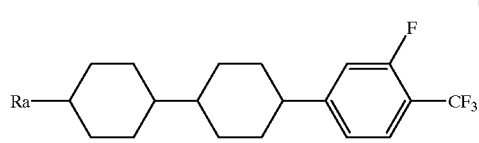 (3-8)
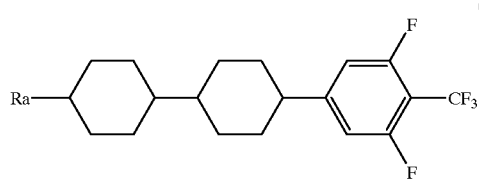 (3-9)
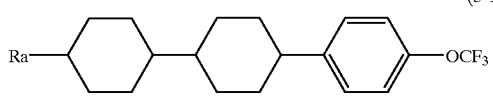 (3-10)
 (3-11)
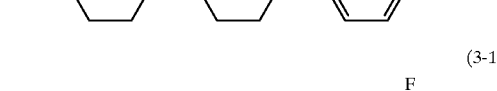 (3-12)
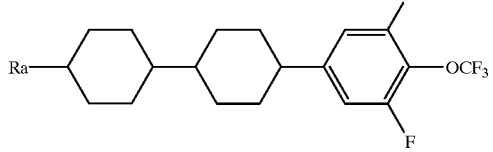 (3-13)
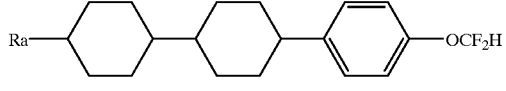 (3-14)
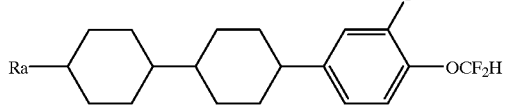 (3-15)
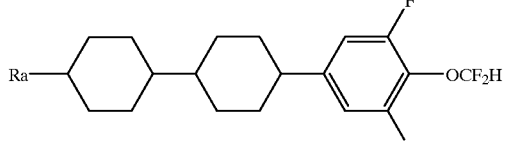 (3-16)
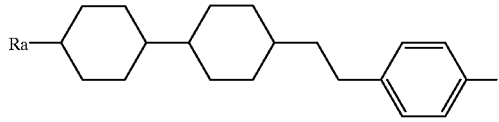 (3-17)
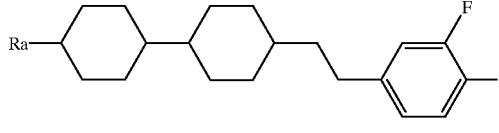 (3-18)
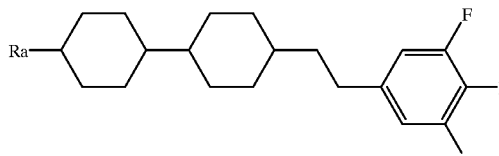

(3-19)
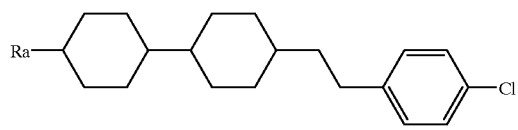
(3-20)
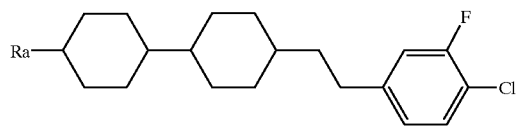
(3-21)
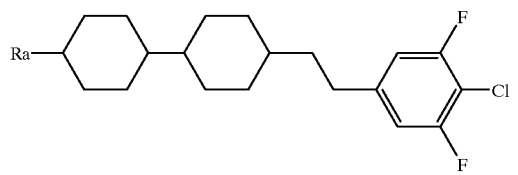
(3-22)
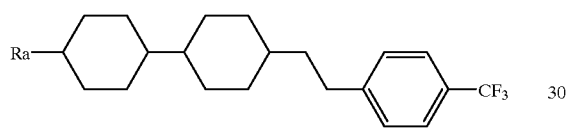
(3-23)
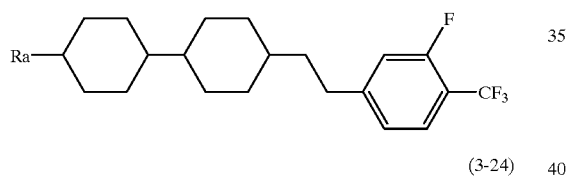
(3-24)
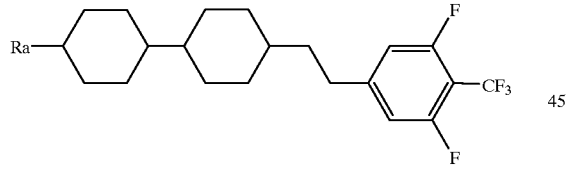
(3-25)
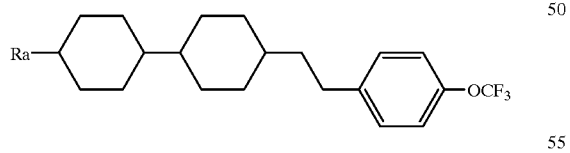
(3-26)
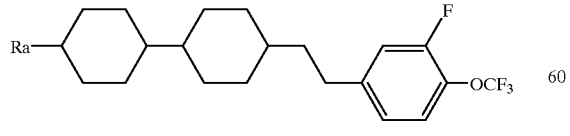
(3-27)
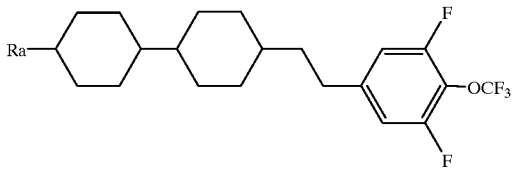
(3-28)
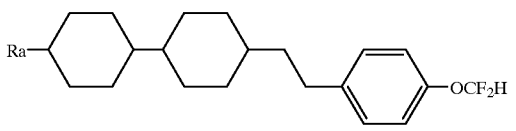
(3-29)
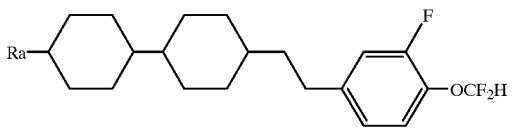
(3-30)
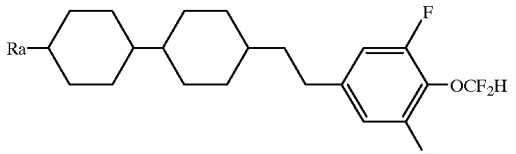
(3-31)
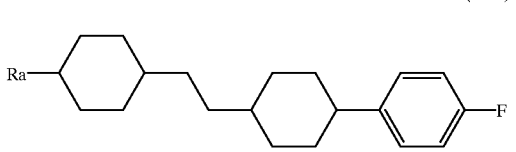
(3-32)
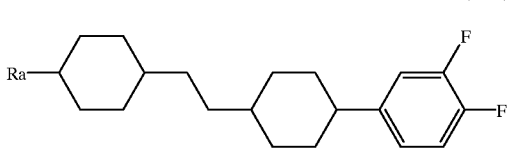
(3-33)
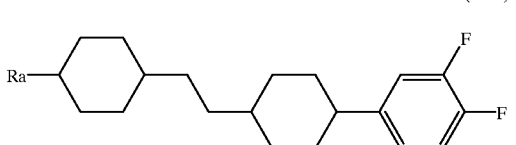
(3-34)
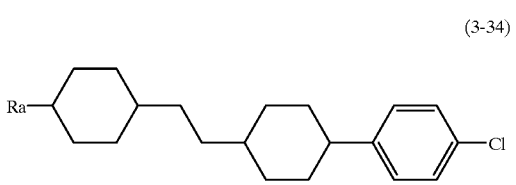

(3-35)
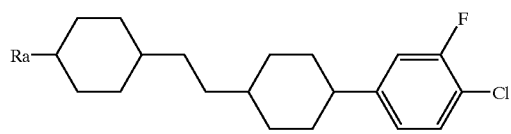
(3-36)
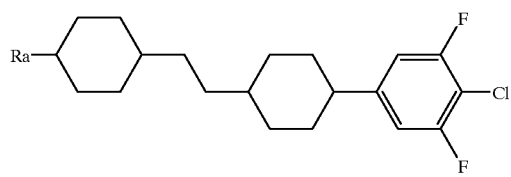
(3-37)
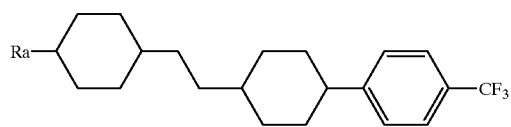
(3-38)
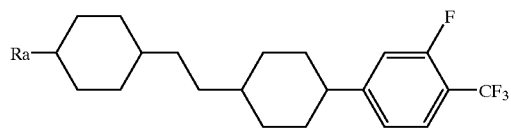
(3-39)
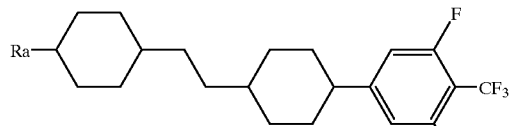
(3-40)
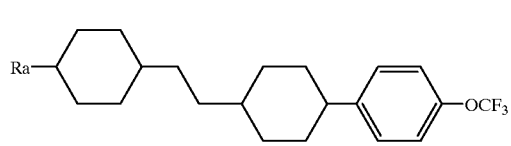
(3-41)
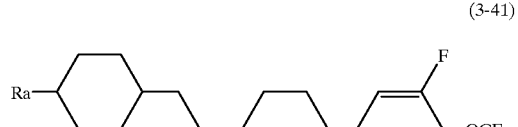
(3-42)
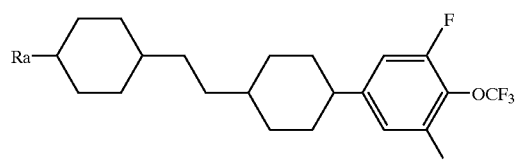
(3-43)
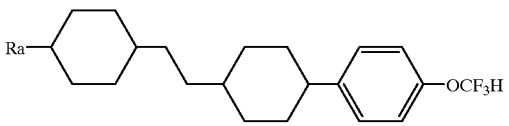
(3-44)
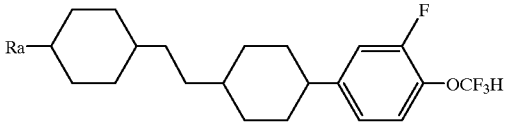
(3-45)
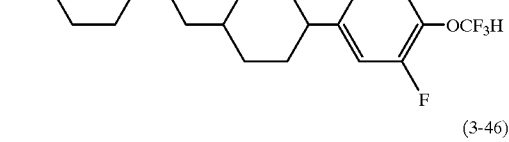
(3-46)
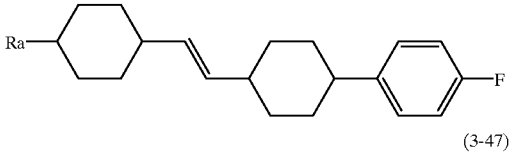
(3-47)
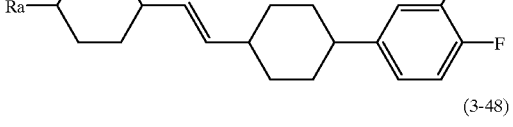
(3-48)
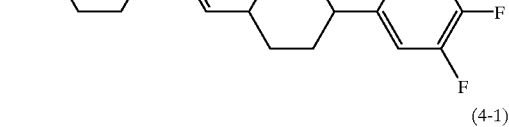
(4-1)
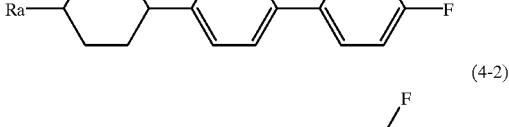
(4-2)
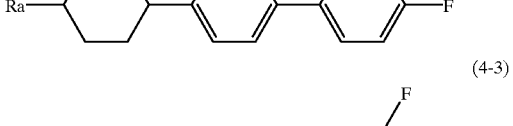
(4-3)
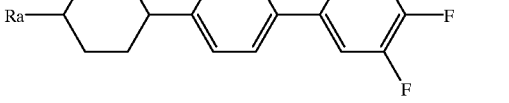

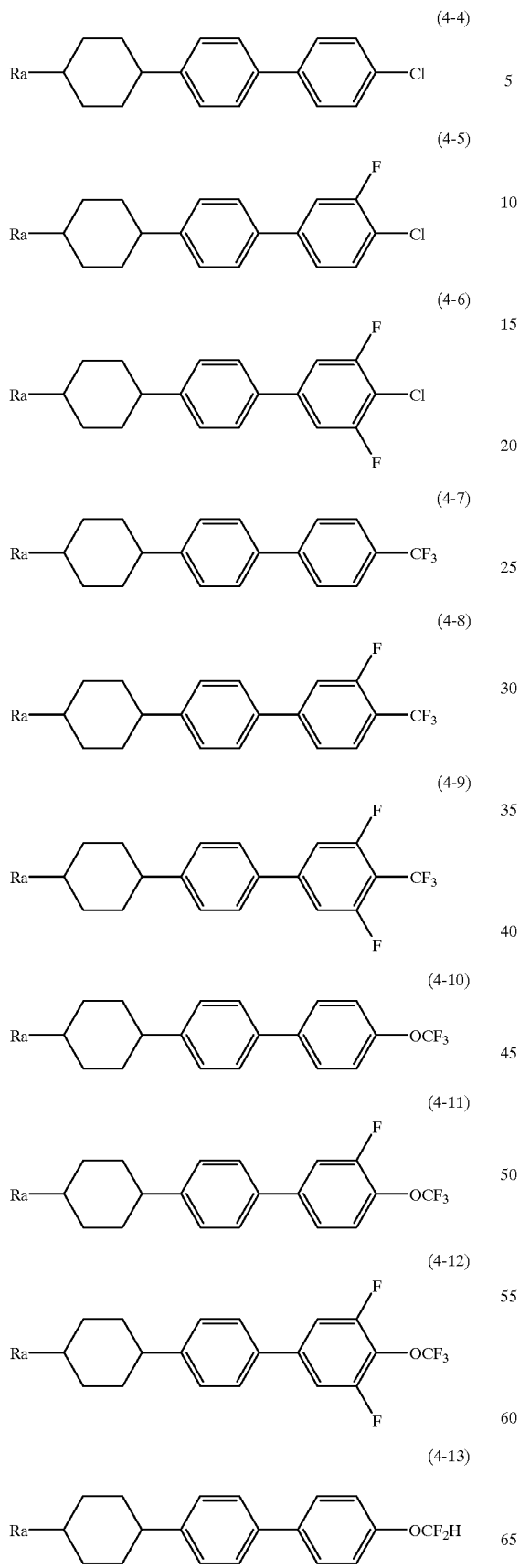
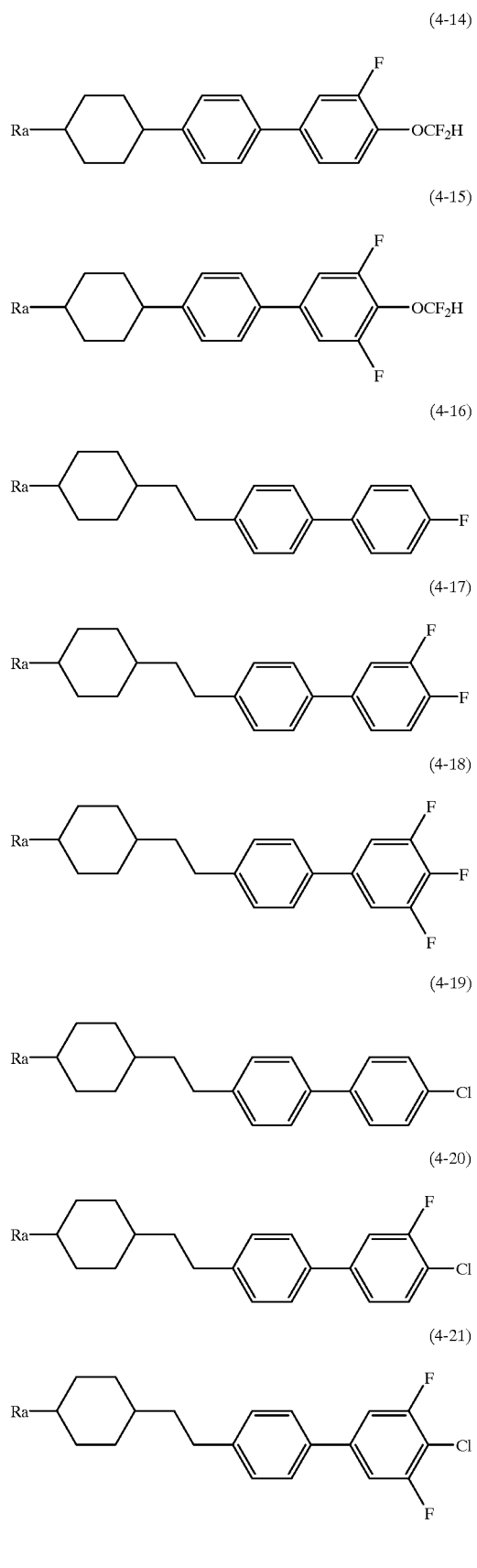

(4-22)
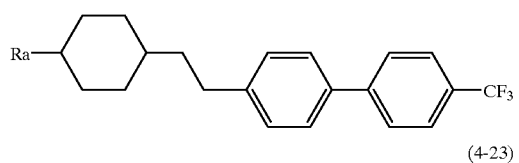
(4-23)
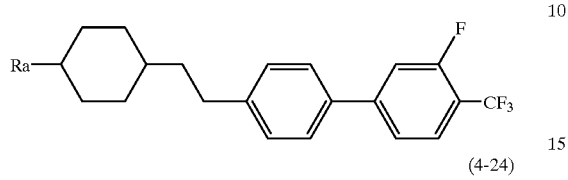
(4-24)
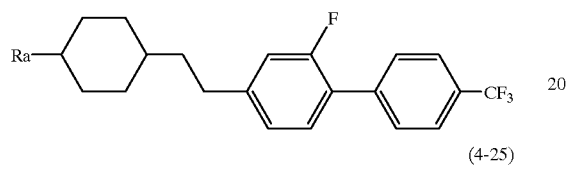
(4-25)
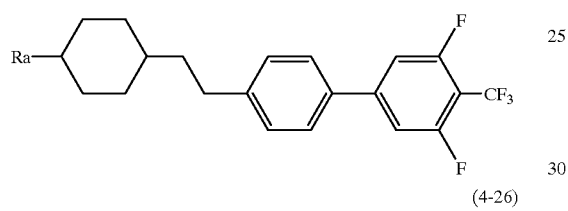
(4-26)
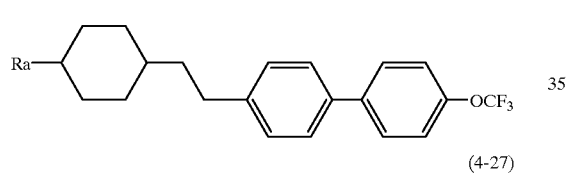
(4-27)
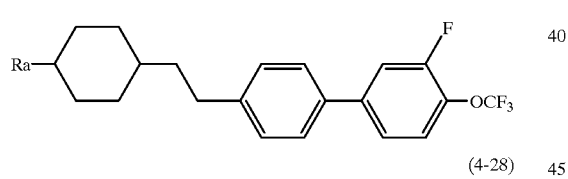
(4-28)
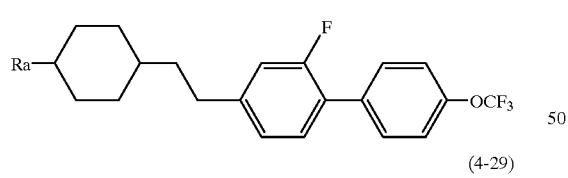
(4-29)
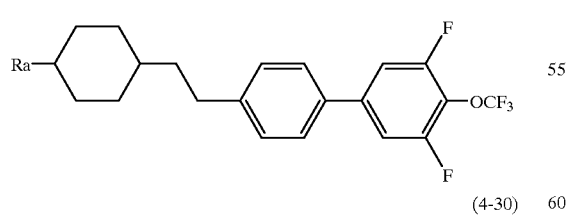
(4-30)
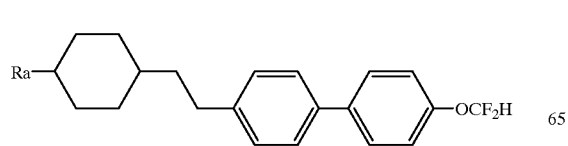
(4-31)
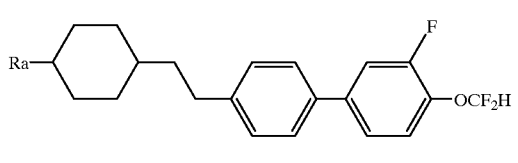
(4-32)
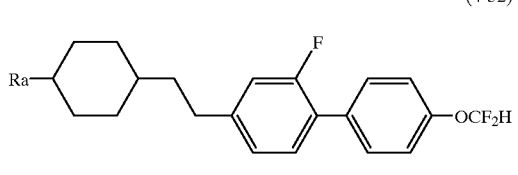
(4-33)
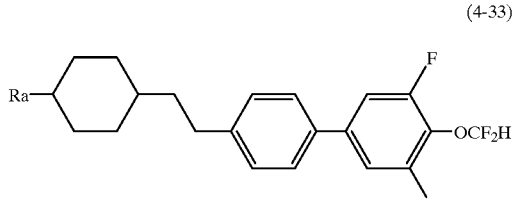
(4-34)
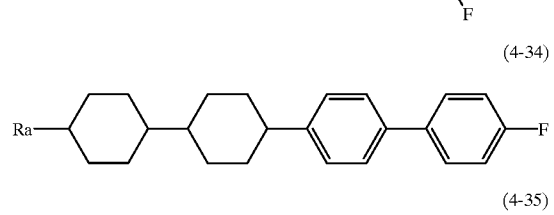
(4-35)
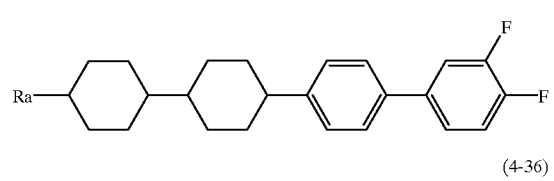
(4-36)
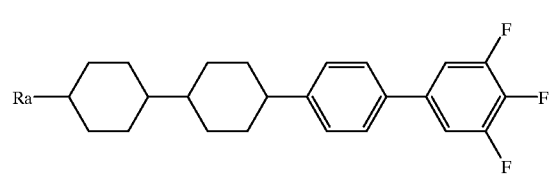
(4-37)
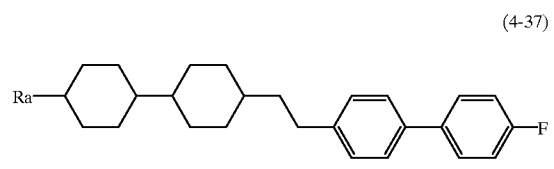
(4-38)
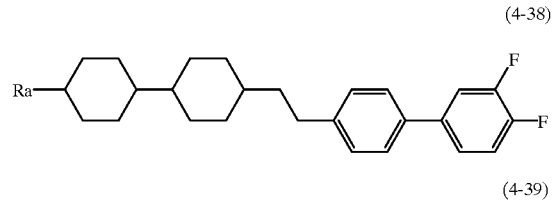
(4-39)
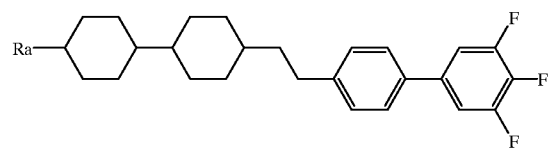

(4-40)

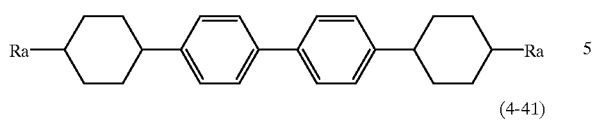

(4-41)

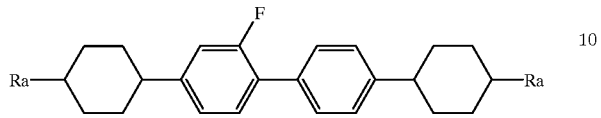

Compounds expressed by any one of general formulas (2) to (4) are ones which have a positive dielectric anisotropy, are remarkably excellent in heat resistance and chemical resistance, and are indispensable compounds when liquid crystal compositions for TFT (AM-LCD) are produced of which TFT high reliability demonstrated, for instance, by an especially high voltage holding ratio and a large specific resistance is required.

While the compounds expressed by any one of general formulas (2) to (4) can optionally be used in the range of 1 to 99% by weight based on the total amount of liquid crystal composition when liquid crystal compositions for TFT are produced, the use in an amount of 10 to 97% by weight is preferable and 40 to 95% by weight is more desirable. Also at that time, a compound expressed by any one of general formulas (5) to (9) may be contained as a part of the composition. Even when liquid crystal compositions for STN display mode or ordinary TN display mode are produced, a compound expressed by any one of general formulas (2) to (4) can be used.

As the compounds expressed by any one of general formulas (5) to (7), the following compounds can preferably mentioned: (In the followings, Rb, Rc, and Rd represent an alkyl group or alkenyl group, and R' represents an alkylene.)

(5-1)

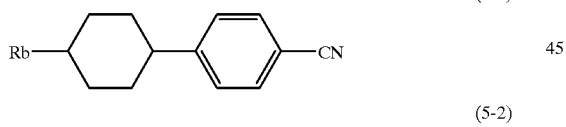

(5-2)

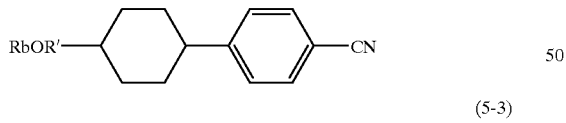

(5-3)

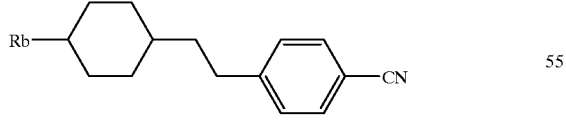

(5-4)

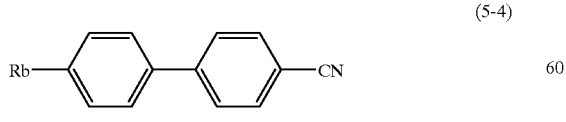

(5-5)

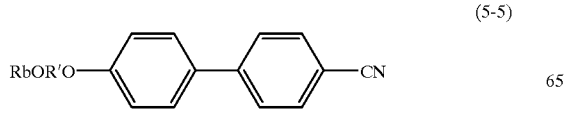

(5-6)

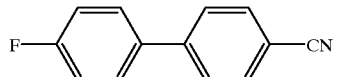

(5-7)

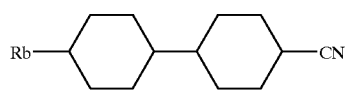

(5-8)

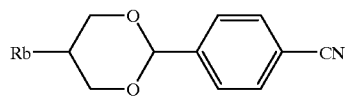

(5-9)

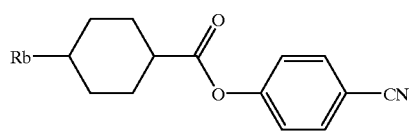

(5-10)

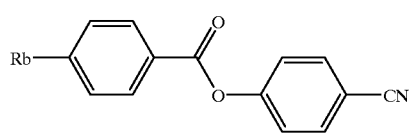

(5-11)

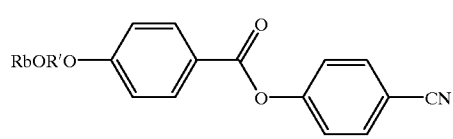

(5-12)

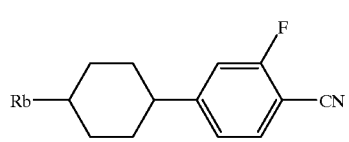

(5-13)

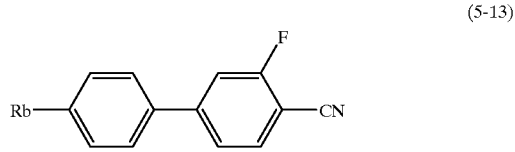

(5-14)

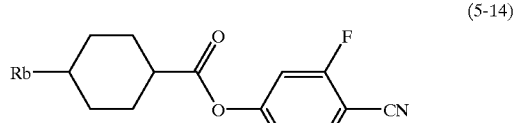

(5-15)

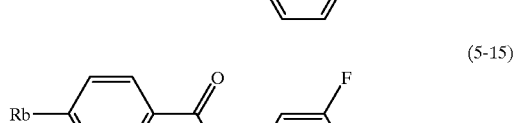

(5-16)

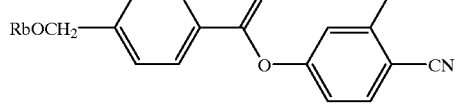

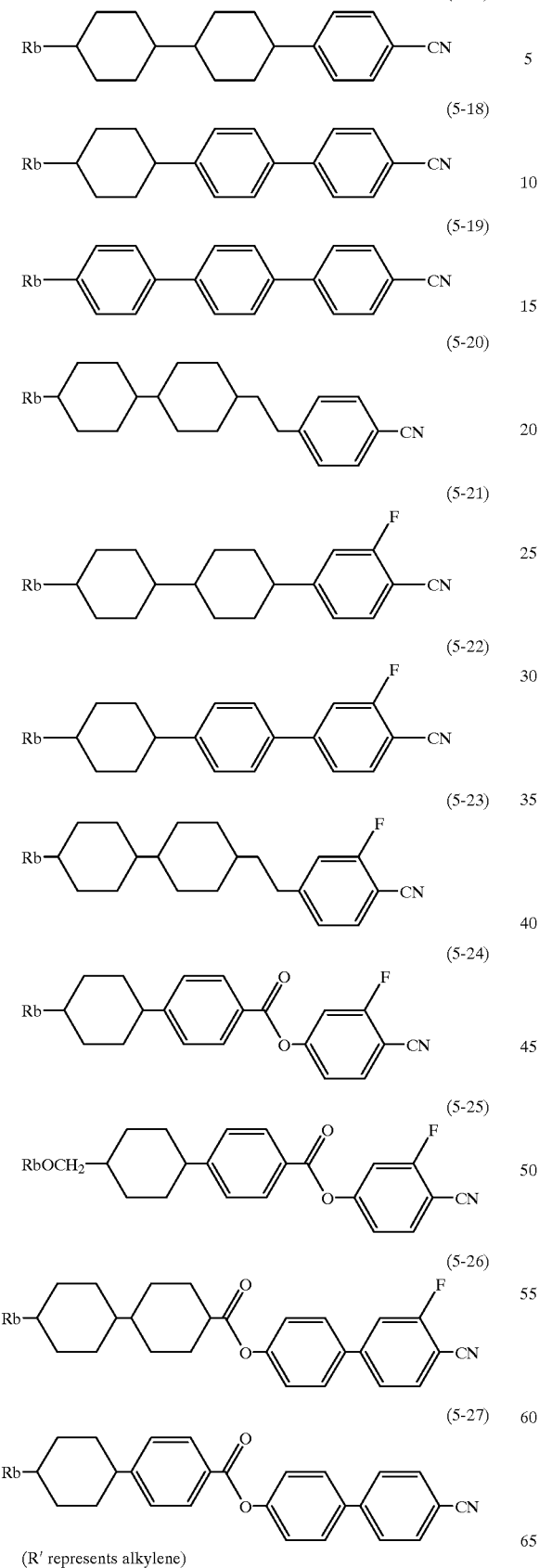
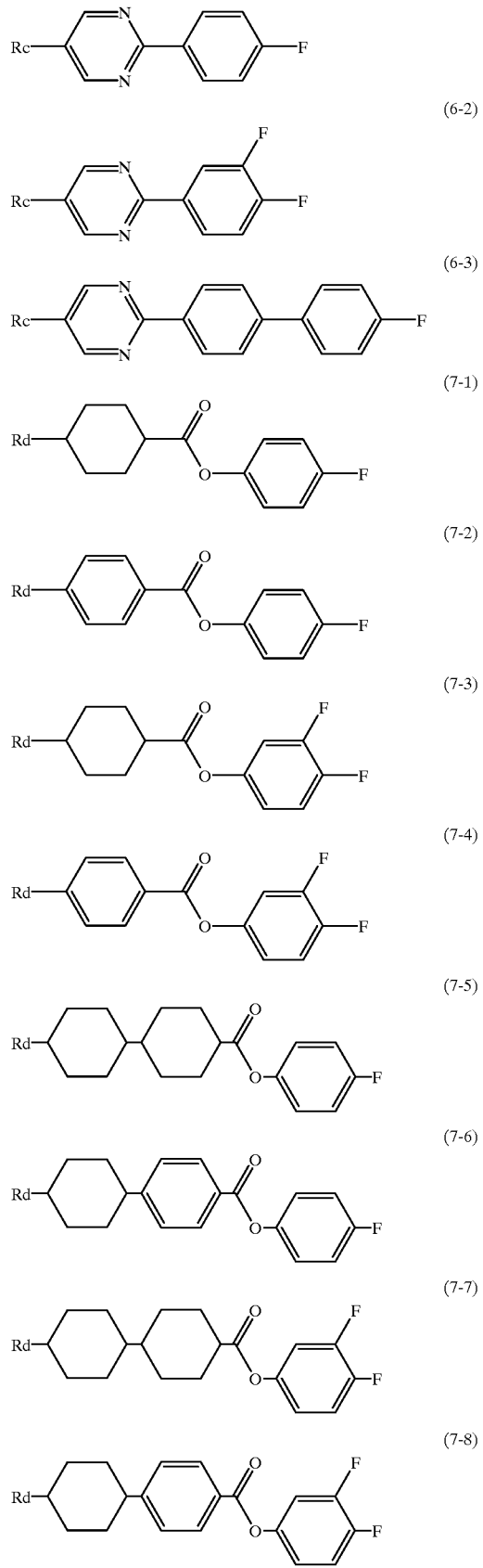
(R' represents alkylene)

(7-9)
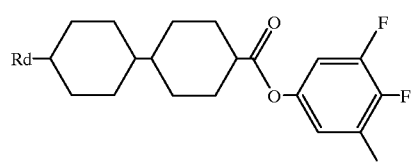

(7-10)
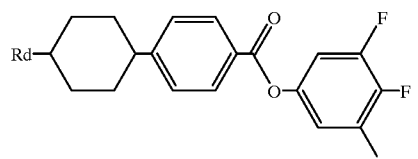

(7-11)
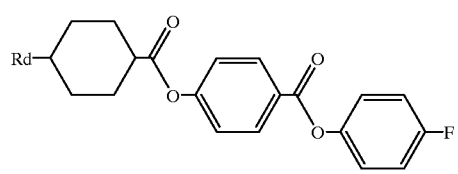

(7-12)
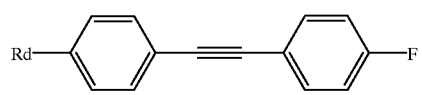

(7-13)
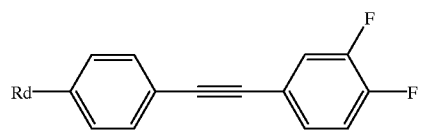

Compounds expressed by any one of general formulas (5) to (7) have a large positive dielectric anisotropy and are used particularly for the purpose of lowering threshold voltage. They are also used for the purpose of adjusting viscosity and optical anisotropy, and of widening nematic range by, for instance, raising clearing point. Further, they are used for the purpose of improving the steepness.

As the compounds of the present invention expressed by general formula (8) or (9), the following compounds can preferably be mentioned:

(In the followings, Re, Rf, Rg, and Rh represent an alkyl group or alkenyl group.)

(8-1)
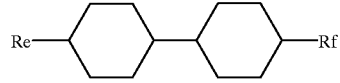

(8-2)
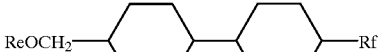

(8-3)
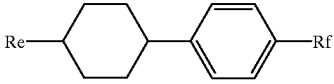

(8-4)
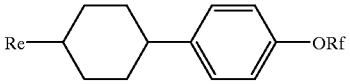

(8-5)
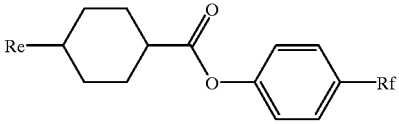

(8-6)
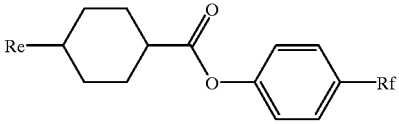

(8-7)
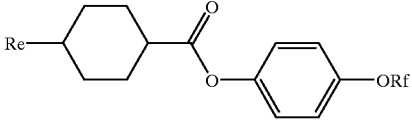

(8-8)
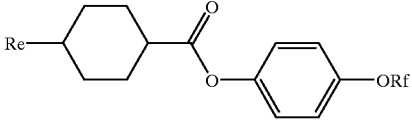

(8-9)
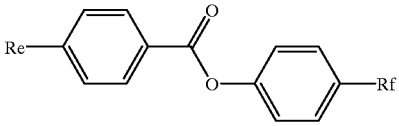

(8-10)
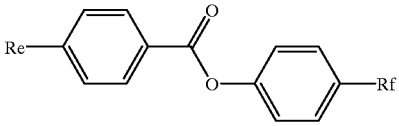

(8-11)
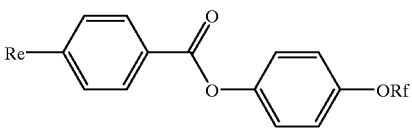

(8-12)
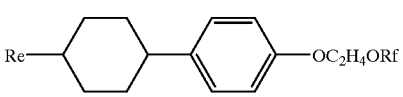

(8-13)
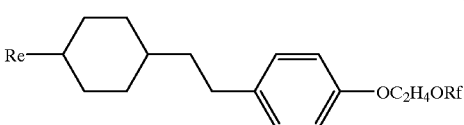

(8-14)
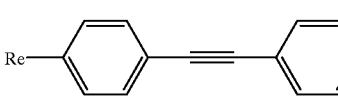

(8-15)
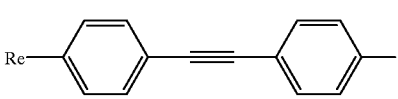

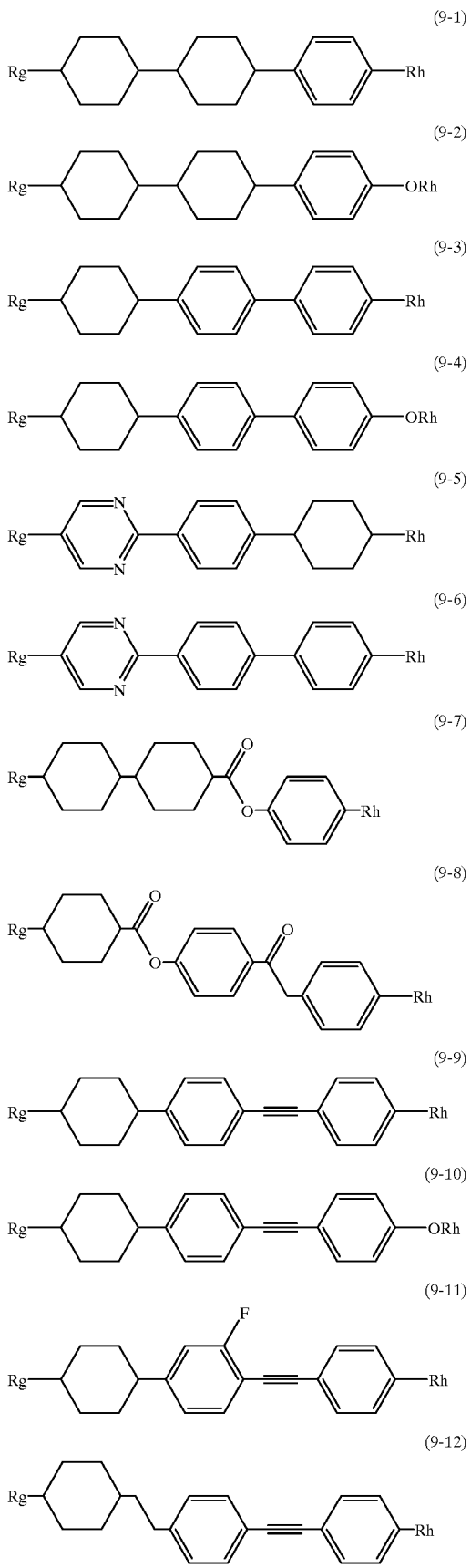
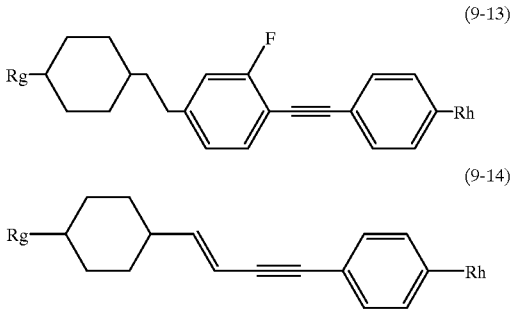

Compounds expressed by general formula (8) or (9) are ones having a negative or small positive dielectric anisotropy. Compounds expressed by general formula (8) are used for the purpose of principally reducing viscosity and/or adjusting optical anisotropy. Compounds expressed by general formula (9) are used for the purpose of widening nematic range by, for instance, raising clearing point and/or adjusting optical anisotropy.

Compounds expressed by any one of general formulas (5) to (9) are indispensable particularly when liquid crystal compositions for STN display mode or ordinary TN display mode are produced.

While the compounds of general formulas (5) to (9) can optionally be used in the range of 1 to 99% by weight when liquid crystal compositions for ordinary TIN display mode or STN display mode are produced, the use in an amount of 10 to 97% by weight is preferable, and 40 to 95% by weight is more desirable. Also at that time, a compound expressed by any one of general formulas (2) to (4) may be used as a part of the composition.

By using the liquid crystal compositions of the present invention for TFT liquid crystal display devices, steepness and viewing angle can be improved. Also, since the compounds expressed by general formula (1) have a low viscosity, the response speed of the liquid crystal display devices comprising the compounds can be improved.

Liquid crystal compositions used according to the present invention are produced by the methods which are conventional in the art. Generally, methods are adopted in which various components are dissolved with each other at a high temperature. Also, liquid crystal materials of the present invention are improved, depending on the intended uses, by using a suitable additive to optimize. Such additives are well known in the art and described in literatures in detail. Usually, a chiral dopant or likes are added to cause a helical structure of liquid crystal to adjust a required twisting angle, and to avoid reverse-twist.

Further, the liquid crystal compositions of the present invention can be used as liquid crystal compositions for guest-host (GH) mode by adding a dichroic dye such as merocyanine type, styryl type, azo type, azomethine type, azoxy type, quinophthalone type, anthraquinone type, and tetrazine type dye. Alternatively, they can also be used as liquid crystal compositions for polymer dispersion type liquid crystal display devices (PDLCD) typified by NCAP which is prepared by forming a nematic liquid crystal into a microcapsule or typified by a polymer net work liquid crystal display devices (PNLCD) which is prepared by forming a polymer of three-dimensional network structure in a liquid crystal. Also, the liquid crystal compositions of the present invention can be used as ones for electrically controlled birefringence (ECB) mode or dynamic scattering (DS) mode.

As the nematic liquid crystal compositions containing the compounds of the present invention and produced by the methods mentioned above, composition examples can be shown as follows:

COMPOSITION EXAMPLE 1

| | |
|---|---|
| 4-(1,5-hexadienyl)-4'-pentylbicyclohexane | 17% |
| 3,5-difluoro-4-cyanophenyl-4-(3-pentenyl)benzoate | 8% |
| 4-(4-propylcyclohexyl)benzonitrile | 24% |
| 4-(4-propylcyclohexyl)ethoxybenzene | 6% |
| 4-(4-(4-propylcyclohexyl)cyclohexyl)methylbenzene | 10% |
| 4-(4-(4-propylcyclohexyl)cyclohexyl)propylbenzene | 16% |
| 4-(2-(2-fluoro-4-(4-propylcyclohexyl)phenyl)ethynyl)ethylbenzene | 7% |
| 4-(2-(4-(2-(4-propylcyclohexyl)ethyl)phenyl)ethenyl)ethylbenzene | 4% |
| 4-(2-(4-(2-(4-propylcyclohexyl)ethyl)phenyl)ethenyl)propylbenzene | 4% |
| 4-(2-(4-(2-(4-propylcyclohexyl)ethyl)phenyl)ethenyl)butylbenzene | 4% |

COMPOSITION EXAMPLE 2

| | |
|---|---|
| 4-(1,5-hexadienyl)-4'-ethylbicyclohexane | 8% |
| 4-(1,5-hexadienyl)-4'-propylbicyclohexane | 8% |
| 4-(1,5-hexadienyl)-4'-pentylbicyclohexane | 8% |
| 4-(4-(3-butenyl)cyclohexyl)benzonitrile | 10% |
| 4-(4-(3-pentenyl)cyclohexyl)benzonitrile | 10% |
| 4-(4-propylcyclohexyl)benzonitrile | 10% |
| 3,5-difluoro-4-cyanophenyl-4-(3-pentenyl)benzoate | 3% |
| 4-(4-propylcyclohexyl)ethoxybenzene | 3% |
| 4-(2-(4-butylphenyl)ethynyl)ethoxybenzene | 6% |
| 4-(4-(4-propylcyclohexyl)cyclohexyl)methoxybenzene | 5% |
| 4-(4-(4-propylcyclohexyl)cyclohexyl)methylbenzene | 10% |
| 4-(2-(4-(2-(4-ethylcyclohexyl)ethyl)phenyl)ethenyl)ethylbenzene | 3% |
| 4-(2-(4-(2-(4-ethylcyclohexyl)ethyl)phenyl)ethenyl)butylbenzene | 3% |
| 4-(2-(4-(2-(4-propylcyclohexyl)ethyl)phenyl)ethenyl)ethylbenzene | 3% |
| 4-(2-(4-(2-(4-propylcyclohexyl)ethyl)phenyl)ethenyl)propylbenzene | 3% |
| 4-(2-(4-(2-(4-propylcyclohexyl)ethyl)phenyl)ethenyl)butylbenzene | 3% |
| 4-(4-(4-propylcyclohexyl)cyclohexyl)fluorobenzene | 4% |

COMPOSITION EXAMPLE 3

| | |
|---|---|
| 4-(4-(1,5-hexadienyl)cyclohexyl)benzonitrile | 10% |
| 4-(4-(1,5-hexadienyl)cyclohexyl)propylbenzene | 10% |
| 4-(4-ehtylcyclohexyl)benzonitrile | 3% |
| 4-(4-propylcyclohexyl)benzonitrile | 20% |
| 4-cyanophenyl-4-ethylbenzoate | 6% |
| 4-cyanophenyl-4-propylbenzoate | 3% |
| 4-(2-(4-ethylphenyl)ethynyl)methoxybenzene | 3% |
| 4-(2-(4-propylphenyl)ethynyl)methoxybenzene | 3% |
| 4-(2-(4-butylphenyl)ethynyl)methoxybenzene | 3% |
| 4-(2-(4-pentylphenyl)ethynyl)methoxybenzene | 3% |
| 4-(2-(4-butylphenyl)ethynyl)ethoxybenzene | 3% |
| 4-(2-(2-fluoro-4-(4-propylcyclohexyl)phenyl)ethynyl)ethylbenzene | 6% |
| 4-(2-(2-fluoro-4-(4-propylcyclohexyl)phenyl)ethynyl)propylbenzene | 6% |
| 4-(2-(2-fluoro-4-(4-propylcyclohexyl)phenyl)ethynyl)butylbenzene | 6% |
| 4-(2-(4-(2-(4-ethylcyclohexyl)ethynyl)phenyl)ethynyl)ethylbenzene | 3% |
| 4-(2-(4-(2-(4-ethylcyclohexyl)ethynyl)phenyl)ethynyl)propylbenzene | 3% |
| 4-(2-(4-(2-(4-propylcyclohexyl)ethynyl)phenyl)ethynyl)ethylbenzene | 3% |
| 4-(2-(4-(2-(4-propylcyclohexyl)ethynyl)phenyl)ethynyl)propylbenzene | 3% |
| 4-(2-(4-(2-(4-propylcyclohexyl)ethynyl)phenyl)ethynyl)butylbenzene | 3% |

COMPOSITION EXAMPLE 4

| | |
|---|---|
| 4-(4-(4-(1,5-hexadienyl)cyclohexyl)cyclohexyl)methylbenzene | 7% |
| 4-(4-(4-(1,5-hexadienyl)cyclohexyl)cyclohexyl)benzonitrile | 10% |
| 2-(3,4-difluorophenyl)-5-propylpyrimidine | 8% |
| 2-fluoro-4-(4-ethylcyclohexyl)benzonitrile | 8% |
| 2-fluoro-4-(4-propylcyclohexyl)benzonitrile | 8% |
| 4-(4-propylcyclohexyl)benzonitrile | 4% |
| 4-(4-(4-ethylcyclohexyl)cyclohexyl)-1,2-difluorobenzene | 6% |
| 4-(4-(4-propylcyclohexyl)cyclohexyl)-1,2-difluorobenzene | 6% |
| 4-(4-(4-pentylcyclohexyl)cyclohexyl)-1,2-difluorobenzene | 6% |
| 4-(4-(4-propylcyclohexyl)cyclohexyl)methylbenzene | 7% |
| 4-(4-(4-propylcyclohexyl)cyclohexyl)propylbenzene | 7% |
| 4-(4-(4-propylcyclohexyl)cyclohexyl)methoxybenzene | 7% |
| 4-(4-(4-ethylcyclohexyl)cyclohexyl)-2-fluorobenzonitrile | 3% |
| 4-(4-(4-propylcyclohexyl)cyclohexyl)-2-fluorobenzonitrile | 7% |
| 2-4'-fluorobiphenyl-5-propylpyrimidine | 3% |
| 2-4'-fluorobiphenyl-5-butylpyrimidine | 3% |
| 2-(4-fluorophenyl)-5-pentylpyrimidine | 3% |

COMPOSITION EXAMPLE 5

| | |
|---|---|
| 4-(4-(1,5-hexadienyl)cyclohexyl)-4-ethylbiphenyl | 7% |
| 4-(4-(1,5-hexadienyl)cyclohexyl)benzonitrile | 8% |
| 4-(4-(3-butenyl)cyclohexyl)benzonitrile | 10% |
| 4-(4-(3-pentenyl)cyclohexyl)benzonitrile | 10% |
| 4-(4-propylcyclohexyl)benzonitrile | 20% |
| 4-(4-pentylcyclohexyl)benzonitrile | 20% |
| 2-(4-ethylphenyl)-5-ethylpyrimidine | 3% |
| 2-(4-ethylphenyl)-5-propylpyrimidine | 3% |
| 2-(4-ethylphenyl)-5-butylpyrimidine | 3% |
| 4-(4-(4-propylcyclohexyl)cyclohexyl)methylbenzene | 5% |
| 4-(4-(4-propylcyclohexyl)cyclohexyl)propylbenzene | 5% |
| 4-(4-(4-propylcyclohexyl)cyclohexyl)methoxybenzene | 3% |
| 4-(2-(4-(2-(4-propylcyclohexyl)ethyl)phenyl)ethenyl)ethylbenzene | 3% |
| 2-(4-(4-propylcyclohexyl)phenyl)-5-ethylpyrimidine | 2% |
| 2-(4-(4-propylcyclohexyl)phenyl)-5-propylpyrimidine | 2% |
| 2-(4'-fluorobiphenyl)-5-ethylpyrimidine | 2% |
| 2-(4-cyanophenyl)-5-ethyl-1,3-dioxane | 2% |
| 2-(4-cyanophenyl)-5-propyl-1,3-dioxane | 2% |

COMPOSITION EXAMPLE 6

| | |
|---|---|
| 4'-(1,5-hexadienyl)-4-methylbicyclohexane | 5% |
| 4'-(1,5-hexadienyl)-4-ethylbicyclohexane | 5% |
| 4-(4-(1,5-hexadienyl)cyclohexyl)benzonitrile | 10% |
| 4-(4-(3-butenyl)cyclohexyl)benzonitrile | 8% |
| 4-(4-(3-pentenyl)cyclohexyl)benzonitrile | 8% |
| 4-(4-propylcyclohexyl)benzonitrile | 8% |
| 4-(4-pentylcyclohexyl)benzonitrile | 8% |
| 4-(4-methoxymethylcyclohexyl)benzonitrile | 8% |
| 4-(4-ethoxymethylcyclohexyl)benzonitrile | 4% |
| 4-(2-(4-ethylphenyl)ethynyl)methoxybenzene | 2% |
| 4-(2-(4-propylphenyl)ethynyl)methoxybenzene | 2% |
| 4-(2-(4-butylphenyl)ethynyl)methoxybenzene | 2% |
| 4-(2-(4-pentylphenyl)ethynyl)methoxybenzene | 2% |
| 4-(2-(4-butylphenyl)ethynyl)ethoxybenzene | 2% |
| 4'-propyl-4-butylbicyclohexane | 8% |
| 4-(4-(4-ethylcyclohexyl)cyclohexyl)benzonitrile | 4% |
| 4-(4-(4-propylcyclohexyl)cyclohexyl)benzonitrile | 4% |

-continued

| | |
|---|---|
| 4-(2-(4-(2-(4-propylcyclohexyl)ethynyl)phenyl)ethynyl)propylbenzene | 3% |
| 4-(2-(4-(2-(4-propylcyclohexyl)ethynyl)phenyl)ethynyl)butylbenzene | 3% |

| | |
|---|---|
| 4-(4-(4-propylcyclohexyl)cyclohexyl)methylbenzene | 5% |
| 4-(4-(4-propylcyclohexyl)cyclohexyl)propylbenzene | 5% |

COMPOSITION EXAMPLE 7

| | |
|---|---|
| 4-(4-(1,5-hexadienyl)cyclohexyl)benzonitrile | 10% |
| 4-(4-(1,5-hexadienyl)cyclohexyl)propylbenzene | 5% |
| 4'-(1,5-hexadienyl)-4-propylbicyclohexane | 5% |
| 4-(4-ethylphenyl)benzonitrile | 6% |
| 4-(4-butylphenyl)benzonitrile | 6% |
| 4-(4-pentylphenyl)benzonitrile | 6% |
| 4-(4-ethylcyclohexyl)benzonitrile | 10% |
| 4-(4-propylcyclohexyl)benzonitrile | 5 |
| 2-(4-butylphenyl)-5-propylpyrimidine | 1.5% |
| 2-(4-butylphenyl)-5-butylpyrimidine | 1.5% |
| 2-(4-butylphenyl)-5-pentylpyrimidine | 1.5% |
| 2-(4-pentylphenyl)-5-propylpyrimidine | 1.5% |
| 2-(4-pentylphenyl)-5-butylpyrimidine | 1.5% |
| 2-(4-pentylphenyl)-5-hexylpyrimidine | 1.5% |
| 4-(4-(4-ethylcyclohexyl)cyclohexyl)methylbenzene | 3% |
| 4-(4-(4-propylcyclohexyl)cyclohexyl)methylbenzene | 5% |
| 4-(4-(4-propylcyclohexyl)cyclohexyl)propylbenzene | 8% |
| 4-(4-(4-propylcyclohexyl)cyclohexyl)methoxybenzene | 3% |
| 4-(4-(4-propylcyclohexyl)cyclohexyl)fluorobenzene | 3% |
| 4-(4-(4-ethylcyclohexyl)cyclohexyl)benzonitrile | 4% |
| 4-(4-(4-propylcyclohexyl)cyclohexyl)benzonitrile | 4% |
| 4-(4-(4-butylcyclohexyl)cyclohexyl)benzonitrile | 4% |
| 2-(4-methoxyphenyl)-5-ethylpyrimidine | 2% |
| 2-(4-ethoxyphenyl)-5-propylpyrimidine | 2% |

COMPOSITION EXAMPLE 8

| | |
|---|---|
| 4'-(1,5-heptadienyl)-4-propylbicyclohexane | 3% |
| 4-(2-(4-(1,5-hexadienyl)cyclohexyl)ethyl)propyl-cyclohexane | 3% |
| 4-(4-(1,5-hexadienyl)cyclohexyl)benzonitrile | 10% |
| 4-(4-(4-(1,5-hexadienyl)cyclohexyl)cyclohexyl)benzonitrile | 3% |
| 3-fluoro-4-cyanophenyl-4-ethoxymethylbenzoate | 3% |
| 3-fluoro-4-cyanophenyl-4-propoxymethylbenzoate | 3% |
| 4-(4-methoxymethylcyclohexyl)benzonitrile | 5% |
| 4-(4-ethylcyclohexyl)benzonitrile | 20% |
| 4-(4-propylcyclohexyl)benzonitrile | 15% |
| 4'-methoxymethyl-4-pentylbicyclohexane | 8% |
| 4-(4-(4-ethylcyclohexyl)cyclohexyl)benzonitrile | 3% |
| 4-(4-(4-propylcyclohexyl)cyclohexyl)benzonitrile | 3% |
| 4-(4-(4-butylcyclohexyl)cyclohexyl)benzonitrile | 3% |
| 2-(4'-fluorobiphenyl)-5-propylpyrimidine | 3% |
| 4-(4-(4-propylcyclohexyl)cyclohexyl)methylbenzene | 3% |
| 4-fluorophenyl-4-(4-propylcyclohexyl)cyclohexane-carboxylate | 3% |
| 4-fluorophenyl-4-(4-pentylcyclohexyl)cyclohexane-carboxylate | 3% |
| 2-(4'-ethylbiphenyl)-5-propylpyrimidine | 3% |
| 2-(4'-butylbiphenyl)-5-propylpyrimidine | 3% |

COMPOSITION EXAMPLE 9

| | |
|---|---|
| 4-(4-(2-(4-(1,6-heptadienyl)cyclohexyl)ethyl)cyclohexyl)-1,2-difluorobenzene | 9% |
| 4-(2-(4-(1,7-octadienyl)phenyl)ethynyl)pentylbenzene | 9% |
| 4-(4-(1,5-hexadienyl)cyclohexyl)benzonitrile | 3% |
| 4-(4-propylcyclohexyl)benzonitrile | 10% |
| 4-(4-propoxymethylcyclohexyl)benzonitrile | 8% |
| 4-(2-(4-ethylphenyl)ethynyl)methylbenzene | 4% |
| 4-(2-(4-propylphenyl)ethynyl)hexylbenzene | 8% |
| 4-(2-(4-butylphenyl)ethynyl)butylbenzene | 4% |
| 4-(4-(4-propylcyclohexyl)cyclohexyl)benzonitrile | 3% |
| 4-(4-(2-(4-ethylcyclohexyl)ethyl)cyclohexyl)-1,2-difluorobenzene | 10% |
| 4-(4-(2-(4-propylcyclohexyl)ethyl)cyclohexyl)-1,2-difluorobenzene | 5% |
| 4-(4-(2-(4-pentylcyclohexyl)ethyl)cyclohexyl)-1,2-difluorobenzene | 10% |
| 4-(4-(4-propylcyclohexyl)cyclohexyl)methoxybenzene | 3% |
| 4-(4-(4-propylcyclohexyl)cyclohexyl)methylbenzene | 7% |
| 4-(2-(2-fluoro-4-propylcyclohexyl)phenyl)ethynyl)ethylbenzene | 3% |

COMPOSITION EXAMPLE 10

| | |
|---|---|
| 4-(1,5-hexadienyl)phenyl-4-(4-propylcyclohexyl)benzoate | 10% |
| 4-(4-(4-(1,5-hexadienyl)cyclohexyl)cyclohexyl)propylbenzene | 6% |
| 4'-(3,7-octadienyl)-4-propylbicyclohexane | 6% |
| 4-(4-ethylcyclohexyl)-2-fluorobenzonitrile | 3% |
| 4-(4-propylcyclohexyl)-2-fluorobenzonitrile | 3% |
| 4-(4-pentylcyclohexyl)-2-fluorobenzonitrile | 3% |
| 4-ethylphenyl-4-methoxybenzoate | 5% |
| 4-fluorophenyl-4-pentylcyclohexanecarboxylate | 4% |
| 4-fluorophenyl-4-heptylcyclohexanecarboxylate | 4% |
| 4-butoxyphenyl-4-propylcyclohexanecarboxylate | 8% |
| 4-ethoxyphenyl-4-butylcyclohexanecarboxylate | 6% |
| 4-methoxyphenyl-4-pentylcyclohexanecarboxylate | 6% |
| 4-ethoxyphenyl-4-propylcyclohexanecarboxylate | 5% |
| 4-ethoxyphenyl-4-pentylcyclohexanecarboxylate | 4% |
| 4-ethoxyphenyl-4-butylcyclohexanecarboxylate | 8% |
| 4-(4-(4-propylcyclohexyl)cyclohexyl)methylbenzene | 5% |
| 4-(4-(4-propylcyclohexyl)cyclohexyl)propylbenzene | 5% |
| 4-(4-(4-propylcyclohexyl)cyclohexyl)methoxybenzene | 3% |
| 4-fluorophenyl-4-(4-propylcyclohexanoyloxy)benzoate | 3% |

COMPOSITION EXAMPLE 11

| | |
|---|---|
| 2-(4-(1,5-hexadienyl)phenyl)-5-propylpyrimidine | 5% |
| 4-(4-(4-(1,5-hexadienyl)cyclohexyl)cyclohexyl)methylbenzene | 5% |
| 4-(1,5-hexadienyl)phenyl-4-(4-propylcyclohexyl)benzoate | 5% |
| 2-(3,4-difluorophenyl)-5-propylpyrimidine | 8% |
| 2-(4'-fluorobiphenyl)-5-propylpyrimidine | 5% |
| 2-(4'-fluorobiphenyl)-5-butylpyrimidine | 5% |
| 2-(4'-fluorobiphenyl)-5-pentylpyrimidine | 5% |
| 2-(4-ethylphenyl)-5-ethylpyrimidine | 4% |
| 2-(4-ethylphenyl)-5-propylpyrimidine | 4% |
| 2-(4-ethylphenyl)-5-butylpyrimidine | 4% |
| 4-butoxyphenyl-4-propylcyclohexanecarboxylate | 6% |
| 4-ethoxyphenyl-4-butoxycyclohexanecarboxylate | 6% |
| 4-ethoxyphenyl-4-pentylcyclohexanecarboxylate | 6% |
| 4-(2-(4-(2-(4-ethylcyclohexyl)ethyl)phenyl)ethynyl)butylbenzene | 4% |
| 4-(2-(4-(2-(4-propylcyclohexyl)ethyl)phenyl)ethynyl)butylbenzene | 4% |
| 4-(4-(4-propylcyclohexyl)cyclohexyl)methylbenzene | 6% |
| 4-(4-(4-propylcyclohexyl)cyclohexyl)propylbenzene | 6% |
| 4'-cyanobiphenyl-4-(4-propylcyclohexyl)cyclohexane-carboxylate | 3% |
| 4'-cyanobiphenyl-4-(4-pentylcyclohexyl)cyclohexane-carboxylate | 3% |
| 4'-cyanobiphenyl-4-(4-propylcyclohexyl)benzoate | 3% |
| Methyl-4-(4-pentylcyclohexyl)cyclohexanecarboxylate | 3% |

COMPOSITION EXAMPLE 12

| | |
|---|---|
| 4'-(1,5-hexadienyl)-4-pentylbicyclohexane | 6% |
| 4-(4-(1,5-hexadienyl)cyclohexyl)propylbenzene | 5% |
| 4-(4-(4-(1,5-hexadienyl)cyclohexyl)cyclohexyl)methylbenzene | 5% |
| 4-(4-heptylcyclohexyl)-1,3-difluorobenzene | 4% |

-continued

| | |
|---|---|
| 4-(2-(4-pentylcyclohexyl)ethyl)-1,2-difluorobenzene | 5% |
| 4-(4-(4-ethylcyclohexyl)cyclohexyl)-1,2-difluorobenzene | 11% |
| 4-(4-(4-propylcyclohexyl)cyclohexyl)-1,2-difluorobenzene | 11% |
| 4-(4-(4-pentylcyclohexyl)cyclohexyl)-1,2-difluorobenzene | 11% |
| 4-(4-(2-(4-ethylcyclohexyl)ethyl)cyclohexyl)-1,2-difluorobenzene | 2% |
| 4-(4-(2-(4-propylcyclohexyl)ethyl)cyclohexyl)-1,2-difluorobenzene | 1% |
| 4-(4-(2-(4-pentylcyclohexyl)ethyl)cyclohexyl)-1,2-difluorobenzene | 2% |
| 4'-(4-ethylcyclohexyl)-3,4-difluorobiphenyl | 4% |
| 4'-(4-propylcyclohexyl)-3,4-difluorobiphenyl | 4% |
| 4'-(4-pentylcyclohexyl)-3,4-difluorobiphenyl | 8% |
| 4'-(4-ethylcyclohexyl)-4-fluorobiphenyl | 3% |
| 4'-(4-propylcyclohexyl)-4-fluorobiphenyl | 3% |
| 4'-(4-pentylcyclohexyl)-4-fluorobiphenyl | 2% |
| 4-(4-(4-propylcyclohexyl)cyclohexyl)fluorobenzene | 3% |
| 4-(4-(4-propylcyclohexyl)cyclohexyl)methylbenzene | 5% |
| 4-(2-(4-pentylcyclohexyl)ethyl)-1,2-difluorobenzene | 5% |

COMPOSITION EXAMPLE 13

| | |
|---|---|
| 4'-(4-(1,5-hexadienyl)cyclohexyl)-4-ethylbiphenyl | 4% |
| 4'-(1,5-hexadienyl)-4-pentylbicyclohexane | 6% |
| 4-(4-(1,5-hexadienyl)cyclohexyl)propylbenzene | 3% |
| 5-(4-heptylcyclohexyl)-1,2,3-trifluorobenzene | 8% |
| 5-(4-(4-propylcyclohexyl)cyclohexyl)-1,2,3-trifluorobenzene | 8% |
| 5-(4-(4-butylcyclohexyl)cyclohexyl)-1,2,3-trifluorobenzene | 4% |
| 5-(4-(2-(4-propylcyclohexyl)ethyl)cyclohexyl)-1,2,3-trifluorobenzene | 10% |
| 5-(4-(2-(4-butylcyclohexyl)ethyl)cyclohexyl)-1,2,3-trifluorobenzene | 8% |
| 5-(4-(2-(4-pentylcyclohexyl)ethyl)cyclohexyl)-1,2,3-trifluorobenzene | 8% |
| 5-(2-(4-(4-propylcyclohexyl)cyclohexyl)ethyl)-1,2,3-trifluorobenzene | 10% |
| 5-(2-(4-(4-pentylcyclohexyl)cyclohexyl)ethyl)-1,2,3-trifluorobenzene | 9% |
| 4'-(4-propylcyclohexyl)-3,4,5-trifluorobiphenyl | 8% |
| 4'-(4-pentylcyclohexyl)-3,4,5-trifluorobiphenyl | 8% |
| 4'-(4-(4-propylcyclohexyl)cyclohexyl)-3,4,5 trifluorobiphenyl | 3% |
| 4'-(2-(4-(4-propylcyclohexyl)cyclohexyl)ethyl)-3,4,5-trifluorobiphenyl | 3% |

COMPOSITION EXAMPLE 14

| | |
|---|---|
| 4'-(4-(1,5-hexadienyl)cyclohexyl)-3,4,5-trifluorobiphenyl | 10% |
| 4'-(1,5-heptadienyl)-4-propylbicyclohexane | 3% |
| 4'-(4-(1,5-hexadienyl)cyclohexyl)-4-(4-propylcyclohexyl)biphenyl | 3% |
| 5-(4-(2-(4-propylcyclohexyl)ethyl)cyclohexyl-1,2,3-trifluorobenzene | 7% |
| 5-(4-(2-(4-butylcyclohexyl)ethyl)cyclohexyl-1,2,3-trifluorobenzene | 7% |
| 5-(4-(2-(4-pentylcyclohexyl)ethyl)cyclohexyl-1,2,3-trifluorobenzene | 6% |
| 5-(2-(4-(4-propylcyclohexyl)cyclohexyl)ethyl)-1,2,3-trifluorobenzene | 5% |
| 4'-(2-(4-propylcyclohexyl)ethyl)-3,4,5-trifluorobiphenyl | 5% |
| 4'-(2-(4-butylcyclohexyl)ethyl)-3,4,5-trifluorobiphenyl | 5% |
| 4'-(2-(4-pentylcyclohexyl)ethyl)-3,4,5-trifluorobiphenyl | 5% |
| 3,4,5-trifluorophenyl-4-(4-propylcyclohexyl)benzoate | 2% |
| 3,4,5-trifluorophenyl-4-(4-pentylcyclohexyl)benzoate | 2% |
| 3,4,5-trifluorophenyl-4-(4-propylcyclohexyl)cyclohexanecarboxylate | 8% |

COMPOSITION EXAMPLE 15

| | |
|---|---|
| 4'-(4-(1,5-hexadienyl)cyclohexyl)-3,4,5-trifluorobiphenyl | 7% |
| 4-(2-(4-(1,5-hexadienyl)cyclohexyl)ethenyl)propylcyclohexane | 7% |
| 4-(4-(4-(6,6-difluoro-1,5-hexadienyl)cyclohexyl)cyclohexyl)pentylcyclohexane | 7% |
| 4-(4-propylcyclohexyl)chlorobenzene | 5% |
| 5-(4-heptylcyclohexyl)-3,4,5-trifluorobenzene | 8% |
| 4'-(4-ethylcyclohexyl)-3,4-difluorobiphenyl | 6% |
| 4'-(4-propylcyclohexyl)-3,4-difluorobiphenyl | 6% |
| 4'-(4-pentylcyclohexyl)-3,4-difluorobiphenyl | 6% |
| 4-(4-(4-ethylcyclohexyl)cyclohexyl)chlorobenzene | 4% |
| 4-(4-(4-butylcyclohexyl)cyclohexyl)chlorobenzene | 8% |
| 4-(4-(4-pentylcyclohexyl)cyclohexyl)chlorobenzene | 4% |
| 4'-(4-propylcyclohexyl)-3,4,5-trifluorobiphenyl | 10% |
| 4'-(4-pentylcyclohexyl)-3,4,5-trifluorobiphenyl | 10% |
| 4-(2-(2-fluoro-4-(4-propylcyclohexyl)phenyl)ethenyl)ethylbenzene | 4% |
| 4-(2-(2-fluoro-4-(4-propylcyclohexyl)phenyl)ethenyl)propylbenzene | 4% |
| 4-(4-(2-(4-propylcyclohexyl)ethyl)cyclohexyl)-3-fluorochlorobenzene | 4% |

COMPOSITION EXAMPLE 16

| | |
|---|---|
| 4'-(1,5-hexadienyl)-4-propylbicyclohexane | 7% |
| 4'-(1,5-hexadienyl)-4-pentylbicyclohexane | 7% |
| 4'-(4-(1,5-hexadienyl)cyclohexyl-3,4,5-trifluorobenzene | 7% |
| 4-(4-pentylcyclohexyl)fluorobenzene | 8% |
| 4-(4-heptylcyclohexyl)fluorobenzene | 8% |
| 4-(4-(4-ethylcyclohexyl)cyclohexyl)trifluoromethoxybenzene | 5% |
| 4-(4-(4-propylcyclohexyl)cyclohexyl)trifluoromethoxybenzene | 5% |
| 4-(4-(4-pentylcyclohexyl)cyclohexyl)trifluoromethoxybenzene | 5% |
| 1,6-difluoro-4-(4-(4-propylcyclohexyl)cyclohexyl)difluoromethoxybenzene | 15% |
| 1,6-difluoro-4-(4-(4-pentylcyclohexyl)cyclohexyl)difluoromethoxybenzene | 15% |
| 2',6'-difluoro-4'-(propylcyclohexyl)-3,4-difluorobiphenyl | 6% |
| 2',6'-difluoro-4'-(pentylcyclohexyl)-3,4-difluorobiphenyl | 6% |
| 4-trifluoromethoxyphenyl-4-(4-propylcyclohexyl)cyclohexanecarboxylate | 3% |
| 4-trifluoromethoxyphenyl-4-(4-pentylcyclohexyl)cyclohexanecarboxylate | 3% |

COMPOSITION EXAMPLE 17

| | |
|---|---|
| 4'-(4-(1,5-hexadienyl)cyclohexyl)-3,4,5-trifluorobiphenyl | 10% |
| 4-(2-(4-(1,6-heptadienyl)cyclohexyl)ethyl)cyclohexyl)-3,4-difluorobenzene | 10% |
| 4-(4-pentylcyclohexyl)fluorobenzene | 8% |
| 4-(4-hexylcyclohexyl)fluorobenzene | 8% |
| 4-(4-heptylcyclohexyl)fluorobenzene | 8% |
| 4-(4-(4-ethylcyclohexyl)cyclohexyl)trifluoromethoxybenzene | 6% |
| 4-(4-(4-propylcyclohexyl)cyclohexyl)trifluoromethoxybenzene | 6% |
| 4-(4-(4-butylcyclohexyl)cyclohexyl)trifluoromethoxybenzene | 6% |
| 4-(4-(4-pentylcyclohexyl)cyclohexyl)trifluoromethoxybenzene | 6% |
| 4-(2-(4-(4-propylcyclohexyl)cyclohexyl)ethyl)trifluoromethylbenzene | 5% |
| 4-(2-(4-(4-pentylcyclohexyl)cyclohexyl)ethyl)trifluoromethylbenzene | 5% |
| 4'-(4-propylcyclohexyl)-3,4-difluorobiphenyl | 8% |
| 4'-(4-pentylcyclohexyl-3,4-difluorobiphenyl | 8% |

COMPOSITION EXAMPLE 18

| | |
|---|---|
| 4-(4-(1,5-hexadienyl)cyclohexyl)benzonitrile | 5% |
| 4-(4-(4-(1,5-hexadienyl)cyclohexyl)cyclohexyl) benzonitrile | 5% |
| 4'-(1,5-hexadienyl)-4-methylbicyclohexane | 5% |
| 4-(4-(4-(1,5-hexadienyl)cyclohexyl)cyclohexyl) propylbenzene | 5% |
| 4-(4-(2-propenyl)cyclohexyl)benzonitrile | 4% |
| 4'-butyl-4-ethylbiphenyl | 4% |

-continued

| | |
|---|---|
| 4'-propyl-4-cyanobiphenyl | 5% |
| 4'-pentyl-4-cyanobiphenyl | 5% |
| 2-fluoro-4-(4-ethylcyclohexyl)benzonitrile | 5% |
| 4-(2-(4-propylcyclohexyl)ethyl)ethoxybenzene | 5% |
| 4-(2-(4-pentylcyclohexyl)ethyl)propoxybenzene | 8% |
| 4'-pentyl-4-cyanobiphenyl | 3% |
| 2-(4-cyanophenyl)-5-(4-butylphenyl)pyrimidine | 3% |
| 2-(4-pentylphenyl)-5-(4-butylphenyl)pyrimidine | 3% |
| 4-(2-(4-(4-pentylcyclohexyl)phenyl)ethyl)butylbenzene | 3% |
| 4-(2-(4-propylphenyl)ethyl)-4'-(4-pentylcyclohexyl) biphenyl | 3% |
| 4'-(1-propenyl)-4-methoxymethylbicyclohexane | 5% |
| 4'-propyl-4-(4-(3-pentenyl)cyclohexyl)biphenyl | 5% |
| 4-cyanophenyl-4-propylbenzoate | 5% |
| 4-methoxyphenyl-4-pentylcyclohexanecarboxylate | 7% |
| 4-propoxyphenyl-4-pentylcyclohexanecarboxylate | 7% |

COMPOSITION EXAMPLE 19

| | |
|---|---|
| 4-(4-(2-(4-(1,6-heptadienyl)cyclohexyl)ethyl) cyclohexyl)-3,4-difluorobenzene | 10% |
| 4-(2-(4-(1,7-octadienyl)phenyl)ethynyl)pentylbenzene | 10% |
| 3,4-difluorophenyl-4-butylcyclohexanecarboxylate | 5% |
| 3,4-difluorophenyl-4-pentylcyclohexanecarboxylate | 5% |
| 3-fluoro-4-cyanophenyl-4-ethylbenzoate | 4% |
| 3-fluoro-4-cyanophenyl-4-propylbenzoate | 4% |
| 3-fluoro-4-cyanophenyl-4-butylbenzoate | 6% |
| 3-fluoro-4-cyanophenyl-4-pentylbenzoate | 6% |
| 2-fluoro-4-(4-(3-methoxypropyl)cyclohexyl)benzonitrile | 6% |
| 3,4-difluorophenyl-4-(4-propylcyclohexyl) cyclohexanecarboxylate | |
| 3,4-difluorophenyl-4-(4-pentylcyclohexyl) cyclohexanecarboxylate | 4% |
| 3-fluoro-4-cyanophenyl-4-(4-ethylcyclohexyl)benzoate | 5% |
| 3-fluoro-4-cyanophenyl-4-(4-propylcyclohexyl)benzoate | 5% |
| 3-fluoro-4-cyanophenyl-4-(4-butylcyclohexyl)benzoate | 5% |
| 3-fluoro-4-cyanophenyl-4-(4-pentylcyclohexyl)benzoate | 5% |
| 4-(2-(4-(4-propylcyclohexyl)phenyl)ethynyl)ethylbenzene | 10% |
| 4'-(3-butenyl)-4-propylbicyclohexane | 3% |
| 4-(4-(4-(3-butenyl)cyclohexyl)cyclohexyl)methylbenzene | 3% |

Compounds of the present invention exhibit a large ratio of elastic constants $K_{33}/K_{11}$ and an extremely low viscosity. As shown in the Examples (Use Examples) mentioned below, the compounds of the present invention have about the same extent of a large elastic constant ratio $K_{33}/K_{11}$ as that of the alkenyl compounds which are currently most widely used, have a large elastic constant ratio $K_{33}/K_{11}$ and a low viscosity, and described in Laid-open Japanese Patent Publication No. Sho 61-83136 and Laid-open Japanese Patent Publication No. Sho 61-56137; and the compounds of the present invention exhibit a lower viscosity than that of the alkenyl compounds.

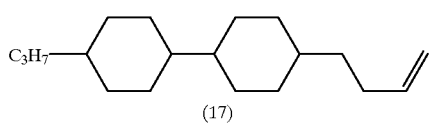

$K_{33}/K_{11}$ = 1.78 Extrapolated viscosity 17.8 mPa · s (17)

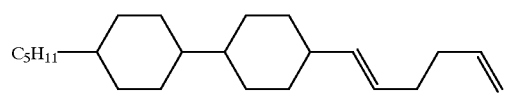

$K_{33}/K_{11}$ = 2.02 Extrapolated viscosity 15.0 mPa · s (Compound of Example 1)

(Compounds of Example 1)

Further, the compounds of the present invention exhibit a high stability as shown in Examples and have a chemical stability sufficient to be used for practical liquid crystal compositions.

By using the compounds (1) of the present invention having excellent characteristics, liquid crystal compositions having such excellent physical properties, that is, steep threshold characteristics and high response speed can be obtained.

BEST MODE FOR CARRYING OUT THE INVENTION

Methods for preparing and using the compounds of the present invention are described in more detail in the following with reference to Examples. In each of the Examples, Cr represents crystal, N does nematic phase, S does smectic phase, and Iso represents isotropic liquid, and all of the unit of phase transition temperature is °C.

EXAMPLE 1

Preparation of 4-(4-(1,5-hexedienyl)cyclohexyl)-1-pentylcycl ohexane

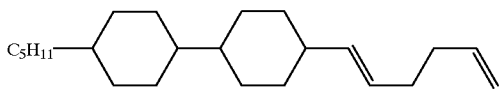

(Compound No. 8 expressed by general formula (1) in which $R_1$ represents pentyl group, $X_3$ represents a covalent bond, C and D represent trans-1,4-cyclohexane ring, l, m, and n are 0, o is 1, p is 2, and $R_2$ and $R_2'$ are hydrogen atom.)

A mixture of a commercially available 1-bromo-5-pentene (600 mmol), triphenylphosphine (500 mmol), and 300 ml of toluene was heated to reflux for 40 hours. White crystals thus precipitated were filtered off, washed with toluene thrice, and then dried under a reduced pressure to obtain a phosphonium salt (500 mmol).

Potassium-t-butoxide (550 mmol) was added to the mixture of the phosphonium salt mentioned above (500 mmol) and 500 ml of tetrahydrofuran (hereinafter referred to as THF), and stirred at room temperature for 2 hours. To the red solution thus obtained was added a solution of 4-(4-pentylcyclohexyl)cyclohexane-carboaldehyde (500 mmol) prepared according to the method of Laid-open Japanese Patent Publication No. Sho 61-83136 in 300 ml of THF at a temperature lower than 0° C., and stirred at room temperature for 4 hours. It was put in 500 ml of water and extracted with 500 ml of toluene, and the organic layer was washed with 2M hydrochloric acid and saturated aqueous solution of sodium bicarbonate, and then washed with water until it became neutral. After it was dried with anhydrous magnesium sulfate, the solvent was distilled off, and the residue was purified with a silica gel column chromatography (eluent: heptane) to obtain 4-(4-(cis-1,5-hexedienyl) cyclohexyl)-1-pentylcyclohexane (250 mmol).

m-Chloroperbenzoic acid (750 mmol) and potassium carbonate (1.5 mol) were added to the solution of the compound mentioned above (250 mmol) in 200 ml of methylene chloride and stirred at room temperature for 8 hours. After 500 ml of saturated aqueous solution of sodium thiosulfate was added to the reaction solution and stirred, the organic layer was washed with water thrice and then dried over anhydrous magnesium sulfate. The solvent was distilled off under a reduced pressure to obtain 4-(4-(cis-1,5-hexedienyl) cyclohexyl)-1-pentyl-cyclohexanedioxide (200 mmol).

Mixture of the epoxide compound mentioned above (200 mmol), triphenylphosphine dibromide (600 mmol), and 200 ml of toluene was stirred under a heated condition for 3 hours. After cooled down, the reaction solution was put in 300 ml of water and extracted with 300 ml of toluene, and the organic layer was washed with 2M hydrochloric acid and saturated aqueous solution of sodium bicarbonate, and then washed with water until it became neutral. After it was dried with anhydrous magnesium sulfate, the solvent was distilled off, and the residue was purified by a silica gel column chromatography (eluent: toluene) and recrystallized by using ethanol 5 times as much as the residue to obtain 100 mmol of 4-(4-(1,2,5,6-tetrabromohexyl) cyclohexyl)-1-pentylcyclohexane.

Mixture of the bromide mentioned above (100 mmol), 800 mmol of metal zinc, and 20 ml of acetic acid was stirred at room temperature for 12 hours. Water in an amount of 100 ml was added, extracted with 50 ml of toluene, and the organic layer was washed with 2N hydrochloric acid and saturated aqueous solution of sodium bicarbonate and then washed with water until it became neutral. After it was dried over anhydrous magnesium sulfate, the solvent was distilled off, and the residue was purified by a silica gel column chromatography (eluent: heptane) and recrystallized twice from ethanol/heptane (1/1) mixed solvent 5 times as much as the residue to obtain 80 mmol of the subject compound. This compound showed smectic at room temperature and had a clearing point of 107.1 to 107.6° C. Also, NMR spectrum, mass spectrum, IR spectrum, and the values of elementary analysis of this compound well supported its structure.

According to the method of Example 1, the following compounds were prepared:

| | R1 | A | X1 | B | X2 | C | X3 | D | W | |
|---|---|---|---|---|---|---|---|---|---|---|
| 1 | CH3 | | | | |  | |  |  | S 28.1 Iso |
| 2 | C2H5 | | | | |  | |  |  | S 64.1 Iso |
| 3 | C3H7 | | | | |  | |  |  | S 86.2 N 88.6 Iso |
| 4 | C3H7 | | | | | | | |  | |
| 5 | C3H7 | | | | | | | |  | |
| 6 | C3H7 | | | | | | | |  | |
| 7 | C4H9 | | | | |  | | |  | S 97.9 Iso |

-continued
| | R1 | A | X1 | B | X2 | C | X3 | D | W | |
|---|---|---|---|---|---|---|---|---|---|---|
| 8 | C5H11 | | | | |  | |  |  | S 107.6 Iso |
| 9 | C3H7 | | | | |  | CH2CH2 |  |  | S 88.2 Iso |
| 10 | C5H11 | | | | |  | CH2CH2 |  |  | |
| 11 | C3H7 | | | | |  | (CH2)4 |  |  | |
| 12 | C5H11 | | | | |  | (CH2)4 | | | |
| 13 | C3H7 | | | | | | | | | |
| 14 | C3H7 | | | | | | | | | Cr-18.8 Iso |
| 15 | C3H7 | | | | |  | |  |  | |

-continued

| R1 | A | X1 | B | X2 | C | X3 | D | W |
|---|---|---|---|---|---|---|---|---|
| 16 NC | | | | | phenyl | | cyclohexyl | (diene) S 56.2 N 67.0 Iso |
| 17 NC | | | | | 4-F-phenyl | | cyclohexyl | (diene) |
| 18 F | | | | | 4-F-phenyl | | cyclohexyl | (diene) |
| 19 F | | | | | 3,5-diF-phenyl | | cyclohexyl | (diene) |
| 20 C3H7 | | | | | phenyl | CH2CH2 | cyclohexyl | (diene) |
| 21 NC | | | | | phenyl | CH2CH2 | cyclohexyl | (diene) |

-continued

| R1 | A | X1 | B | X2 | C | X3 | D | W |
|---|---|---|---|---|---|---|---|---|
| 22 NC | | | | | fluorophenyl | CH2CH2 | cyclohexyl | diene chain |
| 23 F | | | | | fluorophenyl | CH2CH2 | cyclohexyl | diene chain |
| 24 F | | | | | difluorophenyl (3,5) | CH2CH2 | cyclohexyl | diene chain |
| 25 C3H7 | | | | | pyrimidine | | phenyl | diene chain |
| 26 NC | | | | | phenyl | | phenyl | diene chain |
| 27 NC | | | | | pyridazine | | phenyl | diene chain |

-continued

| R1 | A | X1 | B | X2 | C | X3 | D | W |
|---|---|---|---|---|---|---|---|---|
| 28 NC | | | | | (benzene) | | (benzene) | (diene chain) |
| 29 NC | | | | | (benzene) | | (benzene) | (diene chain) |
| 30 NC | | | | | (fluorobenzene) | | (benzene) | (diene chain) |
| 31 C3H7 | | | (cyclohexane) | | (cyclohexane) | | (cyclohexane) | (diene chain) |
| 32 C5H11 | | | (cyclohexane) | | (cyclohexane) | | (cyclohexane) | (CF2 diene chain) |
| 33 C3H7 | | | (1,3-dioxane) | | (cyclohexane) | | (cyclohexane) | (diene chain) |
| 34 C5H11 | | | (benzene) | CH2CH2 | (cyclohexane) | | (cyclohexane) | (diene chain) |

-continued
| | R1 | X1 | B | X2 | C | X3 | D | W |
|---|---|---|---|---|---|---|---|---|
| 35 | NC | |  | CH2CH2 |  | |  |  |
| 36 | F | |  | CH2CH2 |  | |  |  |
| 37 | NC | |  | CH2CH2 |  | |  |  |
| 38 | NC | |  | CH2CH2 |  | |  |  |
| 39 | C3H7 | |  | CH2CH2 |  | CH2CH2 |  |  |
| 40 | C4H9 | |  | CH2CH2 |  | CH2CH2 |  |  |
| 41 | C5H11 | |  | CH2CH2 |  | CH2CH2 |  |  |

-continued

| R1 | A | X1 | B | X2 | C | X3 | D | W |
|---|---|---|---|---|---|---|---|---|
| 42 NC | | | phenyl | CH2CH2 | cyclohexyl | CH2CH2 | cyclohexyl | (diene) |
| 43 NC | | | phenyl | CH2CH2 | cyclohexyl | CH2CH2 | cyclohexyl | (diene) |
| 44 C3H7 | | | phenyl | | cyclohexyl | CH2CH2 | cyclohexyl | (diene) |
| 45 C3H7 | | | phenyl | | cyclohexyl | CH2CH2 | cyclohexyl | (diene with CF2) |
| 46 C4H9 | | | phenyl | | cyclohexyl | CH2CH2 | cyclohexyl | (diene) |
| 47 C5H11 | | | phenyl | | cyclohexyl | CH2CH2 | cyclohexyl | (diene) |
| 48 C7H15 | | | pyridyl | | cyclohexyl | CH2CH2 | cyclohexyl | (diene) |
| 49 F | | | phenyl | | cyclohexyl | CH2CH2 | cyclohexyl | (diene) |

-continued

| | R1 | A | X1 | B | X2 | C | X3 | D | W |
|---|---|---|---|---|---|---|---|---|---|
| 50 | F | | | F-phenyl | | cyclohexyl | CH2CH2 | cyclohexyl | (diene chain) |
| 51 | NC | | | phenyl | | cyclohexyl | CH2CH2 | cyclohexyl | (diene chain) |
| 52 | NC | | | F-phenyl | | cyclohexyl | CH2CH2 | cyclohexyl | (diene chain) |
| 53 | NC | | | 3,5-diF-phenyl | | cyclohexyl | CH2CH2 | cyclohexyl | (diene chain) |
| 54 | NC | | | phenyl | | cyclohexyl | CH2CH2 | cyclohexyl | (diene chain) |
| 55 | C3H7 | | | phenyl | | cyclohexyl | (CH2)4 | cyclohexyl | (diene chain) |

-continued

| | R1 | A | X1 | B | X2 | C | X3 | D | W |
|---|---|---|---|---|---|---|---|---|---|
| 56 | C4H9 | | | benzene | | cyclohexane | (CH2)4 | cyclohexane | diene |
| 57 | C5H11 | | | benzene | | cyclohexane | (CH2)4 | cyclohexane | diene |
| 58 | CH3 | | | benzene | | benzene | | cyclohexane | diene |
| 59 | CH3 | | | benzene | | benzene | | cyclohexane | diene |
| 60 | CH3 | | | benzene | | benzene | | cyclohexane | diene |
| 61 | CH3 | | | benzene | | benzene | | cyclohexane | diene |
| 62 | C2H5 | | | benzene | | benzene | | cyclohexane | diene |
| 63 | C3H7 | | | benzene | | benzene | | cyclohexane | diene |

Compound 62: S 161.5 Iso

-continued

| | R1 | A | X1 | B | X2 | C | X3 | D | W | |
|---|---|---|---|---|---|---|---|---|---|---|
| 64 | C4H9 | | | phenyl | | phenyl | | cyclohexyl | diene | |
| 65 | C5H11 | | | phenyl | | phenyl | | cyclohexyl | diene | |
| 66 | F | | | phenyl | | phenyl | | cyclohexyl | diene | |
| 67 | NC | | | phenyl | | phenyl | | cyclohexyl | diene | 122.5 S 129.2 N 209.7 Iso |
| 68 | Cl | | | phenyl | | phenyl | | cyclohexyl | diene | |
| 69 | Cl | | | F-phenyl | | phenyl | | cyclohexyl | diene | |
| 70 | F | | | phenyl | | phenyl | | cyclohexyl | diene | |

| R1 | A | X1 | B | X2 | C | X3 | D | W |
|---|---|---|---|---|---|---|---|---|
| 71 F | | | fluorophenyl | | phenyl | | cyclohexyl | diene chain |
| 72 F | | | difluorophenyl | | phenyl | | cyclohexyl | diene chain |
| 73 CH3 | | | phenyl | | phenyl | CH2CH2 | cyclohexyl | diene chain |
| 74 C2H5 | | | phenyl | | phenyl | CH2CH2 | cyclohexyl | diene chain |
| 75 C3H7 | | | phenyl | | phenyl | CH2CH2 | cyclohexyl | diene chain |
| 76 F | | | phenyl | | phenyl | CH2CH2 | cyclohexyl | diene chain |
| 77 NC | | | phenyl | | phenyl | CH2CH2 | cyclohexyl | diene chain |

-continued
| R1 | A | X1 | B | X2 | C | X3 | D | W |
|---|---|---|---|---|---|---|---|---|
| 78 NC | | |  | |  | CH2CH2 |  |  |
| 79 | | |  | |  | (CH2)4 |  |  |
| 80 C5H11 | | |  | |  | (CH2)4 |  |  |
| 81 C3H7 | | |  | |  | |  |  |
| 82 F | | |  | |  | |  |  |
| 83 C3H7 | | |  | |  | CH2CH2 |  | |
| 84 C5H11 | | | | | | CH2CH2 | | |

-continued

| | R1 | A | X1 | B | X2 | C | X3 | D | W |
|---|---|---|---|---|---|---|---|---|---|
| 85 | C5H11 | | | ⬡ | | ⬡ | CH2CH2 | ⬡ | (diene chain) |
| 86 | C5H11 | | | ⬡ | | ⬡ | CH2CH2 | ⬡ | (alkenyl chain) |
| 87 | C5H11 | | | ⬡ | | ⬡ | CH2CH2 | ⬡ | (alkenyl chain) |
| 88 | C2H5 | | | ⬡ | CH2CH2 | ⬡ | CH2CH2 | ⬡ | (alkenyl chain) |
| 89 | C3H7 | | | ⬡ | CH2CH2 | ⬡ | CH2CH2 | pyrazine | (alkenyl chain) |
| 90 | C4H9 | | | ⬡ | CH2CH2 | ⬡ | CH2CH2 | ⬡ | (alkenyl chain) |
| 91 | C5H11 | | | ⬡ | CH2CH2 | ⬡ | CH2CH2 | ⬡ | (alkenyl chain) |
| 92 | C9H19 | | | ⬡ | CH2CH2 | ⬡ | CH2CH2 | ⬡ | (alkenyl chain) |

-continued

| | R1 | A | X1 | B | X2 | C | X3 | D | W |
|---|---|---|---|---|---|---|---|---|---|
| 93 | C3H7 | | | cyclohexyl | | cyclohexyl | (CH2)4 | phenyl | diene chain |
| 94 | C5H11 | | | cyclohexyl | | cyclohexyl | (CH2)4 | phenyl | CF2 diene chain |
| 95 | C3H7 | | | cyclohexyl | | cyclohexyl | (CH2)4 | phenyl | diene chain |
| 96 | C3H7 | | | cyclohexyl | | cyclohexyl | (CH2)4 | phenyl | diene chain |
| 97 | C3H7 | | | cyclohexyl | | phenyl | | phenyl | diene chain |
| 98 | C3H7 | | | cyclohexyl | | phenyl | | phenyl | diene chain |
| 99 | C3H7 | | | cyclohexyl | | phenyl | | phenyl | diene chain |
| 100 | C3H7 | | | cyclohexyl | | phenyl | | phenyl | diene chain |

-continued

| | R1 | A | X1 | B | X2 | C | X3 | D | W |
|---|---|---|---|---|---|---|---|---|---|
| 101 | C3H7 | | | cyclohexane | | benzene | | benzene | alkenyl |
| 102 | C5H11 | | | cyclohexane | | F-benzene | | benzene | alkenyl |
| 103 | C3H7 | | | cyclohexane | CH2CH2 | benzene | | benzene | alkenyl |
| 104 | C4H9 | | | cyclohexane | CH2CH2 | benzene | | benzene | alkenyl |
| 105 | C5H11 | | | cyclohexane | CH2CH2 | benzene | | benzene | alkenyl |
| 106 | C2H5 | benzene | | cyclohexane | | cyclohexane | | cyclohexane | alkenyl |
| 107 | CH3OCH2 | benzene | | cyclohexane | | cyclohexane | | cyclohexane | alkenyl |
| 108 | F | benzene | | cyclohexane | | cyclohexane | | cyclohexane | alkenyl |
| 109 | NC | benzene | | cyclohexane | | cyclohexane | | cyclohexane | alkenyl |

-continued

| R1 | A | X1 | B | X2 | C | X3 | D | W |
|---|---|---|---|---|---|---|---|---|
| 110 CH3 | phenyl | | phenyl | CH2CH2 | cyclohexyl | | cyclohexyl | diene chain |
| 111 C5H11 | phenyl | | phenyl | CH2CH2 | cyclohexyl | | cyclohexyl | diene chain |
| 112 C5H11 | phenyl | | phenyl | CH2CH2 | cyclohexyl | | cyclohexyl | diene chain |
| 113 C2H5OCH2 | phenyl | | phenyl | CH2CH2 | cyclohexyl | | cyclohexyl | diene chain |
| 114 C2H5OCH2 | phenyl | | phenyl | CH2CH2 | cyclohexyl | | cyclohexyl | diene chain |
| 115 C3H7OCH2 | phenyl | | phenyl | CH2CH2 | cyclohexyl | | cyclohexyl | diene chain |
| 116 F | phenyl | | phenyl | CH2CH2 | cyclohexyl | | cyclohexyl | diene chain |
| 117 F | F-phenyl | | phenyl | CH2CH2 | cyclohexyl | | cyclohexyl | diene chain |

| | R1 | A | X1 | B | X2 | C | X3 | D | W |
|---|---|---|---|---|---|---|---|---|---|
| 118 | F | 3,5-F2-phenyl | | phenyl | CH2CH2 | cyclohexyl | | cyclohexyl | |
| 119 | F | F-phenyl | | F-phenyl | | cyclohexyl | | cyclohexyl | |
| 120 | NC | phenyl | | phenyl | CH2CH2 | cyclohexyl | | cyclohexyl | |
| 121 | C3H7 | phenyl | | phenyl | | cyclohexyl | CH2CH2 | cyclohexyl | |
| 122 | C3H7 | phenyl | | phenyl | | cyclohexyl | CH2CH2 | cyclohexyl | |
| 123 | C3H7 | phenyl | | phenyl | | cyclohexyl | (CH2)4 | cyclohexyl | |
| 124 | C5H11 | phenyl | | phenyl | | cyclohexyl | (CH2)4 | cyclohexyl | |
| 125 | C3H7 | phenyl | | phenyl | | phenyl | | cyclohexyl | |

-continued

| R1 | A | X1 | B | X2 | C | X3 | D | W |
|---|---|---|---|---|---|---|---|---|
| 126 C5H11 | phenyl | | phenyl | | phenyl | | cyclohexyl | |
| 127 F | phenyl | | phenyl | | phenyl | | cyclohexyl | |
| 128 F | phenyl | | F-phenyl | | phenyl | | cyclohexyl | |
| 129 C4H9 | phenyl | | phenyl | CH2CH2 | phenyl | | cyclohexyl | |
| 130 C5H11 | phenyl | | phenyl | CH2CH2 | phenyl | | cyclohexyl | |
| 131 CH3 | cyclohexyl | | phenyl | | phenyl | | cyclohexyl | |
| 132 C3H7 | cyclohexyl | | phenyl | | phenyl | | cyclohexyl | |
| 133 C3H7 | cyclohexyl | | phenyl | | phenyl | | cyclohexyl | |
| 134 C3H7 | cyclohexyl | | phenyl | | phenyl | | cyclohexyl | |

-continued
| | R1 | A | X1 | B | X2 | C | X3 | D | W |
|---|---|---|---|---|---|---|---|---|---|
| 135 | C3H7 |  | |  | |  | |  |  |
| 136 | C3H7 |  | |  | |  | |  |  |
| 137 | C3H7 |  | |  | |  | |  |  |
| 138 | C5H11 |  | |  | |  | |  |  |
| 139 | C5H11 |  | |  | |  | |  |  |
| 140 | C5H11 |  | |  | |  | |  |  |
| 141 | C5H11 |  | |  | |  | |  |  |
| 142 | C2H5OCH2 |  | |  | |  | |  |  |

-continued
| | R1 | A | X1 | B | X2 | C | X3 | D | W |
|---|---|---|---|---|---|---|---|---|---|
| 143 | C3H7OCH2 |  | |  | |  | |  |  |
| 144 | C3H7OCH2 |  | |  | |  | |  |  |
| 145 | C3H7 |  | |  | |  | CH2CH2 |  |  |
| 146 | C3H7 |  | |  | |  | CH2CH2 |  |  |
| 147 | C3H7 |  | |  | |  | |  |  |
| 148 | C5H11 |  | |  | |  | |  |  |
| 149 | C3H7 |  | |  | CH2CH2 |  | |  |  |
| 150 | C5H11 |  | |  | CH2CH2 |  | |  | |
| 151 | C3H7 | | CH2CH2 | | | | | | |

-continued

| | R1 | A | X1 | B | X2 | C | X3 | D | W |
|---|---|---|---|---|---|---|---|---|---|
| 152 | C5H11 | ⬡ | CH2CH2 | ⬡ | | ⬡ | | ⌬ | |
| 153 | C3H7 | ⬡ | (CH2)4 | ⬡ | | ⬡ | | ⌬ | |
| 154 | C5H11 | ⬡ | (CH2)4 | ⬡ | | ⬡ | | ⌬ | |
| 155 | CH3 | ⬡ | | ⬡ | | ⌬ | | ⌬ | |
| 156 | C3H7 | ⬡ | | ⬡ | | ⌬ | | ⌬ | |
| 157 | C3H7 | ⬡ | | ⬡ | | ⌬ | | ⌬ | |
| 158 | C3H7 | ⬡ | | ⬡ | | ⌬ | | ⌬ | |
| 159 | C5H11 | ⬡ | | ⬡ | | ⌬ | | ⌬ | |
| 160 | C5H11 | ⬡ | | ⬡ | | ⌬ | | ⌬ | |

-continued
| | R1 | A | X1 | B | X2 | C | X3 | D | W |
|---|---|---|---|---|---|---|---|---|---|
| 161 | C5H11 |  | |  | |  | |  |  |
| 162 | C5H11 |  | |  | |  | |  |  |
| 163 | C3H7OCH2 |  | |  | |  | |  |  |
| 164 | CH3OCH2CH2 |  | | 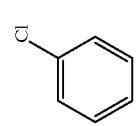 | |  | |  |  |
| 165 | FCH2 |  | |  | |  | |  |  |
| 166 | C3H7 |  | |  | CH2CH2 |  | |  |  |
| 167 | C3H7 |  | |  | CH2CH2 |  | |  |  |
| 168 | C5H11 |  | |  | CH2CH2 |  | |  |  |

-continued

| | R1 | A | X1 | B | X2 | C | X3 | D | W | |
|---|---|---|---|---|---|---|---|---|---|---|
| 178 | F | | | fluorophenyl | | cyclohexyl | | cyclohexyl | diene chain | Cr 39.3 N 144.9 Iso |
| 179 | F | | | difluorophenyl | | cyclohexyl | | cyclohexyl | diene chain | Cr 90.9 N 117.0 Iso |
| 180 | NC | | | phenyl | | cyclohexyl | | cyclohexyl | diene chain | Cr 75.6 N 257.7 Iso |

EXAMPLE 2

Preparation of 4-(2-(4-(4-propylphenyl)cyclohexyl)ethenyl-1-(1,5-hexedienyl)cyclohexane

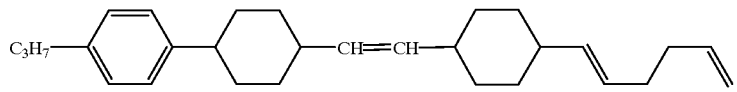

(Compound No. 187 expressed by general formula (1) wherein $R_1$ represents propyl group, $X_2$ represents a covalent bond, X3 represents —CH=CH—, B represents 1,4-phenylene ring, C and D represent trans-1,4-cyclohexane ring, l and n are 0, m and o are 1, p is 2, and $R_2$ and $R_2'$ are hydrogen atom.)

Mixture of methoxymethyltriphenylphosphonium chloride (1 mol), potassium-t-butoxide (1 mol), and 1 l of THF was stirred at room temperature for 2 hours. To this mixture was added dropwise the solution of a commercially available 1,4-dioxyspiro[4,5]deca-8-one (1 mol) in 500 ml of THF at a temperature lower than 0° C. After stirred at room temperature for 4 hours, it was put in 500 ml of water and extracted with 500 ml of toluene. The organic layer was washed with 2M hydrochloric acid and saturated aqueous solution of sodium bicarbonate, and then washed with water until it became neutral. After dried with anhydrous magnesium sulfate, the solvent was distilled off, and the residue was treated by a silica gel column chromatography (eluent: toluene), and the solvent was distilled off under a reduced pressure. To the residue thus obtained was added 500 ml of 6M hydrochloric acid and 1 l of THF, it was stirred at room temperature for 12 hours, and then the organic layer was washed with water thrice. The solvent was distilled off under a reduced pressure to obtain 870 mmol of 1,4-dioxaspiro [4.5] decane-8-carboaldehyde as residue.

After the 4-(4-propylphenyl)cyclohexanecarboxylic acid prepared according to the method described in U.S. Pat. No. 4,229,315 was subjected to a reduction and halogenation according to the methods of M. J. Jorgensen et al., J. Am. Chem. Soc., 87, 1815 (1965) and O. Kamm et al., Synth. Col. I, 25 (1941), the solution of the 4-(4-propylphenyl)cyclohexylmethyl bromide (950 mmol) thus obtained in 500 ml of THF was added dropwise under reflux to the mixture of metal magnesium (950 ml) and 50 ml of THF to prepare a Gregnard reagent. To this solution was added dropwise at a temperature lower than 0° C. the solution of the 1,4-dioxaspiro[4,5]decane-8-carboaldehyde (870 mol) prepared by previous procedures in 500 ml of THF, and further they were stirred at room temperature for 2 hours. Reaction product was brought to a temperature lower than 0° C. again, 500 ml of saturated aqueous solution of ammonium chloride was added to the reaction product, and they were stirred for 1 hour and then extracted with 1 l of toluene. After the organic layer was washed with water thrice and dried over anhydrous magnesium sulfate, the organic solvent was distilled off under a reduced pressure. The residue was dissolved in 1 l of toluene, p-toluenesulfonic acid (40 mmol) was added to the solution, and it was refluxed while removing resulted water for 3 hours. After allowed to cool, the toluene layer was washed with water thrice and the solvent was distilled off under a reduced pressure to obtain 670 mmol of 4-(2-(4-(4-propylphenyl) cyclohexyl)ethenyl) cyclohexanone.

Mixture of methoxymethyltriphenylphosphonium chloride (730 mol), potassium-t-butoxide (730 mol), and 700 ml of THF was stirred at room temperature for 2 hours, and the solution of the 4-(2-(4-(4-propylphenyl)cyclohexyl)ethenyl) cyclohexanone (670 mmol) obtained by the previous procedures in 500 ml of THF was added dropwise to the mixture at a temperature lower than 0° C. After stirred at room temperature for 4 hours, it was put in 500 ml of water and extracted with 500 ml of toluene, and the organic layer was washed with 2M hydrochloric acid and saturated bicarbonate and washed with water until it became neutral. After it was dried with anhydrous magnesium sulfate, the solvent was distilled off, the residue was treated by a silica gel column chromatography (eluent: toluene), and the solvent was distilled off under a reduced pressure. To the residue thus obtained were added 500 ml of 6M hydrochloric acid and 1 l of THF, they were stirred at room temperature for 12 hours, and the organic layer was washed with water thrice. The solvent was distilled off under a reduced pressure, and the residue was purified by a silica gel column chromatography (eluent: toluene) to obtain 4-(2-(4-(4-propylphenyl) cyclohexyl)ethenyl) cyclohexanecarboaldehyde (410 mmol).

The phosphonium salt of 1-bromo-5-pentene obtained in Example 1 was reacted with 410 mmol of the 4-(2-(4-(4-propyl-phenyl)cyclohexyl)ethenyl) cyclohexanecarboaldehyde, and then subjected to an epoxidation, bromination, and reduction according to the methods in Example 1 to obtain 64 mmol of the subject compound. NMR spectrum, mass spectrum, IR spectrum, and the values of elementary analysis of this compound well supported its structure.

According to the method of Example 2, the following compounds were prepared:

| | R1 | A | X1 | B | X2 | C | X3 | D | W |
|---|---|---|---|---|---|---|---|---|---|
| 181 | C$_3$H$_7$ | | | | | ⬡ | CH=CH | ⬡ | ⟋⟍⟋⟍ |

| | R1 | A | X1 | B | X2 | C | X3 | D | W |
|---|---|---|---|---|---|---|---|---|---|
| 182 | C₃H₇ | | | | |  | CH=CH |  | 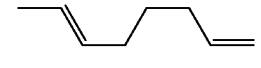 |
| 183 | C₃H₇ | | | | |  | CH=CH |  | 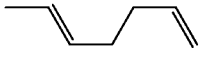 |
| 184 | C₅H₁₁ | | | | |  | CH=CH |  | 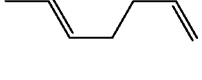 |
| 185 | C₃H₇ | | | | |  | CH=CH |  | 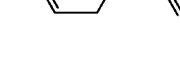 |
| 186 | C₅H₁₁ | | | | |  | CH=CH |  | 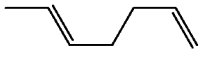 |
| 187 | C₃H₇ | | |  | |  | CH=CH |  |  |
| 188 | C₃H₇ | | |  | |  | CH=CH |  |  |
| 189 | C₃H₇ | | |  | |  | CH=CH |  |  |
| 190 | C₅H₁₁ | | |  | |  | CH=CH |  |  |
| 191 | CH₃ | | |  | |  | CH=CH |  |  |
| 192 | C₃H₇ | | | | | | CH=CH | | |
| 193 | C₃H₇ | | | | | | CH=CH | |  |

-continued
| | R1 | A | X1 | B | X2 | C | X3 | D | W |
|---|---|---|---|---|---|---|---|---|---|
| 194 | C₃H₇ | | |  | |  | CH=CH |  | 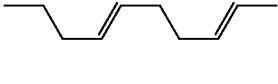 |
| 195 | C₃H₇ | | |  | |  | CH=CH |  | 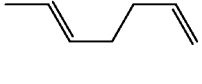 |
| 196 | C₃H₇ | | |  | |  | CH=CH |  | 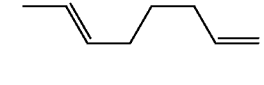 |
| 197 | C₄H₉ | | |  | |  | CH=CH |  | 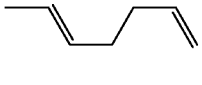 |
| 198 | C₅H₁₁ | | |  | |  | CH=CH |  | 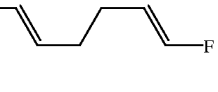 |
| 199 | C₃H₇OCH₂ | | |  | |  | CH=CH |  | 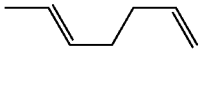 |
| 200 | C₅H₁₁OCH₂ | | |  | |  | CH=CH |  | 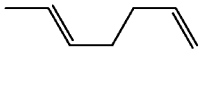 |
| 201 | CH₃OCH₂CH₂ | | |  | |  | CH=CH |  | 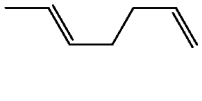 |
| 202 | CH₃OCH₂CH₂CH₂ | | |  | |  | CH=CH |  | 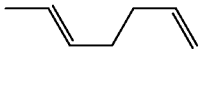 |
| 203 | FCH₂CH₂ | | |  | |  | CH=CH |  | 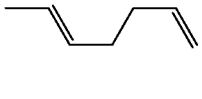 |
| 204 | FCH₂CH₂CH₂ | | |  | |  | CH=CH |  | 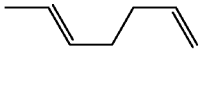 |
EXAMPLE 3
Preparation of 4-(2-(4-methylphenyl)ethynyl)-1-(1,5-hexadienyl)benzene

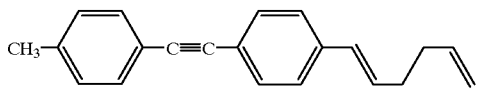

(Compound No. 205 expressed by general formula (1) wherein $R_1$ represents methyl group, $X_3$ represents —C≡C—, C and D represent trans-1,4-cyclohexane ring, l, m, and n are 0, o is 1, p is 2, and $R_2$ and $R_2'$, are hydrogen atom.)

According to the method of J. Cole et al., J. Chem. Soc., 244 (1962), a mixture of toluylacetylene (200 mmol), 2-(4-bromophenyl)-1,3-dioxalane (200 mmol), dimethylformamide (500 ml), and copper iodide (I) (300 mmol) was heated while stirring for 5 hours. After allowed to cool, 500 ml of 6M hydrochloric acid was added and stirred for 1 hour. It was extracted with 500 ml of toluene, and the organic layer was washed with water thrice and dried with anhydrous magnesium sulfate. The solvent was distilled off and the residue was purified by a silica gel column chromatography (eluent: toluene) to obtain 120 mmol of 4-(2-(4-ethynyl)benzaldehyde.

Solution of phenyllithium (corresponding to 125 mmol) in hexane was added dropwise at −78° C. to the mixture of the phosphonium salt of 1-bromo-5-pentene (125 mmol) prepared in Example 1 and 300 ml of THF, and stirred at the same temperature for 1 hour. To this mixture was added dropwise the solution of the 4-(2-(4-ethynyl)benzaldehyde (120 mmol) obtained by previous procedures in 500 ml of THF while keeping it at −78° C. To the reaction solution was carefully added 50 ml of water and it was gradually brought back to room temperature. Further, 100 ml of water was added, extracted with 100 ml of toluene, and the organic layer was washed with 2N hydrochloric acid and saturated aqueous solution of sodium bicarbonate, and washed with water until it became neutral. After it was dried with anhydrous magnesium sulfate, the solvent was distilled off, and the residue was purified by a silica gel column chromatography (eluent: heptane) to obtain the subject compound (19 mmol). NMR spectrum, mass spectrum, IR spectrum, and the values of elementary analysis of this compound well supported its structure.

According to the method of Example 3, the following compounds were prepared:

| | R1 | A | X1 | B | X2 | C | X3 | D | W |
|---|---|---|---|---|---|---|---|---|---|
| 205 | $CH_3$ | | | | | ⬡ | C≡C | ⬡ | ⁓⁓⁓ |
| 206 | $C_3H_7$ | | | | | ⬡ | C≡C | ⬡ | ⁓⁓⁓ |
| 207 | $C_4H_9$ | | | | | ⬡ | C≡C | ⬡ | ⁓⁓⁓ |
| 208 | $C_5H_{11}$ | | | | | ⬡ | C≡C | ⬡ | ⁓⁓⁓ |
| 209 | $C_5H_{11}$ | | | | | ⬡ | C≡C | ⬡ | ⁓⁓⁓ |
| 210 | $C_5H_{11}$ | | | | | ⬡ | C≡C | ⬡ | ⁓⁓⁓ |
| 211 | $C_5H_{11}$ | | | | | ⬡ | C≡C | ⬡ | ⁓⁓⁓ |

-continued
| | R1 | A | X1 | B | X2 | C | X3 | D | W |
|---|---|---|---|---|---|---|---|---|---|
| 212 | C$_3$H$_7$ | | |  | C≡C |  | |  | 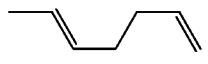 |
| 213 | C$_3$H$_7$ | | |  | C≡C |  | |  | 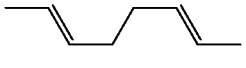 |
| 214 | C$_3$H$_7$ | | |  | C≡C |  | |  | 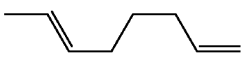 |
| 215 | C$_4$H$_9$ | | |  | C≡C |  | |  | 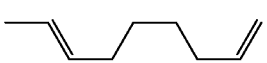 |
| 216 | C$_5$H$_{11}$ | | |  | C≡C |  | |  | 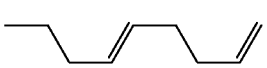 |
| 217 | C$_5$H$_{11}$ | | |  | C≡C |  | |  | 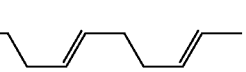 |
| 218 | C$_3$H$_7$ | | |  | |  | C≡C |  |  |
| 219 | C$_3$H$_7$ | | |  | |  | C≡C |  | 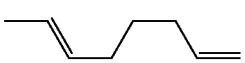 |
| 220 | C$_4$H$_9$ | | |  | |  | C≡C |  |  |
| 221 | C$_5$H$_{11}$ | | |  | |  | C≡C |  | 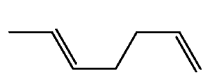 |
| 222 | C$_5$H$_{11}$ | | |  | |  | C≡C |  | 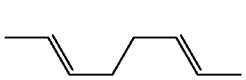 |
| 223 | C$_5$H$_{11}$ | | |  | |  | C≡C |  | 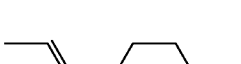 |

-continued

| | R1 | A | X1 | B | X2 | C | X3 | D | W |
|---|---|---|---|---|---|---|---|---|---|
| 224 | C$_5$H$_{11}$ | | | ⬡ | | ⬢ | C≡C | ⬡ | ∕∖∕∕ |
| 225 | CH$_3$OCH$_2$CH$_2$ | | | ⬡ | | ⬢ | C≡C | ⬡ | ∕∖∕∕ |
| 226 | CH$_3$OCH$_2$CH$_2$CH$_2$ | | | ⬡ | | ⬢ | C≡C | ⬡ | ∕∖∕∕ |
| 227 | FCH$_2$CH$_2$ | | | ⬡ | | ⬢ | C≡C | ⬡ | ∕∖∕∕ |
| 228 | FCH$_2$CH$_2$CH$_2$ | | | ⬡ | | ⬢ | C≡C | ⬡ | ∕∖∕∕ |

EXAMPLE 4

Preparation of 4-(1,5-hexadienyl)phenyl-4-propylbenzoate

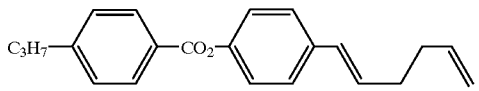

(Compound No. 229 expressed by general formula (1) wherein R$_1$ represents propyl group, X$_3$ represents —CO$_2$—, C and D represent trans-1,4-cyclohexane ring, l, m, and n are 0, o is 1, p is 2, and R$_2$ and R$_2$' are hydrogen atom.)

Potassium-t-butoxide (100 mmol) was added to the mixture of the phosphonium salt of 1-bromo-5-pentene (100 mmol) prepared in Example 1 and 200 ml of THF, and stirred at room temperature for 1 hour. To this mixture was added dropwise a solution of a commercially available 4-hydroxybenzaldehyde (90 mmol) in 100 ml of THF while keeping it at 0° C. After it was stirred at the same temperature for 2 hours, the reaction solution was put in 100 ml of water, and extracted with 200 ml of ether, and the organic layer was washed with water until it became neutral. After it was dried over anhydrous magnesium sulfate, the solvent was distilled off, and the residue was purified by a silica gel column chromatography (eluent: ethyl acetate) to obtain 70 mmol of 4-(cis-1,5-hexedienyl)phenol.

m-Chloroperbenzoic acid (210 mmol) and potassium carbonate (420 mmol) were added to the solution of the compound mentioned above (70 mmol) in 210 ml of methylene chloride and stirred at room temperature for 8 hours. After 200 ml of saturated aqueous solution of sodium thiosulfate was added to the reaction solution and stirred, the organic layer was washed with water thrice and then dried over anhydrous magnesium sulfate. The solvent was distilled off under a reduced pressure to obtain 4-(cis-1,5-hexedienyl)phenoldioxide (50 mmol).

Mixture of the epoxide (50 mmol) mentioned above, dibromotriphenylphosphine dibromide (150 mmol), and 80 ml of toluene was heated while stirring for 3 hours. After cooled down, the reaction solution was put in 300 ml of water, and extracted with 60 ml of ether, and the organic layer was washed with 2M hydrochloric acid and saturated aqueous solution of sodium bicarbonate and washed with water until it became neutral. After it was dried over anhydrous magnesium sulfate, the solvent was distilled off, and the residue was purified by a silica gel column chromatography (eluent: ethyl acetate) to obtain 4-(1,2,5,6-tetrabromohexyl)phenol (25 mmol).

Mixture of the bromide (25 mmol) mentioned above, 200 mmol of metal zinc, and 5 ml of acetic acid was stirred at room temperature for 12 hours. Water in an amount of 25 ml was added and extracted with 25 ml of ether, and the organic layer was washed with water until it became neutral. After it was dried with anhydrous magnesium sulfate, the solvent was distilled off, and the residue was purified by a silica gel column chromatography (eluent: ethyl acetate) to obtain oily 4-(1,5-hexadienyl)phenol (20 mmol).

Mixture of the 4-(1,5-hexadienyl)phenol (20 mmol) mentioned above, 4-propylbenzoic acid (20 mmol), dicyclohexylcarbodiimide (20 mmol), dimethylaminopyridine (1 mmol), and 10 ml of methylene chloride was stirred at room temperature for 20 hours. The urea derivative thus precipitated was filtered off, the solvent was distilled off under a reduced pressure, and the residue was purified by a silica gel column chromatography (eluent: toluene) to obtain the subject compound in white solid state (13 mmol). NMR spectrum, mass spectrum, IR spectrum, and the values of elementary analysis of this compound well supported its structure.

According to the method of Example 4, the following compounds were prepared:

| | R1 | A | X1 | B | X2 | C | X3 | D | W |
|---|---|---|---|---|---|---|---|---|---|
| 229 | C₃H₇ | | | | |  | COO |  | 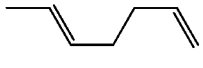 |
| 230 | C₃H₇ | | | | |  | COO |  | 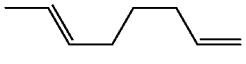 |
| 231 | C₅H₁₁ | | | | |  | COO |  | 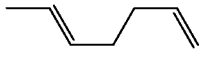 |
| 232 | C₃H₇ | | | | |  | OCO |  |  |
| 233 | C₅H₁₁ | | | | |  | OCO |  | 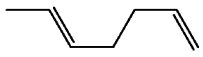 |
| 234 | C₃H₇ | | |  | OCO |  | |  |  |
| 235 | C₄H₉ | | |  | OCO | 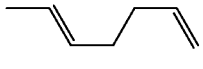 | |  |  |
| 236 | C₅H₁₁ | | | 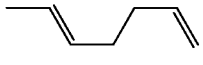 | OCO |  | |  | 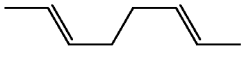 |
| 237 | C₅H₁₁ | | |  | OCO |  | |  |  |
| 238 | CH₃ | | |  | COO |  | |  |  |
| 239 | C₃H₇ | | |  | COO | | | | |
| 240 | C₂H₅ | | | | OCO | | | | |

-continued
| | R1 | A | X1 | B | X2 | C | X3 | D | W |
|---|---|---|---|---|---|---|---|---|---|
| 241 | C₃H₇ | | |  | OCO |  | |  | 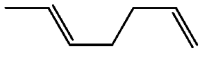 |
| 242 | C₃H₇ | | |  | |  | OCO |  | 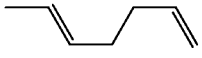 |
| 243 | C₅H₁₁ | | |  | |  | OCO |  | 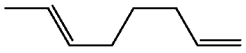 |
| 244 | C₃H₇ | | |  | |  | COO |  |  |
| 245 | C₅H₁₁ | | |  | |  | COO |  |  |
| 246 | CH₃OCH₂ | | |  | |  | COO |  |  |
| 247 | C₅H₁₁ | | |  | |  | COO |  | 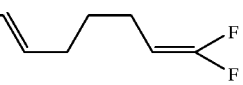 |
| 248 | C₃H₇ | | |  | |  | OCO |  |  |
| 249 | CH₃OCH₂CH₂ | | |  | |  | OCO |  |  |
| 250 | FCH₂CH₂ | | |  | |  | OCO |  |  |
| 251 | C₃H₇ |  | |  | OCO |  | |  |  |
| 252 | C₅H₁₁ |  | |  | OCO |  | | | |

-continued

| | R1 | A | X1 | B | X2 | C | X3 | D | W |
|---|---|---|---|---|---|---|---|---|---|
| 253 | C₃H₇ | ⬡ | COO | ⬡ | | ⬡ | | ⬡ | ∕=∖∕∖= |
| 254 | C₃H₇ | ⬡ | | ⬡ | OCO | ⬡ | | ⬡ | ∕=∖∕∖= |
| 255 | C₅H₁₁ | ⬡ | | ⬡ | OCO | ⬡ | | ⬡ | ∕=∖∕∖= |
| 256 | C₃H₇ | ⬡ | | ⬡ | | ⬡ | OCO | ⬡ | ∕=∖∕∖= |
| 257 | C₅H₁₁ | ⬡ | | ⬡ | | ⬡ | OCO | ⬡ | ∕=∖∕∖= |

EXAMPLE 5

Preparation of 4-(4-(4-propylcyclohexyl)phenyldifluoromethoxy)-1-(1,5-hexadienyl)benzene

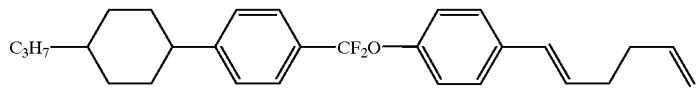

(Compound No. 270 expressed by general formula (1) wherein $R_1$ represents propyl group, $X_2$ represents a covalent bond, $X_3$ represents —$CF_2O$—, B represents trans-1,4-cyclohexane ring, C and D represent 1,4-phenylene ring, l and n are 0, m and o are 1, p is 2, and $R_2$ and $R_2'$ are hydrogen atom.)

Solution of 4-(4-propylcyclohexyl)bromobenzene (200 ml) in 100 ml of THF was gradually added dropwise to a mixture of metal magnesium (210 mmol) and 10 ml of THF and then further heated under reflux for 1 hour to obtain a grey Grignard reagent. To this reagent was added carbon disulfide (600 mmol) at a temperature lower than 0° C. and then stirred for further 2 hours. Water in an amount of 500 ml was added and extracted with 100 ml of ether thrice. The organic layer was washed with a brine solution twice and dried with magnesium sulfate. The solvent was distilled off under a reduced pressure and the residue was recrystallized from toluene to obtain 98 mmol of 4-(4-propylcyclohexyl)thiobenzoic acid.

After the mixture of the thiobenzoic acid (98 mmol) mentioned above and thionyl chloride (500 mmol) was stirred at 50° C. for 5 hours, an excess amount of thionyl chloride was distilled off under a reduced pressure to obtain 97 mmol of corresponding acid chloride.

Acid chloride (97 mmol) obtained by the preceding procedures was added at a temperature lower than 0° C. to the solution of the 4-(1,5-hexadienyl)phenol (80 mmol) prepared in Example 4 in 200 ml of pyridine, and stirred at room temperature for 10 hours. Water in an amount of 500 ml and 200 ml of toluene were added to the solution and stirred. After the organic layer was washed with 200 ml of 2M hydrochloric acid and 200 ml of saturated aqueous solution of sodium bicarbonate, and then washed with water until it became neutral, it was dried with anhydrous magnesium sulfate. The solvent was distilled off under a reduced pressure and the residue was recrystallized from ethanol 5 times as much as the residue to obtain 4-(1,5-hexadienyl)phenyl-4-(4-propylcyclohexyl)thiobenzoate (61 mmol).

After diethylaminosulfurtrifluoride (122 mmol) was gradually added at −20° C to the solution of the 4-(1,5-hexadienyl)phenyl-4-(4-propylcyclohexyl)thiobenzoate (61 mmol) in 50 ml of methylene chloride, they were gradually brought back to room temperature and stirred at the same temperature for 3 hours. After 50 ml of water was added to the solution and stirred, the organic layer was washed with water thrice and dried with anhydrous magnesium sulfate. The solvent was distilled off and the residue was purified by a silica gel column chromatography (eluent: heptane) and then recrystallized from ethanol 5 times as much as the residue to obtain the subject compound in white solid state (32 mmol). NMR spectrum, mass spectrum, IR spectrum, and the values of elementary analysis of this compound well supported its structure.
According to the method of Example 5, the following compounds were prepared:
| | R1 | A | X1 | B | X2 | C | X3 | D | W |
|---|---|---|---|---|---|---|---|---|---|
| 258 | C$_3$H$_7$ | | | | |  | CF$_2$O |  |  |
| 259 | C$_3$H$_7$ | | | | |  | CF$_2$O |  |  |
| 260 | C$_5$H$_{11}$ | | | | |  | CF$_2$O |  |  |
| 261 | C$_3$H$_7$ | | | | |  | OCF$_2$ |  | 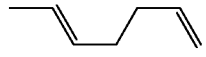 |
| 262 | C$_5$H$_{11}$ | | | | |  | OCF$_2$ |  | 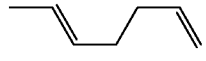 |
| 263 | C$_3$H$_7$ | | |  | OCF$_2$ |  | | 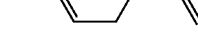 |  |
| 264 | C$_4$H$_9$ | | |  | OCF$_2$ |  | |  |  |
| 265 | C$_5$H$_{11}$ | | | 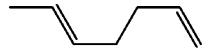 | OCF$_2$ |  | |  |  |
| 266 | C$_5$H$_{11}$ | | |  | OCF$_2$ | | | |  |
| 267 | CH$_3$ | | | 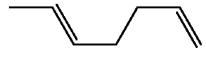 | CF$_2$O | | | |  |
| 268 | C$_3$H$_7$ | | |  | CF$_2$O | | | | 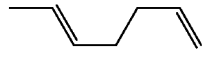 |

-continued

| | R1 | A | X1 | B | X2 | C | X3 | D | W |
|---|---|---|---|---|---|---|---|---|---|
| 269 | C$_2$H$_5$ | | | ⬡ | | ⬡ | CF$_2$O | ⬡ | ⌇ |
| 270 | C$_3$H$_7$ | | | ⬡ | | ⬡ | CF$_2$O | ⬡ | ⌇ |
| 271 | C$_3$H$_7$ | | | ⬡ | | ⬡ | OCF$_2$ | ⬡ | ⌇ |
| 272 | C$_5$H$_{11}$ | | | ⬡ | | ⬡ | OCF$_2$ | ⬡ | ⌇ |
| 273 | C$_3$H$_7$ | ⬡ | CF$_2$O | ⬡ | | ⬡ | | ⬡ | ⌇ |
| 274 | C$_5$H$_{11}$ | ⬡ | OCF$_2$ | ⬡ | | ⬡ | | ⬡ | ⌇ |
| 275 | C$_3$H$_7$ | | | ⬡ | | ⬡ | CF$_2$O | ⬡ | ⌇ |
| 276 | C$_5$H$_{11}$ | | | ⬡ | | ⬡ | OCF$_2$ | ⬡ | ⌇ |

EXAMPLE 6

Preparation of 4-(4-pentylbenzyloxy)-1-(1,5-hexadienyl)benzene

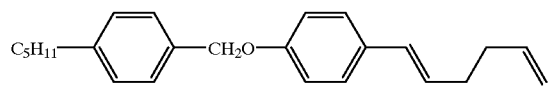

(Compound No. 279 expressed by general formula (1) wherein $R_1$ represents pentyl group, $X_3$ represents —CH$_2$O—, C and D represent 1,4-phenylene ring, l, m, and n are 0, o is 1, p is 2, and $R_2$ and $R_2'$ are hydrogen atom.) Solution of the 4-(1,5-hexadienyl)phenol (500 mmol) obtained by the same method as in Example 4 in 120 ml of THF was added dropwise to a mixture of sodium hydride (120 mmol), 20 ml of THF, and 50 ml of DMF, and stirred for about 2 hours until generation of hydrogen gas ceased. To this solution was added dropwise a solution of 4-pentylbenzylbromide (45 mmol) in 50 ml of THF at a temperature lower than 0° C. and stirred for further 5 hours. Water in an amount of 100 ml and 100 ml of toluene were added to this solution, and the organic layer was washed with 100 ml of 2M hydrochloric acid and 100 ml of saturated aqueous solution of sodium bicarbonate, washed with water until it became neutral, and then dried with anhydrous magnesium sulfate. The solvent was distilled off under a reduced pressure and the residue was recrystallized from ethanol 5 times as much as the residue to obtain 21 mmol of white oily subject compound. NMR spectrum, mass spectrum, IR spectrum, and the values of elementary analysis of this compound well supported its structure.

According to the method of Example 6, the following compounds were prepared:

| | R1 | A | X1 | B | X2 | C | X3 | D | W |
|---|---|---|---|---|---|---|---|---|---|
| 277 | C₃H₇ | | | | |  | CH₂O |  | 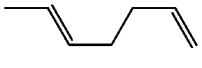 |
| 278 | C₃H₇ | | | | |  | CH₂O |  | 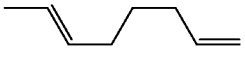 |
| 279 | C₅H₁₁ | | | | |  | CH₂O |  | 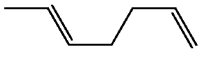 |
| 280 | C₃H₇ | | | | |  | OCH₂ |  |  |
| 281 | C₅H₁₁ | | | | |  | OCH₂ |  | 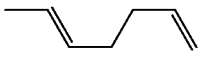 |
| 282 | C₃H₇ | | |  | OCH₂ |  | |  |  |
| 283 | C₄H₉ | | |  | OCH₂ | 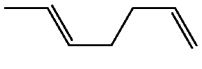 | |  |  |
| 284 | C₅H₁₁ | | | 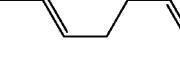 | OCH₂ |  | |  | 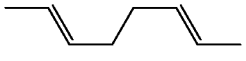 |
| 285 | C₅H₁₁ | | |  | OCH₂ |  | |  |  |
| 286 | CH₃ | | |  | CH₂O | 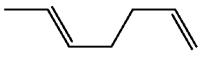 | |  |  |
| 287 | C₃H₇ | | |  | CH₂O | | | | |
| 288 | C₂H₅ | | | | OCH₂ | | | | |

-continued
| | R1 | A | X1 | B | X2 | C | X3 | D | W |
|---|---|---|---|---|---|---|---|---|---|
| 289 | C3H7 | | |  | OCH2 |  | |  | 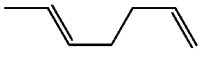 |
| 290 | C3H7 | | |  | |  | OCH2 |  |  |
| 291 | C5H11 | | |  | |  | OCH2 |  | 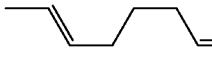 |
| 292 | C3H7 | | |  | |  | CH2O |  | 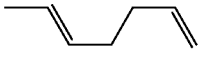 |
| 293 | C5H11 | | |  | |  | CH2O |  | 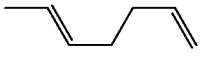 |
| 294 | CH3OCH2 | | |  | |  | CH2O |  | 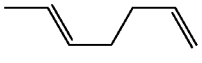 |
| 295 | C5H11 | | |  | |  | CH2O |  | 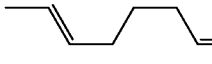 |
| 296 | C3H7 | | |  | |  | OCH2 |  | 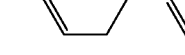 |
| 297 | CH3-OCH2CH2 | | |  | |  | OCH2 |  | 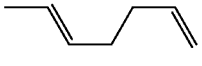 |
| 298 | FCH2CH2 | | |  | |  | OCH2 |  | 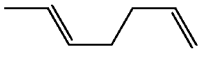 |
| 299 | C3H7 |  | |  | OCH2 |  | |  |  |
| 300 | C5H11 |  | |  | OCH2 | | | |  |

-continued

| | R1 | A | X1 | B | X2 | C | X3 | D | W |
|---|---|---|---|---|---|---|---|---|---|
| 301 | C$_3$H$_7$ | ⬡ | CH$_2$O | ⬡ | | ⬡ | | ⬡ | ⤳ |
| 302 | C$_3$H$_7$ | ⬡ | | ⬡ | OCH$_2$ | ⬡ | | ⬡ | ⤳ |
| 303 | C$_5$H$_{11}$ | ⬡ | | ⬡ | OCH$_2$ | ⬡ | | ⬡ | ⤳ |
| 304 | C$_3$H$_7$ | ⬡ | | ⬡ | | ⬡ | OCH$_2$ | ⬡ | ⤳ |
| 305 | C$_5$H$_{11}$ | ⬡ | | ⬡ | | ⬡ | OCH$_2$ | ⬡ | ⤳ |

EXAMPLE 7

(Use Example 1)

Liquid Crystal Composition B1 comprising the following compounds was prepared:

| | |
|---|---|
| 4-(4-propylcyclohexyl)benzonitrile | 24% |
| 4-(4-pentylcyclohexyl)benzonitrile | 36% |
| 4-(4-heptylcyclohexyl)benzonitrile | 25% |
| 4-(4-(4-pentylcyclohexyl)phenyl)benzonitrile | 15% |

This nematic liquid crystal composition had a clearing point of 72.4° C., threshold voltage of 1.78 V at a cell thickness of 9 μm, value of dielectric anisotropy of 11.0, optical anisotropy of 0.137, and viscosity of 27.0 mpa.s at 20° C. This liquid crystal composition in an amount of 85% was mixed with 15% of the compound (Compound No. 8) of the present invention obtained in Example 1 to prepare Liquid Crystal Composition A1. This composition had a clearing point of 75.0° C., threshold voltage of 1.84 V at a cell thickness of 8.9 μm, value of dielectric anisotropy of 9.6, optical anisotropy of 0.126, viscosity of 20.7 mPa.s at 20° C., and ratio of elastic constants K$_{33}$/K$_{11}$ of 2.02. Further, the extrapolation value calculated from the mixing ratio were 89.7° C. for the clearing point, 1.7 for the value of dielectric anisotropy, 0.063 for the optical anisotropy, and −15.0 mPa.s for the viscosity, respectively.

While this liquid crystal composition was left in a freezer at −20° C. for 60 days, precipitation of crystals was not noticed.

EXAMPLE 8

(Use Example 2)

Clearing point, viscosity at 20° C., optical anisotropy at 25° C., and threshold voltage at a cell thickness of 8.7 μm of the liquid crystal composition shown in Composition Example 1 were determined to find to be 101.9° C., 16.02 mPa.s, 0.132, and 2.10 V, respectively.

Comparative Example 1

The following compound

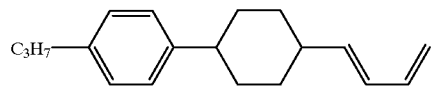

prepared by the method described in Laid-open Japanese Patent Publication No. Hei 6-151447 was added in an amount of 15% to the Liquid Crystal Composition B1 to prepare Liquid Crystal Composition A2. A1 obtained in Example 7 and A2 were simultaneously heated at 100° C. for 2 hours and change of clearing point was observed.

| Composition | Clearing point before heating | Clearing point after heating |
|---|---|---|
| A1 | 75.0° C. | 74.8° C. |
| A2 | 62.8° C. | 55.1° C. |

It was found that whereas the clearing point of Liquid Crystal Composition A2 was reduced by about 7° C., the reduction of clearing point of Liquid Crystal Composition A1 was only 0.2° C., and thus that the compound of general formula (1) are extremely stable.

According to the procedures mentioned above, the following compositions were prepared and their physical parameters were determined:

In the following composition examples, compounds are designated by code addresses according to the understanding in the following Table. That is, left side terminal group is expressed by a—, aO—, aOb—, Va—, aVb—, or aVbVd—;

bonding group is expressed by 2, E, T, V, or CF2O; ring structure is expressed by B, B(F), B(F,F), H, Py, D, or Ch; and right side terminal group is expressed by —F, —CL, —C, —CF3, —OCF3, —OCF2H, —w, —Ow, or EMe.

| Left side terminal group | Symbol | Bonding group | Symbol |
|---|---|---|---|
| $C_aH_{2a+1}$— | a- | —$CH_2CH_2$— | 2 |
| $C_aH_{2a+1}O$— | aO- | —COO— | E |
| $C_aH_{2a+1}OC_bH_{2b}$— | aOb- | —C≡C— | T |
| $CH_2=CHC_aH_{2a}$— | Va- | —CH=CH— | V |
| $C_2H_{2a+1}CH=CHC_bH_{2b}$— | aVb- | —$CF_2O$— | CF2O |
| $C_aH_{2a+1}CH=CHC_bH_{2b}CH=CHC_dH_{2d}$— | aVbVd- | | |

| Ring structure | Symbol | Right side terminal group | Symbol |
|---|---|---|---|
|  | B | —F | —F |
| 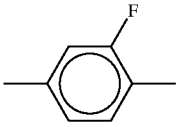 | B(F) | —Cl | —CL |
| 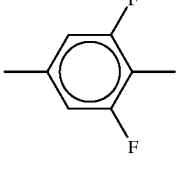 | B(F,F) | —CN | —C |
| 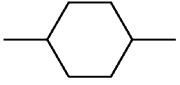 | H | —$CF_3$ | —CF3 |
|  | Py | —$OCF_3$ | —OCF3 |
|  | D | —$OCF_2H$ | —OCF2H |
| 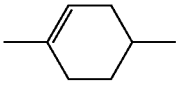 | CH | —$C_wH_{2w+1}$ | —w |
| | | —$OC_wH_{2w+1}$ | —Ow |
| | | —COOCH3 | —EMe |

EXAMPLE 9

(Use Example 3)

| | |
|---|---|
| V2V-HBB-2 (Compound No. 62) | 10% |
| 1V2-BEB(F,F)-C | 8% |
| 3-HB-C | 24% |
| 3-HB-O2 | 5% |
| 3-HH-4 | 11% |
| 3-HH-5 | 5% |
| 3-HHB-1 | 10% |
| 3-HHB-3 | 11% |

-continued

| | |
|---|---|
| 3-H2BTB-2 | 4% |
| 3-H2BTB-3 | 4% |
| 3-H2BEB-4 | 4% |
| 3-HB(F)TB-2 | 2% |
| 3-HB(F)TB-3 | 2% |

Physical parameters of the liquid crystal composition shown above were as follows:

| | |
|---|---|
| Clearing point [°C.] | 100.6 |
| Viscosity [mPa · s] | 17.8 |
| Optical anisotropy | 0.132 |
| Threshold voltage [V] | 2.09 |

EXAMPLE 10

(Use Example 4)

| | |
|---|---|
| V2V-HH-1 (Compound No. 1) | 18% |
| 1V2-BEB(F,F)-C | 9% |
| 3-HB-C | 21% |
| 3-HHB-1 | 10% |
| 3-HHB-3 | 15% |
| 2-HHB-1 | 2% |
| 3-HHB-01 | 3% |
| 3-H2BTB-2 | 4% |
| 3-H2BTB-3 | 4% |
| 3-H3BTB-4 | 4% |
| 3-HB(F)TB-2 | 4% |
| 3-HB(F)TB-3 | 3% |
| 3-HB(F)TB-4 | 3% |

Physical parameters of the liquid crystal composition shown above were as follows:

| | |
|---|---|
| Clearing point [°C.] | 99.8 |
| Viscosity [mPa · s] | 16.2 |
| Optical anisotropy | 0.135 |
| Threshold voltage [V] | 2.01 |

EXAMPLE 11

(Use Example 5)

| | |
|---|---|
| V2V-HB-C (Compound No. 16) | 14% |
| 1V2-BEB(F,F)-C | 8% |
| 3-HB-C | 10% |
| 3-HB-CO2 | 7% |
| 3-HH-4 | 11% |
| 3-HH-5 | 5% |
| 3-HHB-1 | 10% |
| 3-HHB-3 | 15% |
| 3-H2BTB-2 | 4% |
| 3-H2BTB-3 | 4% |
| 3-H2BTB-4 | 4% |
| 3-HB(F)TB-2 | 2% |
| 3-HB(F)TB-3 | 3% |
| 3-HB(F)TB-4 | 3% |

Physical parameters of the liquid crystal composition shown above were as follows:

| | |
|---|---|
| Clearing point [°C.] | 100.2 |
| Viscosity [mPa · s] | 17.2 |
| Optical anisotropy | 0.132 |
| Threshold voltage [V] | 2.06 |

EXAMPLE 12

(Use Example 6)

| | |
|---|---|
| V2V-HH-4 (Compound No. 7) | 15% |
| 1V2-BEB(F,F)-C | 8% |
| 3-HB-C | 24% |
| 3-HB-02 | 6% |
| 3-HHB-1 | 10% |
| 3-HHB-3 | 15% |
| 2-HHB-1 | 2% |
| 3-H2BTB-2 | 4% |
| 3-H2BTB-3 | 4% |
| 3-H2BTB-4 | 4% |
| 3-HB(F)TB-3 | 4% |
| 3-HB(F)TB-4 | 4% |

Physical parameters of the liquid crystal composition shown above were as follows:

| | |
|---|---|
| Clearing point [°C.] | 100.6 |
| Viscosity [mPa · s] | 18.1 |
| Optical anisotropy | 0.133 |
| Threshold voltage [V] | 2.05 |

EXAMPLE 13

(Use Example 7)

| | |
|---|---|
| V2V-HH-3 (Compound No. 3) | 5% |
| V2V2-HH-5 (Compound No. 172) | 10% |
| 3-PyB(F)-F | 8% |
| 2-HB(F)-C | 8% |
| 3-HB(F)-C | 8% |
| 3-HB-C | 4% |
| 2-HHB(F)-F | 6% |
| 3-HHB(F)-F | 6% |
| 5-HHB(F)-F | 6% |
| 3-HHB-1 | 9% |
| 3-HHB-3 | 8% |
| 3-HHB-01 | 3% |
| 2-HHB(F)-C | 3% |
| 3-HHB(F)-C | 7% |
| 3-PyBB-F | 3% |
| 4-PyBB-F | 3% |
| 5-PyB-F | 3% |

Physical parameters of the liquid crystal composition shown above were as follows:

| | |
|---|---|
| Clearing point [°C.] | 87.5 |
| Viscosity [mPa · s] | 22.4 |
| Optical anisotropy | 0.109 |
| Dielectric anisotropy | 9.4 |
| Threshold voltage [V] | 1.60 |

EXAMPLE 14

(Use Example 8)

| | |
|---|---|
| V2V-HBB-2 (Compound 62) | 5% |
| V2V-HB-C (Compound 16) | 8% |
| V2-HB-C | 10% |
| 1V2-HB-C | 10% |
| 3-HB-C | 20% |
| 5-HB-C | 10% |

| | |
|---|---|
| 2-PyB-2 | 3% |
| 3-PyB-2 | 3% |
| 4-PyB-2 | 3% |
| 3-HHB-1 | 3% |
| 3-HHB-3 | 5% |
| 3-HHB-O1 | 5% |
| 3-H2BTB-2 | 5% |
| 2-PyBH-3 | 2% |
| 3-PyBH-3 | 2% |
| 3-PyBB-F | 2% |
| 2-DB-C | 2% |
| 3-DB-C | 2% |

Physical parameters of the liquid crystal composition shown above were as follows:

| | |
|---|---|
| Clearing point [°C.] | 76.0 |
| Viscosity [mPa · s] | 21.0 |
| Optical anisotropy | 0.139 |
| Dielectric anisotropy | 9.5 |
| Threshold voltage [V] | 1.70 |

EXAMPLE 15

(Use Example 9)

| | |
|---|---|
| V2V-HH-1 (Compound No. 1) | 3% |
| V2V-HH-5 (Compound No. 8) | 7% |
| V2V-HB-C (Compound No. 16) | 5% |
| V2-HB-C | 8% |
| 1V2-HB-C | 8% |
| 3-HB-C | 8% |
| 5-HB-C | 10% |
| 101-HB-C | 8% |
| 201-HB-C | 5% |
| 2-BTB-01 | 2% |
| 3-BTB-01 | 2% |
| 4-BTB-01 | 2% |
| 4-BTB-02 | 2% |
| 5-BTB-01 | 2% |
| V2-HH-3 | 8% |
| 3-HHB-1 | 5% |
| 3-HHB-3 | 5% |
| 3-HHB-C | 10% |

Physical parameters of the liquid crystal composition shown above were as follows:

| | |
|---|---|
| Clearing point [°C.] | 75.5 |
| Viscosity [mPa · s] | 18.8 |
| Optical anisotropy | 0.125 |
| Dielectric anisotropy | 8.4 |
| Threshold voltage [V] | 1.76 |

EXAMPLE 16

(Use Example 10)

| | |
|---|---|
| V2V-HB-C (Compound No. 16) | 5.0% |
| V2V-HH-3 (Compound No. 3) | 5.0% |
| V2V-HH-4 (Compound No. 7) | 5.0% |
| 2-BB-C | 6.0% |
| 4-BB-C | 6.0% |
| 5-BB-C | 6.0% |
| 2-HB-C | 10.0% |
| 3-HB-C | 10.0% |
| 3-PyB-4 | 1.5% |
| 4-PyB-4 | 1.5% |
| 6-PyB-4 | 1.5% |
| 3-PyB-5 | 1.5% |
| 4-PyB-5 | 1.5% |
| 6-PyB-5 | 1.5% |
| 2-HHB-1 | 3.0% |
| 3-HHB-1 | 5.0% |
| 3-HHB-3 | 8.0% |
| 3-HHB-O1 | 3.0% |
| 3-HHB-F | 3.0% |
| 2-PyB-O2 | 2.0% |
| 3-PyB-O2 | 2.0% |
| 2-HHB-C | 4.0% |
| 3-HHB-C | 4.0% |
| 4-HHB-C | 4.0% |

Physical parameters of the liquid crystal composition shown above were as follows:

| | |
|---|---|
| Clearing point [°C.] | 78.8 |
| Viscosity [mPa · s] | 21.9 |
| Optical anisotropy | 0.135 |
| Dielectric anisotropy | 8.3 |
| Threshold voltage [V] | 1.73 |

EXAMPLE 17

(Use Example 11)

| | |
|---|---|
| V2V1-HH-5 (Compound No. 170) | 5% |
| V2V-H2H-3 (Compound No. 9) | 5% |
| 201-BEB(F)-C | 6% |
| 301-BEB(F)-C | 6% |
| 101-HB-C | 5% |
| 2-HB-C | 20% |
| 3-HB-C | 15% |
| 2-HHB-C | 4% |
| 3-HHB-C | 4% |
| 4-HHB-C | 4% |
| 3-PyBB-F | 3% |
| 101-HH-5 | 8% |
| 3-HHB-1 | 3% |
| 3-HHEB-F | 3% |
| 5-HHEB-F | 3% |
| 3-PyBB-2 | 3% |
| 4-PyBB-3 | 3% |

Physical parameters of the liquid crystal composition shown above were as follows:

| | |
|---|---|
| Clearing point [°C.] | 67.7 |
| Viscosity [mPa · s] | 26.9 |
| Optical anisotropy | 0.119 |
| Dielectric anisotropy | 12.2 |
| Threshold voltage [V] | 1.24 |

EXAMPLE 18

(Use Example 12)

| | |
|---|---|
| V2V-HHB(F)-F (Compound No. 178) | 5% |
| V2V-H2H-3 (Compound No. 9) | 10% |
| V2V-HB-C (Compound No. 16) | 3% |

-continued

| | |
|---|---|
| 3-HB-C | 10% |
| 101-HB-C | 8% |
| 2-BTB-1 | 4% |
| 1-BTB-6 | 8% |
| 4-BTB-4 | 4% |
| 3-HHB-C | 3% |
| 2-H2HB(F)-F | 10% |
| 3-H2HB(F)-F | 5% |
| 5-H2HB(F)-F | 10% |
| 3-HHB-01 | 3% |
| 3-HHB-1 | 7% |
| V-HHB-1 | 3% |
| 3-HB(F)TB-2 | 3% |

Physical parameters of the liquid crystal composition shown above were as follows:

| | |
|---|---|
| Clearing point [°C.] | 82.6 |
| Viscosity [mPa · s] | 19.4 |
| Optical anisotropy | 0.121 |
| Dielectric anisotropy | 5.6 |
| Threshold voltage [V] | 2.11 |

EXAMPLE 19

(Use Example 13)

| | |
|---|---|
| V2V-H2H-3 (Compound No. 9) | 10% |
| V2V-HBB-2 (Compound No. 62) | 5% |
| V2V2-HH-5 (Compound No. 172) | 7% |
| 2-HB(F)-C | 3% |
| 4-HB(F)-C | 3% |
| 5-HB(F)-C | 3% |
| 2-BEB-C | 3% |
| 10-BEB-C | 5% |
| 5-HEB-F | 4% |
| 7-HEB-F | 4% |
| 3-HEB-04 | 8% |
| 4-HEB-02 | 6% |
| 5-HEB-01 | 6% |
| 3-HEB-02 | 5% |
| 5-HEB-02 | 4% |
| 4-HEB-04 | 8% |
| 3-HHB-1 | 5% |
| 3-HHB-3 | 5% |
| 3-HHB-01 | 3% |
| 3-HEBEB-F | 3% |

Physical parameters of the liquid crystal composition shown above were as follows:

| | |
|---|---|
| Clearing point [°C.] | 76.8 |
| Viscosity [mPa · s] | 20.9 |
| Optical anisotropy | 0.094 |
| Dielectric anisotropy | 2.7 |
| Threshold voltage [V] | 2.56 |

EXAMPLE 20

(Use Example 14)

| | |
|---|---|
| V2V-HH-3 (Compound No. 3) | 5% |
| V2V-HH-4 (Compound No. 7) | 5% |
| V2V1-HH-5 (Compound No. 170) | 5% |
| 3-PyB(F)-F | 8% |

-continued

| | |
|---|---|
| 3-PyBB-F | 5% |
| 4-PyBB-F | 5% |
| 5-PyBB-F | 5% |
| 2-PyB-2 | 5% |
| 3-PyB-2 | 5% |
| 4-PyB-2 | 5% |
| 3-HEB-04 | 6% |
| 4-HEB-02 | 6% |
| 5-HEB-02 | 6% |
| 3-HH-EMe | 3% |
| 2-H2BTB-4 | 5% |
| 3-H2BTB-4 | 5% |
| 3-HHB-1 | 6% |
| 3-HHB-3 | 6% |
| 3-HHEBB-C | 2% |
| 3-HBEBB-C | 2% |

Physical parameters of the liquid crystal composition shown above were as follows:

| | |
|---|---|
| Clearing point [°C.] | 80.3 |
| Viscosity [mPa · s] | 22.5 |
| Optical anisotropy | 0.142 |
| Dielectric anisotropy | 3.6 |
| Threshold voltage [V] | 2.47 |

EXAMPLE 21

(Use Example 15)

| | |
|---|---|
| V2V-HH-3 (Compound No. 3) | 5% |
| V2V-HH-4 (Compound No. 7) | 5% |
| V2V-HH-5 (Compound No. 8) | 6% |
| 7-HB(F)-F | 4% |
| 5-H2B(F)-F | 6% |
| 2-HHB(F)-F | 12% |
| 3-HHB(F)-F | 12% |
| 5-HHB(F)-F | 12% |
| 2-H2HB(F)-F | 2% |
| 3-H2HB(F)-F | 1% |
| 5-H2HB(F)-F | 2% |
| 2-HBB(F)-F | 4% |
| 3-HBB(F)-F | 4% |
| 5-HBB(F)-F | 8% |
| 2-HBB-F | 3% |
| 3-HBB-F | 3% |
| 5-HBB-F | 2% |
| 3-HHB-F | 3% |
| 3-HHB-1 | 6% |

Physical parameters of the liquid crystal composition shown above were as follows:

| | |
|---|---|
| Clearing point [°C.] | 91.9 |
| Viscosity [mPa · s] | 19.1 |
| Optical anisotropy | 0.088 |
| Dielectric anisotropy | 3.5 |
| Threshold voltage [V] | 2.55 |

EXAMPLE 22

(Use Example 16)

| | |
|---|---|
| V2V-HHB(F,F)-F (Compound No. 179) | 5% |
| V2V-HH-5 (Compound No. 8) | 5% |

| | |
|---|---|
| V1V-HH-5 (Compound No. 173) | 3% |
| 7-HB(F,F)-F | 8% |
| 3-HHB(F,F)-F | 3% |
| 4-HHB(F,F)-F | 3% |
| 3-H2HB(F,F)-F | 10% |
| 4-H2HB(F,F)-F | 8% |
| 5-H2HB(F,F)-F | 8% |
| 3-HH2B(F,F)-F | 5% |
| 5-HH2B(F,F)-F | 5% |
| 3-HBB(F,F)-F | 8% |
| 5-HBB(F,F)-F | 3% |
| 3-H2BB(F,F)-F | 3% |
| 5-H2BB(F,F)-F | 3% |
| 2-HHB-OCF3 | 3% |
| 3-HH2B-OCF3 | 5% |
| 5-HH2B-OCF3 | 4% |

Physical parameters of the liquid crystal composition shown above were as follows:

| | |
|---|---|
| Clearing point [°C.] | 74.7 |
| Viscosity [mPa · s] | 22.1 |
| Optical anisotropy | 0.083 |
| Dielectric anisotropy | 5.6 |
| Threshold voltage [V] | 1.06 |

EXAMPLE 23

(Use Example 17)

| | |
|---|---|
| V2V-HHB(F,F)-F (Compound No. 179) | 10% |
| V2V2-HH-4 (Compound No. 172) | 6% |
| 3-H2HB(F,F)-F | 7% |
| 4-H2HB(F,F)-F | 7% |
| 5-H2HB(F,F)-F | 6% |
| 3-HH2B(F,F)-F | 5% |
| 3-HBB(F,F)-F | 16% |
| 5-HBB(F,F)-F | 16% |
| 3-H2BB(F,F)-F | 5% |
| 4-H2BB(F,F)-F | 5% |
| 5-H2BB(F,F)-F | 5% |
| 3-HBEB(F,F)-F | 2% |
| 5-HBEB(F,F)-F | 2% |
| 3-HHEB(F,F)-F | 3% |
| 3-H2HB-OCF3 | 3% |
| 5-H2HB-OCF3 | 2% |

Physical parameters of the liquid crystal composition shown above were as follows:

| | |
|---|---|
| Clearing point [°C.] | 74.8 |
| Viscosity [mPa · s] | 26.7 |
| Optical anisotropy | 0.101 |
| Dielectric anisotropy | 8.7 |
| Threshold voltage [V] | 1.63 |

EXAMPLE 24

(Use Example 18)

| | |
|---|---|
| V2V-HHB(F,F)-F (Compound No. 179) | 7.0% |
| V2V-HHB(F)-F (Compound No. 178) | 7.0% |
| V2V-H2H-3 (Compound No. 9) | 7.0% |
| 3-HB-CL | 5.0% |
| 2-HHB-CL | 4.0% |
| 4-HHB-CL | 8.0% |
| 5-HHB-CL | 4.0% |
| 7-HB(F,F)-F | 2.0% |
| 2-HBB(F)-F | 4.5% |
| 3-HBB(F)-F | 4.5% |
| 5-HBB(F)-F | 9.0% |
| 3-HBB(F,F)-F | 10.0% |
| 5-HBB(F,F)-F | 10.0% |
| 3-HB(F)VB-2 | 4.0% |
| 3-HB(F)VB-3 | 4.0% |
| 3-H2HB(F)-CL | 4.0% |
| 5-HB-F | 3.0% |
| 7-HB-F | 3.0% |

Physical parameters of the liquid crystal composition shown above were as follows:

| | |
|---|---|
| Clearing point [°C.] | 94.4 |
| Viscosity [mPa · s] | 21.3 |
| Optical anisotropy | 0.119 |
| Dielectric anisotropy | 5.3 |
| Threshold voltage [V] | 2.22 |

APPLICATION IN INDUSTRY

Liquid crystalline compounds of the present invention have a large ratio of elastic constants, have a low viscosity compared with existing liquid crystalline compounds, are excellent in miscibility with other liquid crystalline compounds, particularly in that miscibility at low temperatures, and are chemically stable. Thus, the liquid crystal compositions having excellent physical properties, that is, steep threshold characteristics and high response speed can be obtained by including the liquid crystalline compounds in a liquid crystal composition.

We claim:

1. A liquid crystalline compound expressed by the following general formula (1)

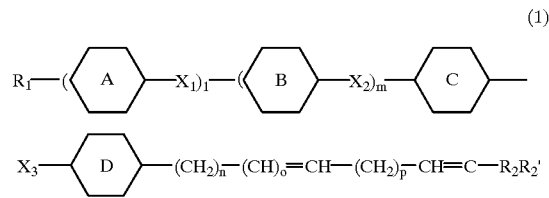

wherein $R_1$ represents cyano group, a halogen atom, or a straight or branched alkyl group or halogenated alkyl group having 1 to 20 carbon atoms, one or not-adjacent two $CH_2$ groups in the alkyl or halogenated alkyl group may be replaced by oxygen atom or —CH═CH— group; $R_2$ and $R_2'$ represent hydrogen atom, a halogen atom, or an alkyl group having 1 to 9 carbon atoms; $X_1$, $X_2$ and $X_3$ independently represent —CH$_2$CH$_2$—, —CO═O—, —O—CO—, —CH═CH—, —(CH$_2$)$_4$—, —CF$_2$O—, —OCF$_2$—, —CH$_2$O—, —OCH$_2$—, or a covalent bond; rings A, B, C, and D independently represent 1,4-phenylene ring, trans-1, 4-cyclohexylene ring, cyclobutane ring, or spiro[3,3] heptane ring, respectively, hydrogen atom in these rings may be replaced by a halogen atom and carbon atom in these rings may be replaced by nitrogen atom or oxygen atom provided that two rings in which carbon atom is replaced by nitrogen atom or oxygen atom are not bonded with a covalent bond, and provided that ring D does not represent trans-1,4-cyclohexylene or trans-1,3-dioxane-2,5-diyl; l and m are independently an integer of 0 or 1, o is 1, n is an integer of 0 to 3; and p is an integer of 1 to 5.

2. The liquid crystalline compound according to claim 1 wherein n is 0, o is 1, p is 2, and $R_2$ and $R_2{}'$ represent hydrogen atom, respectively.

3. The liquid crystalline compound according to claim 2 wherein at least one of $X_1$, $X_2$, and $X_3$ is a covalent bond.

4. The liquid crystalline compound according to claim 3 wherein $X_1$, $X_2$, and $X_3$ are —CH$_2$CH$_2$—, —CH=CH—, —(CH$_2$)$_4$—, or a covalent bond.

5. A liquid crystal composition comprising at least two components and containing at least one compound defined in any one of claims 2 to 5 or 1 in at least one of the components.

6. A liquid crystal display device comprising a liquid crystal composition defined in claim 5.

7. A liquid crystal composition comprising, as a first component, at least one liquid crystalline compound expressed by following general formula (1)

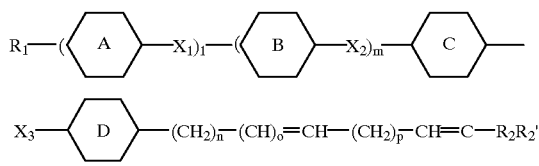

(1)

wherein $R_1$ represents cyano group, a halogen atom, or a straight or branched alkyl group or halogenated alkyl group having 1 to 20 carbon atoms, one or not-adjacent two CH$_2$ groups in the alkyl or halogenated alkyl group may be replaced by oxygen atom or —CH=CH— group; $R_2$ and $R_2{}'$ represent hydrogen atom, a halogen atom, or an alkyl group having 1 to 9 carbon atoms; $X_1$, $X_2$ and $X_3$ independently represent —CH$_2$CH$_2$—, —CO—O—, —O—CO—, —CH=CH—, —C≡C—, —(CH$_2$)$_4$—, —CF$_2$O—, —OCF$_2$—, —CH$_2$O—, —OCH$_2$—, or a covalent bond; rings A, B, C, and D independently represent 1,4-phenylene ring, trans-1,4-cyclohexylene ring, cyclobutane ring, or spiro[3,3]heptane ring, respectively, hydrogen atom in these rings may be replaced by a halogen atom and carbon atom in these rings may be replaced by nitrogen atom or oxygen atom provided that two rings in which carbon atom is replaced by nitrogen atom or oxygen atom are not bonded with a covalent bond, and provided that ring D does not represent trans-1,4-cyclohexylene or trans-1,3-dioxane-2,5-diyl; l and m are independently an integer of 0 or 1, o is 1, n is an integer of 0 to 3; and p is an integer of 1 to 5, and as a second component, one or more compounds selected from the group consisting of the compounds expressed by the general formula (2), (3), or (4)

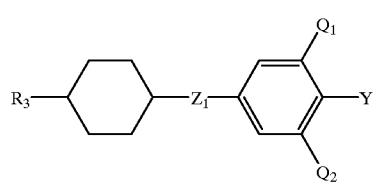

(2)

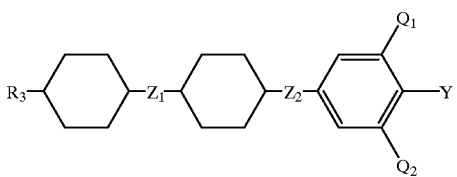

(3)

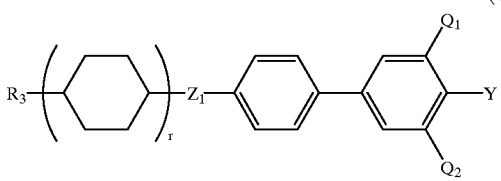

(4)

in which $R_3$ represents an alkyl group having 1 to 10 carbon atoms, Y represents F or Cl, $Q_1$ and $Q_2$ independently represent H or F, r is 1 or 2, and $Z_1$ and $Z_2$ independently represent —CH$_2$CH$_2$— or a covalent bond.

8. A liquid crystal composition comprising, as a first component, at least one liquid crystalline compound expressed by following general formula (1)

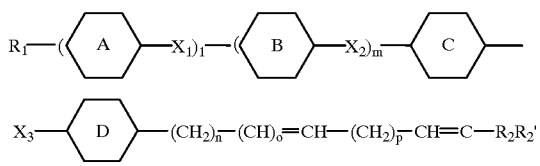

(1)

wherein $R_1$ represents cyano group, a halogen atom, or a straight or branched alkyl group or halogenated alkyl group having 1 to 20 carbon atoms, one or not-adjacent two CH$_2$ groups in the alkyl or halogenated alkyl group may be replaced by oxygen atom or —CH=CH— group; $R_2$ and $R_2{}'$ represent hydrogen atom, a halogen atom, or an alkyl group having 1 to 9 carbon atoms; $X_1$, $X_2$ and $X_3$ independently represent —CH$_2$CH$_2$—, —CO—O—, —O—CO—, —CH=CH—, —C≡C—, —(CH$_2$)$_4$—, —CF$_2$O—, —OCF$_2$—, —CH$_2$O—, —OCH$_2$—, or a covalent bond; rings A, B, C, and D independently represent 1,4-phenylene ring, trans-1,4-cyclohexylene ring, cyclobutane ring, or spiro[3,3]heptane ring, respectively, hydrogen atom in these rings may be replaced by a halogen atom and carbon atom in these rings may be replaced by nitrogen atom or oxygen atom provided that two rings in which carbon atom is replaced by nitrogen atom or oxygen atom are not bonded with a covalent bond, and provided that ring D does not represent trans-1,4-cyclohexylene or trans-1,3-dioxane-2,5-diyl; l and m are independently an integer of 0 or 1, o is 1, n is an integer of 0 to 3; and p is an integer of 1 to 5, and as a second component, one or more compounds selected from the group consisting of the compounds expressed by the general formula (5), (6), (7), (8), or (9)

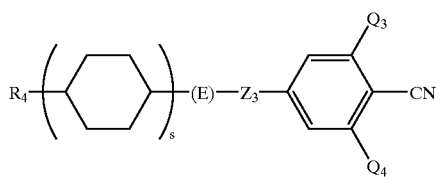
(5)

in which $R_4$ represents an alkyl group having 1 to 10 carbon atoms or an alkenyl group having 2 to 10 carbon atoms, in either case any methylene group (—$CH_2$—) in the alkyl or alkenyl group may be replaced by oxygen atom (—O—) provided that in no case two or more methylene groups are continuously replaced by oxygen atom; $Z_3$ represents —$CH_2CH_2$—, —COO—, or a covalent bond; $Q_3$ and $Q_4$ represent H or F, E represents cyclohexylene ring, benzene ring, or 1,3-dioxane ring, and s is an integer of 0 or 1,

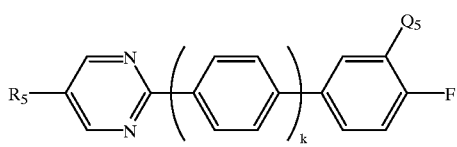
(6)

in which $R_5$ represents an alkyl group having 1 to 10 carbon atoms, $Q_5$ represents H or F, and k is an integer of 0 or 1,

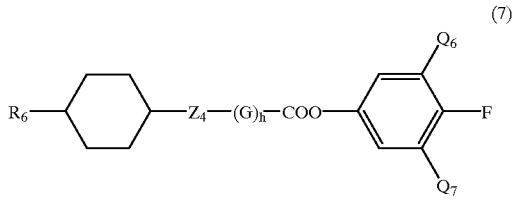
(7)

in which $R_6$ represents an alkyl group having 1 to 10 carbon atoms, G represents cyclohexane ring or benzene ring, $Q_6$ and $Q_7$ independently represent H or F, $Z_4$ represents —COO— or a covalent bond, and h is an integer of 0 or 1,

(8)

in which $R_7$ and $R_8$ independently represent an alkyl group, alkyloxy group, or alkyloxymethyl group having 1 to 10 carbon atoms, H represents cyclohexane ring, pyrimidine ring, or benzene ring; J represents cyclohexane ring or benzene ring, $Z_5$ represents —C≡C—, —COO—, —$CH_2CH_2$—, or a covalent bond,

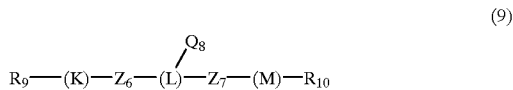
(9)

in which $R_9$ represents an alkyl group or alkoxy group having 1 to 10 carbon atoms, $R_{10}$ represents an alkyl group, alkyloxy group, or alkoxymethyl group having 1 to 10 carbon atoms, K represents cyclohexane ring or pyrimidine ring, each of L and M independently represent cyclohexane ring or benzene ring, $Z_6$ represents —COO—, —$CH_2CH_2$—, or a covalent bond, $Z_7$ represents —C≡C—,—COO—, or a covalent bond, and $Q_8$ represents H or F.

9. A liquid crystal display device comprising a liquid crystal composition defined in claim 7.

10. A liquid crystal display device comprising a liquid crystal composition defined in claim 8.

11. The liquid crystalline compound according to claim 1 wherein p is 2 to 5.

12. The liquid crystal composition according to claim 7 wherein p is 2 to 5.

13. The liquid crystal composition according to claim 8 wherein p is 2 to 5.

* * * * *